(12) United States Patent
Krieg

(10) Patent No.: US 7,807,803 B2
(45) Date of Patent: Oct. 5, 2010

(54) NUCLEIC ACID COMPOSITIONS FOR STIMULATING IMMUNE RESPONSES

(75) Inventor: Arthur M. Krieg, Wellesley, MA (US)

(73) Assignee: Coley Pharmaceutical Group, Inc., New York, NY (US)

( * ) Notice: Subject to any disclaimer, the term of this patent is extended or adjusted under 35 U.S.C. 154(b) by 2099 days.

(21) Appl. No.: 10/613,736

(22) Filed: Jul. 3, 2003

(65) Prior Publication Data

US 2004/0152649 A1 Aug. 5, 2004

Related U.S. Application Data

(60) Provisional application No. 60/394,164, filed on Jul. 3, 2002.

(51) Int. Cl.
*A01N 43/04* (2006.01)
*A01N 25/08* (2006.01)
*A61K 9/52* (2006.01)
*A61K 9/22* (2006.01)
*A61K 31/70* (2006.01)
*C07H 21/04* (2006.01)
*C07H 21/00* (2006.01)

(52) U.S. Cl. .................... 536/23.1; 514/2; 424/408; 424/409; 424/422; 424/430; 424/450; 424/457; 424/468; 424/490

(58) Field of Classification Search .................. 514/44; 536/23.1; 424/408, 409, 422, 430, 450, 424, 424/457, 468, 490
See application file for complete search history.

(56) References Cited

U.S. PATENT DOCUMENTS

| | | | |
|---|---|---|---|
| 4,806,463 A | 2/1989 | Goodchild et al. |
| 5,004,810 A | 4/1991 | Draper |
| 5,166,195 A | 11/1992 | Ecker |
| 5,194,428 A | 3/1993 | Agrawal et al. |
| 5,264,423 A | 11/1993 | Cohen et al. |
| 5,276,019 A | 1/1994 | Cohen et al. |
| 5,416,203 A | 5/1995 | Letsinger |
| 5,663,153 A | 9/1997 | Hutcherson et al. |
| 5,723,335 A | 3/1998 | Hutcherson et al. |
| 5,780,448 A | 7/1998 | Davis |
| 6,030,955 A | 2/2000 | Stein et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,521,637 B2 | 2/2003 | Macfarlane |
| 6,558,670 B1 | 5/2003 | Friede et al. |
| 6,589,940 B1 | 7/2003 | Raz et al. |
| 6,610,308 B1 | 8/2003 | Haensler |
| 6,610,661 B1 | 8/2003 | Carson et al. |
| 6,653,292 B1 | 11/2003 | Krieg et al. |
| 6,727,230 B1 | 4/2004 | Hutcherson et al. |
| 6,749,856 B1 | 6/2004 | Berzofsky et al. |
| 6,821,957 B2 | 11/2004 | Krieg et al. |
| 6,835,395 B1 | 12/2004 | Semple et al. |
| 6,852,705 B2 | 2/2005 | Audonnet et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,183,111 B2 | 2/2007 | Van Nest et al. |
| 7,223,741 B2 | 5/2007 | Krieg |
| 7,250,403 B2 | 7/2007 | Van Nest et al. |
| 7,255,868 B2 | 8/2007 | Fearon et al. |
| 7,271,156 B2 | 9/2007 | Krieg et al. |
| 7,279,555 B2 | 10/2007 | Peterson et al. |
| 7,303,881 B2 | 12/2007 | Huang et al. |
| 7,354,711 B2 | 4/2008 | Macfarlane |
| 7,354,909 B2 | 4/2008 | Klinman et al. |
| 7,402,572 B2 | 7/2008 | Krieg et al. |
| 7,410,975 B2 | 8/2008 | Lipford et al. |
| 7,485,627 B2 | 2/2009 | Raz et al. |
| 7,488,490 B2 | 2/2009 | Davis et al. |
| 7,517,861 B2 | 4/2009 | Krieg et al. |
| 7,521,063 B2 | 4/2009 | Klinman et al. |
| 7,524,828 B2 | 4/2009 | Krieg et al. |

(Continued)

FOREIGN PATENT DOCUMENTS

| | | |
|---|---|---|
| EP | 0 302 758 A1 | 2/1989 |
| EP | 0 468 520 A2 | 1/1992 |
| EP | 1 187 629 A2 | 10/2000 |
| WO | WO 95/03407 A2 | 2/1995 |
| WO | WO 96/02555 A1 | 2/1996 |
| WO | WO 98/55495 A2 | 12/1998 |
| WO | WO 99/56755 A1 | 11/1999 |
| WO | WO 99/63975 A2 | 12/1999 |
| WO | WO 00/06588 A1 | 2/2000 |
| WO | WO 00/14217 A3 | 3/2000 |

(Continued)

OTHER PUBLICATIONS

Mutwiri et al. Biological activity of immunostimulatory CpG DNA motifs in domestic animals. Veterinary Immunology and Immunopathology, 2003, vol. 91, 89-103.*
Krieg et al., CpG motif in bacterial DNA and their immune effects. Annu. Rev. Immunol., 2002, vol. 20, 709-760.*
Infante-Duarte et al., Thl/Th2 balance in infection. Springer Seminars in Immunopathology, 1999, 21: 317-338.*

(Continued)

*Primary Examiner*—Robert B Mondesi
*Assistant Examiner*—Nina A Archie
(74) *Attorney, Agent, or Firm*—Wolf, Greenfield & Sacks, P.C.; Gregg C. Benson

(57) ABSTRACT

The invention provides an immunostimulatory nucleic acid comprising CpG motifs, and methods of use thereof in stimulating immunity.

29 Claims, 14 Drawing Sheets

U.S. PATENT DOCUMENTS

| | | |
|---|---|---|
| 7,534,772 B2 | 5/2009 | Weiner et al. |
| 7,566,703 B2 | 7/2009 | Krieg et al. |
| 7,569,553 B2 | 8/2009 | Kreig |
| 7,576,066 B2 | 8/2009 | Krieg |
| 7,585,847 B2 | 9/2009 | Bratzler et al. |
| 2001/0044416 A1 | 11/2001 | McCluskie et al. |
| 2002/0064515 A1 | 5/2002 | Krieg et al. |
| 2002/0065236 A1 | 5/2002 | Yew et al. |
| 2002/0091097 A1 | 7/2002 | Bratzler et al. |
| 2002/0142977 A1 | 10/2002 | Raz et al. |
| 2002/0151518 A1 | 10/2002 | Agrawal et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0168340 A1 | 11/2002 | Agrawal |
| 2002/0192184 A1 | 12/2002 | Carpentier et al. |
| 2002/0198165 A1 | 12/2002 | Bratzler et al. |
| 2003/0026782 A1 | 2/2003 | Krieg et al. |
| 2003/0026801 A1 | 2/2003 | Weiner et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0087848 A1 | 5/2003 | Bratzler et al. |
| 2003/0091599 A1 | 5/2003 | Davis et al. |
| 2003/0100527 A1 | 5/2003 | Krieg et al. |
| 2003/0104523 A1 | 6/2003 | Bauer et al. |
| 2003/0119773 A1 | 6/2003 | Raz et al. |
| 2003/0125279 A1 | 7/2003 | Junghans et al. |
| 2003/0129605 A1 | 7/2003 | Yu et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0176389 A1 | 9/2003 | Raz et al. |
| 2003/0181406 A1 | 9/2003 | Schetter et al. |
| 2003/0191079 A1 | 10/2003 | Krieg et al. |
| 2003/0212026 A1 | 11/2003 | Krieg et al. |
| 2003/0212029 A1 | 11/2003 | Agrawal et al. |
| 2003/0224010 A1 | 12/2003 | Davis et al. |
| 2003/0225016 A1 | 12/2003 | Fearon et al. |
| 2003/0232074 A1 | 12/2003 | Lipford et al. |
| 2003/0232443 A1 | 12/2003 | Bennett et al. |
| 2003/0232856 A1 | 12/2003 | Macfarlane |
| 2004/0006010 A1 | 1/2004 | Carson et al. |
| 2004/0006034 A1 | 1/2004 | Raz et al. |
| 2004/0009949 A1 | 1/2004 | Krieg |
| 2004/0030118 A1 | 2/2004 | Wagner et al. |
| 2004/0038922 A1 | 2/2004 | Haensler et al. |
| 2004/0047869 A1 | 3/2004 | Garcon et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0076905 A1 | 4/2004 | Yagihashi et al. |
| 2004/0087534 A1 | 5/2004 | Krieg et al. |
| 2004/0087538 A1 | 5/2004 | Krieg et al. |
| 2004/0092468 A1 | 5/2004 | Schwartz et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0234960 A1 | 11/2004 | Olek et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0004144 A1 | 1/2005 | Carson et al. |
| 2005/0009774 A1 | 1/2005 | Krieg et al. |
| 2005/0013812 A1 | 1/2005 | Dow et al. |
| 2005/0019340 A1 | 1/2005 | Garcon et al. |
| 2005/0026861 A1 | 2/2005 | Kandimalla et al. |
| 2005/0031638 A1 | 2/2005 | Dalemans et al. |
| 2005/0032734 A1 | 2/2005 | Krieg |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0038239 A1 | 2/2005 | Catchpole |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0064401 A1 | 3/2005 | Olek et al. |
| 2005/0070491 A1 | 3/2005 | Krieg et al. |
| 2005/0075302 A1 | 4/2005 | Hutcherson et al. |
| 2005/0079152 A1 | 4/2005 | Bot et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0159351 A1 | 7/2005 | Grate et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0209184 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |

| | | | |
|---|---|---|---|
| 2006/0089326 A1 | 4/2006 | Krieg et al. | |
| 2006/0094683 A1 | 5/2006 | Krieg et al. | |
| 2006/0140875 A1 | 6/2006 | Krieg et al. | |
| 2006/0154890 A1 | 7/2006 | Bratzler et al. | |
| 2006/0172966 A1 | 8/2006 | Lipford et al. | |
| 2006/0188913 A1 | 8/2006 | Krieg et al. | |
| 2006/0211639 A1 | 9/2006 | Bratzler et al. | |
| 2006/0211644 A1 | 9/2006 | Krieg et al. | |
| 2006/0229271 A1 | 10/2006 | Krieg et al. | |
| 2006/0241076 A1 | 10/2006 | Uhlmann et al. | |
| 2006/0246035 A1 | 11/2006 | Ahluwalia et al. | |
| 2006/0286070 A1 | 12/2006 | Hartmann et al. | |
| 2006/0287263 A1 | 12/2006 | Davis et al. | |
| 2007/0009482 A9 | 1/2007 | Krieg et al. | |
| 2007/0010470 A9 | 1/2007 | Krieg et al. | |
| 2007/0037767 A1 | 2/2007 | Bratzler et al. | |
| 2007/0065467 A1 | 3/2007 | Krieg et al. | |
| 2007/0066550 A1 | 3/2007 | Diener et al. | |
| 2007/0066553 A1 | 3/2007 | Krieg et al. | |
| 2007/0066554 A1 | 3/2007 | Krieg et al. | |
| 2007/0078104 A1 | 4/2007 | Krieg et al. | |
| 2007/0129320 A9 | 6/2007 | Davis et al. | |
| 2007/0142315 A1 | 6/2007 | Forsbach et al. | |
| 2007/0184465 A1 | 8/2007 | Wagner et al. | |
| 2007/0202128 A1 | 8/2007 | Krieg et al. | |
| 2007/0224210 A1 | 9/2007 | Krieg et al. | |
| 2007/0232622 A1 | 10/2007 | Lipford et al. | |
| 2008/0009455 A9 | 1/2008 | Krieg et al. | |
| 2008/0026011 A1 | 1/2008 | Krieg et al. | |
| 2008/0031936 A1 | 2/2008 | Krieg et al. | |
| 2008/0045473 A1 | 2/2008 | Uhlmann et al. | |
| 2008/0113929 A1 | 5/2008 | Lipford et al. | |
| 2008/0146488 A1 | 6/2008 | Wettstein et al. | |
| 2008/0226649 A1 | 9/2008 | Schetter et al. | |
| 2009/0017021 A1 | 1/2009 | Davis et al. | |
| 2009/0060927 A1 | 3/2009 | Wagner et al. | |
| 2009/0074851 A1 | 3/2009 | Bachmann et al. | |
| 2009/0137519 A1 | 5/2009 | Krieg et al. | |
| 2009/0142362 A1 | 6/2009 | Krieg et al. | |
| 2009/0155212 A1 | 6/2009 | Bratzler et al. | |
| 2009/0155307 A1 | 6/2009 | Davis et al. | |
| 2009/0191188 A1 | 7/2009 | Krieg et al. | |
| 2009/0202575 A1 | 8/2009 | Krieg et al. | |

FOREIGN PATENT DOCUMENTS

| | | |
|---|---|---|
| WO | WO 00/15256 A2 | 3/2000 |
| WO | WO 00/54803 A2 | 9/2000 |
| WO | WO 00/61151 A2 | 10/2000 |
| WO | WO 00/67023 A1 | 11/2000 |
| WO | WO 00/67787 A2 | 11/2000 |
| WO | WO 01/22972 A2 | 4/2001 |
| WO | WO 01/35991 A2 | 5/2001 |
| WO | WO 01/45750 A1 | 6/2001 |
| WO | WO 01/54720 A1 | 8/2001 |
| WO | WO 01/92565 A2 | 12/2001 |
| WO | WO 02/00926 A2 | 1/2002 |
| WO | WO 02/18632 A2 | 3/2002 |
| WO | WO 02/28428 A2 | 4/2002 |
| WO | WO 02/069369 A2 | 9/2002 |
| WO | WO 03/094963 A2 | 11/2003 |
| WO | WO 2004/007743 A2 | 1/2004 |
| WO | WO 2004/012669 A2 | 2/2004 |
| WO | WO 2004/016805 A2 | 2/2004 |
| WO | WO 2004/026888 A2 | 4/2004 |
| WO | WO 2004/039829 A2 | 5/2004 |
| WO | WO 2004/087203 A2 | 10/2004 |
| WO | WO 2004/094671 A2 | 11/2004 |
| WO | WO 2005/004910 A2 | 1/2005 |
| WO | WO 2005/023289 A1 | 3/2005 |
| WO | WO 2005/111057 A3 | 11/2005 |
| WO | WO 2006/080946 A2 | 8/2006 |
| WO | WO 2007/031877 A2 | 3/2007 |
| WO | WO 2007/038720 A2 | 4/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Aoki et al. Use of cytokines in infection. Expert Opin. Emerg. Drugs, 2004, vol. 9, No. 2, 223-236.*

Bohn et al., Ambiguous role of interleukin-12 in Yersinia enterocolitica infection in susceptible and resistant mouse strains Infect. Immune., 1998, vol. 66, 2213-2220.*

Sakao et al. IL-18-deficient mice are resistant to endotoxin-induced liver injury but highly susceptible to endotoxin shock.*

Zaitseva et al. Interferon gamma and interleukin 6 modulate the susceptibility of macrophages to human immunodeficiency virus type 1 infection) Blood, 2000, vol. 96, 3109-3117.*

Masihi, K. Fighting infection using immunomodulatory agents. Expert Opin.Biol. Ther., 2001, vol. 1, No. 4, 641-653.*

Yu et al 2001 Biorganic & Medicinal Chemistry vol. 9 Issue 11 pp. 2803-2808.*

Sakao et al. IL-18-deficient mice are resistant to endotoxin-induced liver injury but highly susceptible to endotoxin shock, 2001.*

Agrawal et al., Medicinal chemistry and therapeutic potential of CpG DNA. Trends Mol Med. Mar. 2002;8(3):114-21.

Askew et al., CpG DNA induces maturation of dendritic cells with distinct effects on nascent and recycling MHC-II antigen-processing mechanisms. J Immunol. Dec. 15, 2000;165(12):6889-95.

AUF et al., Implication of macrophages in tumor rejection induced by CpG-oligodeoxynucleotides without antigen. Clin Cancer Res. Nov. 2001;7(11):3540-3.

Ballas et al., Divergent therapeutic and immunologic effects of oligodeoxynucleotides with distinct CpG motifs. J Immunol. Nov. 1, 2001;167(9):4878-86.

Baral et al., Immunostimulatory CpG oligonucleotides enhance the immune response of anti-idiotype vaccine that mimics carcinoembryonic antigen. Cancer Immunol Immunother. May 2003;52(5):317-27.

Bitton et al., Cancer vaccines: a critical review on clinical impact. Curr Opin Mol Ther. Feb. 2004;6(1):17-26. Abstract Only.

Blazar et al., Synthetic unmethylated cytosine-phosphate-guanosine oligodeoxynucleotides are potent stimulators of antileukemia responses in naive and bone marrow transplant recipients. Blood. Aug. 15, 2001;98(4):1217-25.

Broide et al., DNA-Based immunization for asthma. Int Arch Allergy Immunol. Feb.-Apr. 1999;118(2-4):453-6.

Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.

Carpentier et al., Successful treatment of intracranial gliomas in rat by oligodeoxynucleotides containing CpG motifs. Clin Cancer Res. Jun. 2000;6(6):2469-73.

Carpentier et al., Oligodeoxynucleotides containing CpG motifs can induce rejection of a neuroblastoma in mice. Cancer Res. Nov. 1, 1999;59(21):5429-32.

Chan et al., CpG-A and CpG-B oligodeoxynucleotides differentially affect the cytokine profile, chemokine receptor expression and T-cell priming function of human plasmacytoid dendritic cells. Blood. 2002;100:50b. Abstract #3666.

Chatterjee et al., Idiotypic antibody immunotherapy of cancer. Cancer Immunol Immunother. Feb. 1994;38(2):75-82.

Choi et al., The level of protection against rotavirus shedding in mice following immunization with a chimeric VP6 protein is dependent on the route and the coadministered adjuvant. Vaccine. Mar. 15, 2002;20(13-14):1733-40.

Chu et al., CpG oligodeoxynucleotides act as adjuvants that switch on T helper 1 (Th 1) immunity. J Exp Med. Nov. 17, 1997;186(10):1623-31.

Cooper et al., Safety and immunogenicity of CPG 7909 injection as an adjuvant to Fluarix influenza vaccine. Vaccine. Aug. 13, 2004;22(23-24):3136-43.

Daftarian et al., Two distinct pathways of immuno-modulation improve potency of p53 immunization in rejecting established tumors. Cancer Res. Aug. 1, 2004;64(15):5407-14.

Da Vila et al., Generation of antitumor immunity by cytotoxic T lymphocyte epitope peptide vaccination, CpG-oligodeoxynucleotide adjuvant, and CTLA-4 blockade. Cancer Res. Jun. 15, 2003;63(12):3281-8.

Da Vila et al., Repeated administration of cytosine-phosphorothiolated guanine-containing oligonucleotides together with peptide/protein immunization results in enhanced CTL responses with anti-tumor activity. J Immunol. Jul. 1, 2000;165(1):539-47.

Da Vis et al., CpG ODN is safe and highly effective in humans as adjuvant to HBV vaccine: Preliminary results of Phase I trial with CpG ODN 7909. Third Annual Conference on Vaccine Res. 2000. Abstract s25, No. 47.

De Grujil et al., Cancer vaccine strategies get bigger and better. Nat Med. Oct. 1999;5(10):1124-5.

Donnelly et al., Cancer vaccine targets leukemia. Nat Med. Nov. 2003;9(11):1354-6.

Ezzell et al., Cancer "Vaccines": An idea whose time has come? J NIH Research. 1995;7:46-9.

Filion et al., Development of immunomodulatory six base-length non-CpG motif oligonucleotides for cancer vaccination. Vaccine. Jun. 23, 2004;22(19):2480-8.

Forni et al., Immunoprevention of cancer: is the time ripe? Cancer Res. May 15, 2000;60(10):2571-5.

Gallichan et al., Intranasal immunization with CpG oligodeoxynucleotides as an adjuvant dramatically increases IgA and protection against herpes simplex virus-2 in the genital tract. J Immunol. Mar. 1, 2001;166(5):3451-7.

Gao et al., Bacterial DNA and lipopolysaccharide induce synergistic production of TNF-alpha through a post-transcriptional mechanism. J Immunol. Jun. 1, 2001;166(11):6855-60.

Garbi et al., CpG motifs as proinflammatory factors render autochthonous tumors permissive for infiltration and destruction. J Immunol. May 15, 2004;172(10):5861-9.

Gouttefangeas et al., Problem solving for tumor immunotherapy. Nat Biotechnol. May 2000;18(5):491-2.

Grossmann et al., Avoiding tolerance against prostatic antigens with subdominant peptide epitopes. J Immunother. May-Jun. 2001;24(3):237-41.

Hafner et al., Antimetastatic effect of CpG DNA mediated by type I IFN. Cancer Res. Jul. 15, 2001;61(14):5523-8.

Hartmann et al., CpG DNA: a potent signal for growth, activation, and maturation of human dendritic cells. Proc Natl Acad Sci U S A. Aug. 3, 1999;96(16):9305-10.

Heeg et al., CpG DNA as a Th1 trigger. Int Arch Allergy Immunol. Feb. 2000;121(2):87-97.

Jain et al., Barriers to drug delivery in solid tumors. Scientific American. 1994; 271:58-65.

Jakob et al., Activation of cutaneous dendritic cells by CpG-containing oligodeoxynucleotides: a role for dendritic cells in the augmentation of Th1 responses by immunostimulatory DNA. J Immunol. Sep. 15, 1998;161(6):3042-9.

Jakob et al., Bacterial DNA and CpG-containing oligodeoxynucleotides activate cutaneous dendritic cells and induce IL-12 production: implications for the augmentation of Th1 responses. Int Arch Allergy Immunol. Feb.-Apr. 1999;118(2-4):457-61.

Juffermans et al., CpG oligodeoxynucleotides enhance host defense during murine tuberculosis. Infect Immun. Jan. 2002;70(1):147-52.

Kataoka et al., Antitumor activity of synthetic oligonucleotides with sequences from cDNA encoding proteins of Mycobacterium bovis BCG. Jpn J Cancer Res. Mar. 1992;83(3):244-7.

Kataoka et al., Immunotherapeutic potential in guinea-pig tumor model of deoxyribonucleic acid from Mycobacterium bovis BCG complexed with poly-L-lysine and carboxymethylcellulose. Jpn J Med Sci Biol. Oct. 1990;43(5):171-82.

Klinman et al., Immunotherapeutic applications of CpG-containing oligodeoxynucleotides. Drug News Perspect. Jun. 2000;13(5):289-96.

Klinman et al., Immune recognition of foreign DNA: a cure for bioterrorism? Immunity. Aug. 1999;11(2):123-9.

Krieg et al., Applications of immune stimulatory CpG DNA for antigen-specific and antigen-nonspecific cancer immunotherapy. Eur J Canc. Oct. 1999; 35/Supp14:S10. Abstract #14.

Krieg et al., Bacterial DNA or oligonucleotides containing CpG motifs protect mice from lethal L. monocytogenes challenge. 1996 Meeting on Molecular Approaches to the Control of Infectious Diseases. Cold Spring Harbor Laboratory, Sep. 9-13, 1996: 116.

Krieg et al., Enhancing vaccines with immune stimulatory CpG DNA. Curr Opin Mol Ther. Feb. 2001;3(1):15-24.

Krieg et al., Mechanisms and therapeutic applications of immune stimulatory CpG DNA. Pharmacol Ther. Nov. 1999;84(2):113-20.

Krieg et al., The CpG motif: Implications for clinical immunology. BioDrugs. Nov. 1, 1998;10(5):341-6.

Krieg, Immune effects and mechanisms of action of CpG motifs. Vaccine. Nov. 8, 2000;19(6):618-22.

Krieg, The role of CpG motifs in innate immunity. Curr Opin Immunol. Feb. 2000;12(1):35-43.

Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.

Lee et al., Immuno-stimulatory effects of bacterial-derived plasmids depend on the nature of the antigen in intramuscular DNA inoculations. Immunology. Jul. 1998;94(3):285-9.

Leitner et al., Nucleic acid for the treatment of cancer: genetic vaccines and DNA adjuvants. Curr Pharm Des. Nov. 2001;7(16):1641-67.

Liang et al., Activation of human B cells by phosphorothioate oligodeoxynucleotides. J Clin Invest. Sep. 1, 1996;98(5):1119-29.

Lipford et al., CpG-containing synthetic oligonucleotides promote B and cytotoxic T cell responses to protein antigen: a new class of vaccine adjuvants. Eur J Immunol. Sep. 1997;27(9):2340-4.

Liu et al., CpG ODN is an effective adjuvant in immunization with tumor antigen. J Invest Med. Sep. 7, 1997;45(7):333A.

Liu et al., Immunostimulatory CpG oligodeoxynucleotides enhance the immune response to vaccine strategies involving granulocyte-macrophage colony-stimulating factor. Blood. Nov. 15, 1998;92(10):3730-6.

Lonsdorf et al., Intratumor CpG-oligodeoxynucleotide injection induces protective antitumor T cell immunity. J Immunol. Oct. 15, 2003;171(8):3941-6.

MacFarlane et al., Unmethylated CpG-containing oligodeoxynucleotides inhibit apoptosis in WEHI 231 B lymphocytes induced by several agents: evidence for blockade of apoptosis at a distal signalling step. Immunology. Aug. 1997;91(4):586-93.

Manegold et al., Addition of PF-3512676 (CpG 7909) to a taxane/platinum regimen for first-line treatment of unresectable non-small cell lung cancer (NSCLC) improves objective response—Phase II clinical trial. Pfizer Poster. 2005. Abstract 1131.

McCluskie et al., CpG DNA is a potent enhancer of systemic and mucosal immune responses against hepatitis B surface antigen with intranasal administration to mice. J Immunol. Nov. 1, 1998;161(9):4463-6.

McCluskie et al., CpG DNA as mucosal adjuvant. Vaccine, 18: 231-237, 2000.

McCluskie et al., Oral, intrarectal and intranasal immunizations using CpG and non-CpG oligodeoxynucleotides as ajuvants. Vaccine. Oct. 15, 2000;19(4-5):413-22.

McCluskie et al., CpG DNA is an effective oral adjuvant to protein antigens in mice. Vaccine. Nov. 22, 2000;19(7-8):950-7.

McCluskie et al., The potential of oligodeoxynucleotides as mucosal and parenteral adjuvants. Vaccine. Mar. 21, 2001;19(17-19):2657-60.

Miconnet et al., CpG are efficient adjuvants for specific CTL induction against tumor antigen-derived peptide. J Immunol. Feb. 1, 2002;168(3):1212-8.

Milas et al., CpG oligodeoxynucleotide enhances tumor response to radiation. Cancer Res. Aug. 1, 2004;64(15):5074-7.

Mutwiri et al., Biological activity of immunostimulatory CpG DNA motifs in domestic animals. Vet Immunol Immunopathol. Jan. 30, 2003;91(2):89-103.

Mutwiri et al., Strategies for enhancing the immunostimulatory effects of CpG oligodeoxynucleotides. J Control Release. May 31, 2004;97(1):1-17.

Ninalga et al., CpG oligonucleotide therapy cures subcutaneous and orthotopic tumors and evokes protective immunity in murine bladder cancer. J Immunother. Jan.-Feb. 2005;28(1):20-7.

O'Hagan et al., Recent developments in adjuvants for vaccines against infectious diseases. Biomol Eng. Oct. 15, 2001;18(3):69-85. Abstract only.

Paul et al., Technology evaluation: CpG-7909, Coley. Curr Opin Mol Ther. Oct. 2003;5(5):553-9. Abstract Only.

Pavlick et al., Novel therapeutic agents under investigation for malignant melanoma. Expert Opin Investig Drugs. Sep. 2003;12(9):1545-58.

Pisetsky et al., The immunologic properties of DNA. J Immunol. Jan. 15, 1996;156(2):421-3.

Ray et al., Oral pretreatment of mice with immunostimulatory CpG DNA induces reduced susceptibility to *Listeria monocytogenes*. Experimental Biology 2001. Orlando, Florida, USA. Mar. 31-Apr. 4, 2001. Abstracts, part II. FASEB J. Mar. 8, 2001;15(5):A1007.

Revaz et al., The importance of mucosal immunity in defense against epithelial cancers. Curr Opin Immunol. Apr. 2005;17(2):175-9.

Rochlitz et al., Gene therapy of cancer. Swiss Med Wkly. Jan. 12, 2001;131(1-2):4-9.

Schneeberger et al., CpG motifs are efficient adjuvants for DNA cancer vaccines. J Invest Dermatol. Aug. 2004;123(2):371-9.

Speiser et al., Rapid and strong human CD8+ T cell responses to vaccination with peptide, IFA, and CpG oligodeoxynucleotide 7909. J Clin Invest. Mar. 2005;115(3):739-46.

Stern et al., Vaccination with tumor peptide in CpG adjuvant protects via IFN-gamma-dependent CD4 cell immunity. J Immunol. Jun. 15, 2002;168(12):6099-105.

Takeshita et al., Signal transduction pathways mediated by the interaction of CpG DNA with Toll-like receptor 9. Semin Immunol: Feb. 2004;16(1):17-22.

Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.

Tortora et al., Oral antisense that targets protein kinase A cooperates with taxol and inhibits tumor growth, angiogenesis, and growth factor production. Clin Cancer Res. Jun. 2000;6(6):2506-12.

Van Ojik et al., Phase I/II study with CpG 7909 as adjuvant to vaccination with MAGE-3 protein in patients with MAGE-3 positive tumors. Ann Oncol. 2003;13:157. Abstract 579O.

Verma et al., Gene therapy—promises, problems, and prospects. Nature. Sep. 18, 1997;389:239-42.

Vicari et al., Reversal of tumor-induced dendritic cell paralysis by CpG immunostimulatory oligonucleotide and anti-interleukin 10 receptor antibody. J Exp Med. Aug. 19, 2002;196(4):541-9.

Vile et al., Cancer gene therapy: hard lessons and new courses. Gene Ther. Jan. 2000;7(1):2-8.

Wagner et al., CpG motifs are efficient adjuvants for genetic vaccines to induce antigen-specific protective anti-tumor T cell responses. 2000;203:429. Abstract R46.

Wang et al., CpG oligodeoxynucleotides inhibit tumor growth and reverse the immunosuppression caused by the therapy with 5-fluorouracil in murine hepatoma. World J Gastroebterol. Feb. 28, 2005;11(8):1220-4.

Warren et al., CpG oligodeoxynucleotides enhance monoclonal antibody therapy of a murine lymphoma. Clin Lymphoma. Jun. 2000;1(1):57-61.

Weeratna et al., CpG ODN can re-direct the Th bias of established Th2 immune responses in adult and young mice. FEMS Immunol Med Microbiol. Dec. 2001;32(1):65-71.

Weigel et al., Dendritic cell (DC)/AML hybrid vaccine administered with CpG oligodeoxynucleotide adjuvant provides protective anti-tumor effects. Proceedings of the American Association for Cancer Research. Jul. 2003;44(2):394-5. Abstract #1992.

Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.

Weiner et al., The immunobiology and clinical potential of immunostimulatory CpG oligodeoxynucleotides. J Leukoc Biol. Oct. 2000;68(4):455-63.

Wernette et al., CpG oligodeoxynucleotides stimulate canine and feline immune cell proliferation. Vet Immunol Immunopathol. Jan. 15, 2002;84(3-4):223-36.

Wooldridge et al., CpG DNA and cancer immunotherapy: orchestrating the antitumor immune response. Curr Opin Oncol. Nov. 2003;15(6):440-5.

Press Release, Jan. 2007, "Coley Pharmaceutical Group Updates Hepatitis C Drug Development Strategy".

Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".

[No Author Listed] CpG 7909: PF 3512676, PF-3512676. Drugs R D. 2006;7(5):312-6.

[No Author Listed] CPG10101 HCV Toll-Receptor 9 Antagonist Phase II Study Results. 57th Annual Meeting of the American Association for the Study of Liver Diseases. Oct. 27-31, 2006. Boston, MA. 9 pages.

[No Author Listed] Mechanisms of Microbial Diseases, Third Edition. Schaechter et al., Editors. Lippencott, Williams & Wilkins, 1999. p. xv-xvi.

Agrawal et al., Antisense therapeutics: is it as simple as complementary base recognition? Mol Med Today. Feb. 2000;6(2):72-81.

Agrawal et al., Chapter 19: Pharmacokinetics and bioavailability of antisense oligonucleotides following oral and colorectal administrations in experimental animals. 1998: 525-43.

Ahluwalia et al., Immunostimulatory profiles from two classes of CpG ODN administered subcutaneously to healthy subjects. ICI FOCIS 2004. Poster.

Anitescu et al., Interleukin-10 functions in vitro and in vivo to inhibit bacterial DNA-induced secretion of interleukin-12. J Interferon Cytokine Res. Dec. 1997;17(12):781-8.

Ballas et al., Induction of NK activity in murine and human cells by CpG motifs in oligodeoxynucleotides and bacterial DNA. J Immunol. Sep. 1, 1996;157(5):1840-5.

Bauer et al., DNA activates human immune cells through a CpG sequence-dependent manner. Immunology. Aug. 1999;97(4):699-705.

Bauer et al., Human TLR9 confers responsiveness to bacterial DNA via species-specific CpG motif recognition. Proc Natl Acad Sci U S A. Jul. 31, 2001;98(16):9237-42.

Bibby, Orthotopic models of cancer for preclinical drug evaluation: advantages and disadvantages. Eur J Cancer. Apr. 2004;40(6):852-7.

Boggs et al., Characterization and modulation of immune stimulation by modified oligonucleotides. Antisense Nucleic Acid Drug Dev. Oct. 1997;7(5):461-71.

Brazolot Millan et al., CpG DNA can induce strong Th1 humoral and cell-mediated immune responses against hepatitis B surface antigen in young mice. Proc Natl Acad Sci U S A. Dec. 22, 1998;95(26):15553-8.

Chace et al., Bacterial DNA-induced NK cell IFN-gamma production is dependent on macrophage secretion of IL-12. Clin Immunol Immunopathol. Aug. 1997;84(2):185-93.

Chu et al., CpG oligodeoxynucleotides down-regulate macrophage class II MHC antigen processing. J Immunol. Aug. 1, 1999;163(3):1188-94.

Connell et al., Anti-tumor activity of a CpG-containing oligodeoxynucleotide (ODN) in athymic mice. American Assn Cancer Reseach. Mar. 1999;40:Abstract #1982.

Cooper et al., CPG 7909 adjuvant improves hepatitis B virus vaccine seroprotection in antiretroviral-treated HIV-infected adults. AIDS. Sep. 23, 2005;19(14):1473-9.

Cooper et al., CPG 7909, an immunostimulatory TLR9 agonist oligodeoxynucleotide, as adjuvant to Engerix-B HBV vaccine in healthy adults: a double-blind phase I/II study. J Clin Immunol. Nov. 2004;24(6):693-701.

Cowdery et al., Bacterial DNA induces NK cells to produce IFN-gamma in vivo and increases the toxicity of lipopolysaccharides. J Immunol. Jun. 15, 1996;156(12):4570-5.

Davis, Use of CpG DNA for enhancing specific immune responses. Curr Top Microbiol Immunol. 2000;247:171-83.

Deng et al., CpG oligodeoxynucleotides stimulate protective innate immunity against pulmonary Klebsiella infection. J Immunol. Oct. 15, 2004;173(8):5148-55.

Diwan et al., Enhancement of immune responses by co-delivery of a CpG oligodeoxynucleotide and tetanus toxoid in biodegradable nanospheres. J Control Release. Dec. 13, 2002; 85(1-3):247-62.

Eckstein, Phosphorothioation of DNA in bacteria. Nat Chem Biol. Nov. 2007;3(11):689-90.

Goldberg et al., Beyond danger: unmethylated CpG dinucleotides and the immunopathogenesis of disease. Immunol Lett. Jul. 3, 2000;73(1):13-8.

Gramzinski et al., Interleukin-12- and gamma interferon-dependent protection against malaria conferred by CpG oligodeoxynucleotide in mice. Infect Immun. Mar. 2001;69(3):1643-9.

Gura et al., Antisense has growing pains. Science. Oct. 27, 1995;270(5236):575-7.

Halpern et al., Bacterial DNA induces murine interferon-gamma production by stimulation of interleukin-12 and tumor necrosis factor-alpha. Cell Immunol. Jan. 10, 1996;167(1):72-8.

Harandi et al., A protective role of locally administered immunostimulatory CpG oligodeoxynucleotide in a mouse model of genital herpes infection. J Virol. Jan. 2003;77(2):953-62.

Hartmann et al., CpG DNA and LPS induce distinct patterns of activation in human monocytes. Gene Ther. May 1999;6(5):893-903.

Hartmann et al., Delineation of a CpG phosphorothioate oligodeoxynucleotide for activating primate immune responses in vitro and in vivo. J Immunol. Feb. 1, 2000;164(3):1617-24.

Hartmann et al., Identification and functional analysis of tumor-infiltrating plasmacytoid dendritic cells in head and neck cancer. Cancer Res. Oct. 1, 2003;63(19):6478-87.

Hartmann et al., Mechanism and function of a newly identified CpG DNA motif in human primary B cells. J Immunol. Jan. 15, 2000;164(2):944-53.

Hartmann et al., Rational design of new CpG oligonucleotides that combine B cell activation with high IFN-alpha induction in plasmacytoid dendritic cells. Eur J Immunol. Jun. 2003;33(6):1633-41.

Hopkin et al., Curbing the CpGs of Bacterial and Viral DNA. BioMedNet. Jun. 25, 1999; Issue 57.

Horner et al., Immunostimulatory DNA is a potent mucosal adjuvant. Cell Immunol. Nov. 25, 1998;190(1):77-82.

Huang et al., Induction and regulation of Th1-inducing cytokines by bacterial DNA, lipopolysaccharide, and heat-inactivated bacteria. Infect Immun. Dec. 1999;67(12):6257-63.

Hunter et al., Biodegradable microspheres containing group B Streptococcus vaccine: immune response in mice. Am J Obstet Gynecol. Nov. 2001;185(5):1174-9.

Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.

Ishii et al., Antitumor therapy with bacterial DNA and toxin: complete regression of established tumor induced by liposomal CpG oligodeoxynucleotides plus interleukin-13 cytotoxin. Clin Cancer Res. Dec. 15, 2003;9(17):6516-22.

Jacobson et al., Early viral response and on treatment response to CpG 10101 (ACTILON™ ), in combination with pegylated interferon and/or ribavirin, in chronic HCV genotype 1 infected patients with prior relapse response. 57th Annual Meeting of American Association for the Study of the Liver Diseases (AASLD). Oct. 30, 2006, Boston, Massachusetts; Presented Abstract #96.

Jiang et al., Enhancing immunogenicity by CpG DNA. Curr Opin Mol Ther. Apr. 2003;5(2):180-5.

Jiang et al., Synthetic vaccines: the role of adjuvants in immune targeting. Curr Med Chem. Aug. 2003;10(15):1423-39.

Jones et al., Synthetic oligodeoxynucleotides containing CpG motifs enhance immunogenicity of a peptide malaria vaccine in Aotus monkeys. Vaccine. Aug. 6, 1999;17(23-24):3065-71.

Kandimalla et al., Secondary structures in CpG oligonucleotides affect immunostimulatory activity. Biochem Biophys Res Commun. Jul. 11, 2003;306(4):948-53.

Kelland, Of mice and men: values and liabilities of the athymic nude mouse model in anticancer drug development. Eur J Cancer. Apr. 2004;40(6):827-36.

Kim et al., Prognostic implication of aberrant promoter hypermethylation of CpG islands in adenocarcinoma of the lung. J Thorac Cardiovasc Surg. Nov. 2005;130(5):1378. Epub Oct. 13, 2005.

Kim et al., TLR9 agonist immunomodulator treatment of cutaneous T-cell lymphomas (CTCL) with CPG7909. Blood. Nov. 16, 2004;104(11):Abstract #743.

Kimura et al., Binding of oligoguanylate to scavenger receptors is required for oligonucleotides to augment NK cell activity and induce IFN. J Biochem (Tokyo). Nov. 1994;116(5):991-4.

Kline et al., DNA therapy for asthma. Curr Opin Allergy Clin Immunol. Feb. 2002;2(1):69-73.

Kline et al., Modulation of airway inflammation by CpG oligodeoxynucleotides in a murine model of asthma. J Immunol. Mar. 15, 1998;160(6):2555-9.

Kline et al., Treatment of established asthma in a murine model using CpG oligodeoxynucleotides. Am J Physiol Lung Cell Mol Physiol. Jul. 2002;283(1):L170-9.

Klinman et al., Contribution of CpG motifs to the immunogenicity of DNA vaccines. J Immunol. Apr. 15, 1997;158(8):3635-9.

Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.

Klinman et al., Immunotherapeutic uses of CpG oligodeoxynucleotides. Nat Rev Immunol. Apr. 2004;4(4):249-58.

Knipe et al., eds., Fields' Virology. 2001;1:1004-16.

Knipe et al., eds., Fields' Virology. 2001;1:1564.

Kovarik et al., Adjuvant effects of CpG oligodeoxynucleotides on responses against T-independent type 2 antigens. Immunology. Jan. 2001;102(1):67-76.

Kovarik et al., CpG oligodeoxynucleotides can circumvent the Th2 polarization of neonatal responses to vaccines but may fail to fully redirect Th2 responses established by neonatal priming. J Immunol. Feb. 1, 1999;162(3):1611-7.

Kranzer et al., CpG-oligodeoxynucleotides enhance T-cell receptor-triggered interferon-gamma production and up-regulation of CD69 via induction of antigen-presenting cell-derived interferon type I and interleukin-12. Immunology. Feb. 2000;99(2):170-8.

Krieg et al., A role for endogenous retroviral sequences in the regulation of lymphocyte activation. J Immunol. Oct. 15, 1989;143(8):2448-51.

Krieg et al., Causing a commotion in the blood: immunotherapy progresses from bacteria to bacterial DNA. Immunol Today. Oct. 2000;21(10):521-6.

Krieg et al., Chapter 17: Immune stimulation by oligonucleotides. in Antisense Drug Tech. 2001;1394:471-515.

Krieg et al., Chapter 8: Immune Stimulation by Oligonucleotides. In: Antisense Research and Application. Crooke, Ed. 1998:243-62.

Krieg et al., CpG DNA induces sustained IL-12 expression in vivo and resistance to Listeria monocytogenes challenge. J Immunol. Sep. 1, 1998;161(5):2428-34.

Krieg et al., CpG DNA: a novel immunomodulator. Trends Microbiol. Feb. 1999;7(2):64-5.

Krieg et al., CpG motifs in bacterial DNA trigger direct B-cell activation. Nature. Apr. 6, 1995;374(6522):546-9.

Krieg et al., Direct immunologic activities of CpG DNA and implications for gene therapy. J Gene Med. Jan.-Feb. 1999;1(1):56-63.

Krieg et al., How to exclude immunostimulatory and other nonantisense effects of antisense oligonucleotides. Manual of Antisense. 1999:79-89.

Krieg et al., Immune effects and therapeutic applications of CpG motifs in bacterial DNA. Immunopharmacology. Jul. 25, 2000;48(3):303-5.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Krieg et al., Infection. In: McGraw Hill Book. 1996:242-3.

Krieg et al., Leukocyte stimulation by oligodeoxynucleotides. In: Applied Antisense Oligonucleotide Technology. 1998:431-48.

Krieg et al., Lymphocyte activation by CpG dinucleotide motifs in prokaryotic DNA. Trends Microbiol. Feb. 1996;4(2):73-6.

Krieg et al., Lymphocyte activation mediated by oligodeoxynucleotides or DNA containing novel un-methylated CpG motifs. American College of Rheumatology 58th National Scientific Meeting. Minneapolis, Minnesota, Oct. 22, 1994. Abstracts. Arthritis Rheum. Sep. 1994;37(9 Suppl).

Krieg et al., Mechanism of action of CpG DNA. Curr Top Microbiol Immunol. 2000;247:1-21.

Krieg et al., Mechanisms and applications of immune stimulatory CpG oligodeoxynucleotides. Biochim Biophys Acta. Dec. 10, 1999;1489(1):107-16.

Krieg et al., Modification of antisense phosphodiester oligodeoxynucleotides by a 5' cholesteryl moiety increases cellular association and improves efficacy. Proc Natl Acad Sci U S A. Feb. 1, 1993;90(3):1048-52.

Krieg et al., Oligodeoxynucleotide modifications determine the magnitude of B cell stimulation by CpG motifs. Antisense Nucleic Acid Drug Dev. 1996 Summer;6(2):133-9.

Krieg et al., P-chirality-dependent immune activation by phosphorothioate CpG oligodeoxynucleotides. Oligonucleotides. 2003;13(6):491-9.

Krieg et al., Phosphorothioate oligodeoxynucleotides: antisense or anti-protein? Antisense Res Dev. 1995 Winter;5(4):241.

Krieg et al., Rescue of B cells from apoptosis by immune stimulatory CpG DNA. Springer Semin Immunopathol. 2000;22(1-2):55-61.

Krieg et al., Sequence motifs in adenoviral DNA block immune activation by stimulatory CpG motifs. Proc Natl Acad Sci U S A. Oct. 13, 1998;95(21):12631-6.

Krieg et al., The role of CpG dinucleotides in DNA vaccines. Trends Microbiol. Jan. 1998;6(1):23-7.

Krieg et al., Unmethylated CpG DNA protects mice from lethal listeria monocytogenes challenge. Vaccines. 1997; 97:77-9.

Krieg, An innate immune defense mechanism based on the recognition of CpG motifs in microbial DNA. J Lab Clin Med. Aug. 1996;128(2):128-33.

Krieg, Antiinfective applications of toll-like receptor 9 agonists. Proc Am Thorac Soc. Jul. 2007;4(3):289-94.

Krieg, Chapter 7: CpG oligonucleotides as immune adjuvants. Ernst Schering Research Found Workshop 2001; 30:105-18.

Krieg, CpG DNA: a pathogenic factor in systemic lupus erythematosus? J Clin Immunol. Nov. 1995;15(6):284-92.

Krieg, Development of TLR9 agonists for cancer therapy. J Clin Invest. May 2007;117(5):1184-94.

Krieg, Now I know my CpGs. Trends Microbiol. Jun. 2001;9(6):249-52.

Krieg, Signal transduction induced by immunostimulatory CpG DNA. Springer Semin Immunopathol. 2000;22(1-2):97-105.

Krieg, Therapeutic potential of Toll-like receptor 9 activation. Nat Rev Drug Discov. Jun. 2006;5(6):471-84.

Krieg, Toll-like receptor 9 (TLR9) agonists in the treatment of cancer. Oncogene. Jan. 7, 2008;27(2):161-7. Review.

Krug et al., Identification of CpG oligonucleotide sequences with high induction of IFN-alpha/beta in plasmacytoid dendritic cells. Eur J Immunol. Jul. 2001;31(7):2154-63.

Krug et al., Toll-like receptor expression reveals CpG DNA as a unique microbial stimulus for plasmacytoid dendritic cells which synergizes with CD40 ligand to induce high amounts of IL-12. Eur J Immunol. Oct. 2001;31(10):3026-37.

Kuramoto et al., Changes of host cell infiltration into Meth A fibrosarcoma tumor during the course of regression induced by injections of a BCG nucleic acid fraction. Int J Immunopharmacol. Jul. 1992;14(5):773-82.

Kuramoto et al., In situ infiltration of natural killer-like cells induced by intradermal injection of the nucleic acid fraction from BCG. Microbiol Immunol. 1989;33(11):929-40.

Kuramoto et al., Oligonucleotide sequences required for natural killer cell activation. Jpn J Cancer Res. Nov. 1992;83(11):1128-31.

Lee et al., Effects of a hexameric deoxyriboguanosine run conjugation into CpG oligodeoxynucleotides on their immunostimulatory potentials. J Immunol. Oct. 1, 2000;165(7):3631-9.

Li et al., Effective induction of CD8+ T-cell response using CpG oligodeoxynucleotides and HER-2/neu-derived peptide co-encapsulated in liposomes. Vaccine. Jul. 4, 2003;21(23):3319-29.

Li et al., Lymphoma immunotherapy with CpG oligodeoxynucleotides requires TLR9 either in the host or in the tumor itself. J Immunol. Aug. 15, 2007;179(4):2493-500.

Lipford et al., Bacterial DNA as immune cell activator. Trends Microbiol. Dec. 1998;6(12):496-500.

Lipford et al., Immunostimulatory DNA: sequence-dependent production of potentially harmful or useful cytokines. Eur J Immunol. Dec. 1997;27(12):3420-6.

Major et al., Chapter 34: Hepatitis C Viruses. In Fields' Virology. 2001;1:1127-61.

Marshall et al., Identification of a novel CpG DNA class and motif that optimally stimulate B cell and plasmacytoid dendritic cell functions. J Leukoc Biol. Jun. 2003;73(6):781-92.

Martin-Orozco et al., Enhancement of antigen-presenting cell surface molecules involved in cognate interactions by immunostimulatory DNA sequences. Int Immunol. Jul. 1999;11(7):1111-8.

Matson et al., Nonspecific suppression of [3H]thymidine incorporation by "control" oligonucleotides. Antisense Res Dev. 1992 Winter;2(4):325-30.

McCluskie et al., Enhancement of infectious disease vaccines through TLR9-dependent recognition of CpG DNA. Curr Top Microbiol Immunol. 2006;311:155-78.

McCluskie et al., Route and method of delivery of DNA vaccine influence immune responses in mice and non-human primates. Mol Med. May 1999;5(5):287-300.

McCluskie et al., The role of CpG in DNA vaccines. Springer Semin Immunopathol. 2000;22(1-2):125-32.

McCluskie et al., The use of CpG DNA as a mucosal vaccine adjuvant. Curr Opin Investig Drugs. Jan. 2001;2(1):35-9.

McHutchison et al., Early clinical results with CpG 10101, a new investigational antiviral TLR9 agonist being developed for treatment of subjects chronically infected with hepatitis C virus. 12th International Symposium on Viral Hepatitis and Liver Disease (ISVHLD). Jul. 3, 2006, Paris, France; Presented Abstract #O105.

McHutchison et al., Early viral response to CpG 10101, in combination with pegylated interferon and/or ribavirin, in chronic HCV genotype 1 infected patients with prior relapse response. 41st Annual Meeting of European Association for the Study of the Liver (EASL). Apr. 26-30, 2006, Vienna, Austria; Submitted Abstract.

McHutchison et al., Final results of a multi-center phase 1B, randomized, placebo-controlled, dose-escalation trial of CpG 10101 in patients with chronic hepatitis C virus. 41st Annual Meeting of European Association for the Study of the Liver (EASL). Apr. 30, 2006, Vienna, Austria; Presented Abstract #111.

Messina et al., The influence of DNA structure on the in vitro stimulation of murine lymphocytes by natural and synthetic polynucleotide antigens. Cell Immunol. Mar. 1993;147(1):148-57.

Moldoveanu et al., CpG DNA, a novel immune enhancer for systemic and mucosal immunization with influenza virus. Vaccine. Jul. 1998;16(11-12):1216-24.

Moseman et al., Human plasmacytoid dendritic cells activated by CpG oligodeoxynucleotides induce the generation of CD4+CD25+ regulatory T cells. J Immunol. Oct. 1, 2004;173(7):4433-42.

Norman et al., Liposome-mediated, nonviral gene transfer induces a systemic inflammatory response which can exacerbate pre-existing inflammation. Gene Ther. 2000;7:1425-30.

Payette et al., History of vaccines and positioning of current trends. Curr Drug Targets Infect Disord. Nov. 2001;1(3):241-7.

Peterson et al., Integrating pharmacology and in vivo cancer models in preclinical and clinical drug development. Eur J Cancer. Apr. 2004;40(6):837-44.

Pisetsky et al., Stimulation of in vitro proliferation of murine lymphocytes by synthetic oligodeoxynucleotides. Mol Biol Rep. Oct. 1993;18(3):217-21.

Pisetsky et al., The influence of base sequence on the immunological properties of defined oligonucleotides. Immunopharmacology. Nov. 1998;40(3):199-208.

Pisetsky, Immunologic consequences of nucleic acid therapy. Antisense Res Dev. 1995 Fall;5(3):219-25.

Pisetsky, The influence of base sequence on the immunostimulatory properties of DNA. Immunol Res. 1999;19(1):35-46.

Polanczyk et al., Immunostimulatory effects of DNA and CpG motifs. Cent Eur J of Immunol. 2000;25(3):160-6.

Rankin et al., CpG motif identification for veterinary and laboratory species demonstrates that sequence recognition is highly conserved. Antisense Nucleic Acid Drug Dev. Oct. 2001;11(5):333-40.

Readett et al., PF-3512676 (CPG7909) a Toll-like receptor 9 agonist—status of development for non-small cell lung cancer (NSCLC). Abstract PD3-1-6. Pfizer. Aug. 24, 2007. Poster.

Rees et al., CpG-DNA protects against a lethal orthopoxvirus infection in a murine model. Antiviral Res. Feb. 2005;65(2):87-95.

Rodriguez et al., Immunostimulatory PyNTTTTGT oligodeoxynucleotides: structural properties and refinement of the active motif. Oligonucleotides. 2006 Fall;16(3):275-85.

Roman et al., Immunostimulatory DNA sequences function as T helper-1-promoting adjuvants. Nat Med. Aug. 1997;3(8):849-54.

Rothenfusser et al., Recent advances in immunostimulatory CpG oligonucleotides. Curr Opin Mol Ther. Apr. 2003;5(2):98-106.

Rudginsky et al., Antitumor activity of cationic lipid complexed with immunostimulatory DNA. Mol Ther. Oct. 2001;4(4):347-55.

Rynkiewicz et al., Marked enhancement of antibody response to anthrax vaccine adsorbed with CPG 7909 in healthy volunteers. 45th Intersci. Conf. Antimicrob. Agents Chemother. Sep. 21-24, 2005; New Orleans, Louisiana. Meeting Poster.

Saijo et al., What are the reasons for negative phase III trials of molecular-target-based drugs? Cancer Sci. Oct. 2004;95(10):772-6.

Sandler et al., CpG oligonucleotides enhance the tumor antigen-specific immune response of a granulocyte macrophage colony-stimulating factor-based vaccine strategy in neuroblastoma. Cancer Res. Jan. 15, 2003;63(2):394-9.

Sato et al., Immunostimulatory DNA sequences necessary for effective intradermal gene immunization. Science. Jul. 19, 1996;273(5273):352-4.

Satoh et al., Morphological and immunohistochemical characteristics of the heterogeneous prostate-like glands (paraurethral gland) seen in female Brown-Norway rats. Toxicol Pathol. Mar.-Apr. 2001;29(2):237-41.

Scheller et al., CpG oligodeoxynucleotides activate HIV replication in latently infected human T cells. J Biol Chem. May 21, 2004;279(21):21897-902. Epub Mar. 11, 2004.

Scheule, The role of CpG motifs in immunostimulation and gene therapy. Adv Drug Deliv Rev. Nov. 15, 2000;44(2-3):119-34.

Schuh, Trials, tribulations, and trends in tumor modeling in mice. Toxicol Pathol. Mar.-Apr. 2004;32 Suppl 1:53-66.

Schwartz et al., Bacterial DNA or oligonucleotides containing unmethylated CpG motifs can minimize lipopolysaccharide-induced inflammation in the lower respiratory tract through an IL-12-dependent pathway. J Immunol. Jul. 1, 1999;163(1):224-31.

Schwarz et al., Role of Toll-like receptors in costimulating cytotoxic T cell responses. Eur J Immunol. Jun. 2003;33(6):1465-70.

Sester et al., Phosphorothioate backbone modification modulates macrophage activation by CpG DNA. J Immunol. Oct. 15, 2000;165(8):4165-73.

Sfondrini et al., Prevention of spontaneous mammary adenocarcinoma in HER-2/neu transgenic mice by foreign DNA. FASEB J. Nov. 2002;16(13):1749-54.

Shalaby, Development of oral vaccines to stimulate mucosal and systemic immunity: barriers and novel strategies. Clin Immunol Immunopathol. Feb. 1995;74(2):127-34.

Shao et al., CpG-containing oligodeoxynucleotide 1826 converts the weak uveitogenic rat interphotoreceptor retinoid-binding protein peptide 1181-1191 into a strong uveitogen. J Immunol. Nov. 1, 2003;171(9):4780-5.

Siegrist et al., Co-administration of CpG oligonucleotides enhances the late affinity maturation process of human anti-hepatitis B vaccine response. Vaccine. Dec. 16, 2004;23(5):615-22.

Sonehara et al., Hexamer palindromic oligonucleotides with 5'-CG-3' motif(s) induce production of interferon. J Interferon Cytokine Res. Oct. 1996;16(10):799-803.

Sparwasser et al., Bacterial DNA causes septic shock. Nature. Mar. 27, 1997;386(6623):336-7.

Sparwasser et al., Immunostimulatory CpG-oligodeoxynucleotides cause extramedullary murine hemopoiesis. J Immunol. Feb. 15, 1999;162(4):2368-74.

Sparwasser et al., Macrophages sense pathogens via DNA motifs: induction of tumor necrosis factor-alpha-mediated shock. Eur J Immunol. Jul. 1997;27(7):1671-9.

Stein et al., Non-antisense effects of oligodeoxynucleotides. Antisense Technology. 1997;Ch.11: 241-64.

Stein et al., Problems in interpretation of data derived from in vitro and in vivo use of antisense oligodeoxynucleotides. Antisense Res Dev. 1994 Summer;4(2):67-9.

Storey et al., Anti-sense phosphorothioate oligonucleotides have both specific and non-specific effects on cells containing human papillomavirus type 16. Nucleic Acids Res. Aug. 11, 1991;19(15):4109-14.

Stunz et al., Inhibitory oligonucleotides specifically block effects of stimulatory CpG oligonucleotides in B cells. Eur J Immunol. May 2002;32(5):1212-22.

Sun et al., Multiple effects of immunostimulatory DNA on T cells and the role of type I interferons. Springer Semin Immunopathol. 2000;22(1-2):77-84.

Sun et al., Type I interferon-mediated stimulation of T cells by CpG DNA. J Exp Med. Dec. 21, 1998;188(12):2335-42.

Threadgill et al., Mitogenic synthetic polynucleotides suppress the antibody response to a bacterial polysaccharide. Vaccine. Jan. 1998;16(1):76-82.

Tokunaga et al., Synthetic oligonucleotides with particular base sequences from the cDNA encoding proteins of Mycobacterium bovis BCG induce interferons and activate natural killer cells. Microbiol Immunol. 1992;36(1):55-66.

Tokunaga, Response of the organism to DNA—With a focus on immunostimulatory DNA. Kansen Ensho Meneki. 2001 Autumn; 31(3): 1-12. Japanese.

Tuetken et al., Ch. 6: Immune effects of bacterial DNA and their possible role in the pathogenesis of lupus. In: Lupus: Molecular and Cellular Pathogenesis, Kammar and Tsokos, Eds. Humana Press;1999:79-100.

Tzao et al., 5'CpG island hypermethylation and aberrant transcript splicing both contribute to the inactivation of the FHIT gene in resected non-small cell lung cancer. Eur J Cancer. Sep. 2004;40(14):2175-83.

Uhlmann et al., Recent advances in the development of immunostimulatory oligonucleotides. Curr Opin Drug Discov Devel. Mar. 2003;6(2):204-17.

Verthelyi et al., Human peripheral blood cells differentially recognize and respond to two distinct CPG motifs. J Immunol. Feb. 15, 2001;166(4):2372-7.

Vicari et al., Development of targeted toll-like receptor agonists for cancer therapy. PPO Focus. 2007; 1(2):1-15.

Vollmer et al., Characterization of three CpG oligodeoxynucleotide classes with distinct immunostimulatory activities. Eur J Immunol. Jan. 2004;34(1):251-62.

Vollmer et al., Highly immunostimulatory CpG-free oligodeoxynucleotides for activation of human leukocytes. Antisense Nucleic Acid Drug Dev. Jun. 2002;12(3):165-75.

Vollmer et al., Immunopharmacology of CpG oligodeoxynucleotides and ribavirin. Antimicrob Agents Chemother. Jun. 2004;48(6):2314-7.

Vollmer et al., Impact of modifications of heterocyclic bases in CpG dinucleotides on their immune-modulatory activity. J Leukoc Biol. Sep. 2004;76(3):585-93. Epub Jun. 24, 2004.

Vollmer et al., Modulation of CpG oligodeoxynucleotide-mediated immune stimulation by locked nucleic acid (LNA). Oligonucleotides. 2004 Spring;14(1):23-31.

Vollmer et al., Oligodeoxynucleotides lacking CpG dinucleotides mediate Toll-like receptor 9 dependent T helper type 2 biased immune stimulation. Immunology. Oct. 2004;113(2):212-23.

Vollmer, CpG motifs to modulate innate and adaptive immune responses. Int Rev Immunol. May-Aug, 2006;25(3-4):125-34. Abstract.

Vollmer, TLR9 in health and disease. Int Rev Immunol. May-Aug. 2006;25(3-4):155-81.

Wagner, Interactions between bacterial CpG-DNA and TLR9 bridge innate and adaptive immunity. Curr Opin Microbiol. Feb. 2002;5(1):62-9.

Walker et al., Immunostimulatory oligodeoxynucleotides promote protective immunity and provide systemic therapy for leishmaniasis via IL-12- and IFN-gamma-dependent mechanisms. Proc Natl Acad Sci U S A. Jun. 8, 1999;96(12):6970-5.

Wang et al., Phosphorothioation of DNA in bacteria by dnd genes. Nat Chem Biol. Nov. 2007;3(11):709-10. Epub Oct. 14, 2007. Supplementary information, 12 pages.

Wang et al., Synergy between CpG- or non-CpG DNA and specific antigen for B cell activation. Int Immunol. Feb. 2003;15(2):223-31.

Wang et al., T-cell-directed cancer vaccines: the melanoma model. Expert Opin Biol Ther. Mar. 2001;1(2):277-90.

Warren et al., APC stimulated by CpG oligodeoxynucleotide enhance activation of MHC class I-restricted T cells. J Immunol. Dec. 1, 2000;165(11):6244-51.

Weeratna et al., Reduction of antigen expression from DNA vaccines by coadministered oligodeoxynucleotides. Antisense Nucleic Acid Drug Dev. Aug. 1998;8(4):351-6.

Weeratna et al., CpG DNA induces stronger immune responses with less toxicity than other adjuvants. Vaccine. Mar. 6, 2000;18(17):1755-62.

Weigel et al., Comparative analysis of murine marrow-derived dendritic cells generated by Flt3L or GM-CSF/IL-4 and matured with immune stimulatory agents on the in vivo induction of antileukemia responses. Blood. Dec. 1, 2002;100(12):4169-76.

Weigel et al., CpG oligodeoxynucleotides potentiate the antitumor effects of chemotherapy or tumor resection in an orthotopic murine model of rhabdomyosarcoma. Clin Cancer Res. Aug. 1, 2003;9(8):3105-14.

Whitmore et al., LPD lipopolyplex initiates a potent cytokine response and inhibits tumor growth. Gene Ther. 1999;6:1867-75.

Whitmore et al., Systemic administration of LPD prepared with CpG oligonucleotides inhibits the growth of established pulmonary metastases by stimulating innate and acquired antitumor immune responses. Canc Immun Immunother. 2001;50:503-14.

Wohlleben et al., Atopic disorders: a vaccine around the corner? Trends Immunol. Nov. 2001;22(11):618-26.

Wooldridge et al., Immunostimulatory oligodeoxynucleotides containing CpG motifs enhance the efficacy of monoclonal antibody therapy of lymphoma. Blood. Apr. 15, 1997;89(8):2994-8.

Yamada et al., Effect of suppressive DNA on CpG-induced immune activation. J Immunol. Nov. 15, 2002;169(10):5590-4.

Yamamoto et al., [Commemorative lecture of receiving Imamura Memorial Prize. II. Mode of action of oligonucleotide fraction extracted from Mycobacterium bovis BCG] Kekkaku. Sep. 1994;69(9):571-4. Japanese.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.

Yamamoto et al., Synthetic oligonucleotides with certain palindromes stimulate interferon production of human peripheral blood lymphocytes in vitro. Jpn J Cancer Res. Aug. 1994;85(8):775-9.

Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.

Yi et al., CpG DNA rescue of murine B lymphoma cells from anti-IgM-induced growth arrest and programmed cell death is associated with increased expression of c-myc and bcl-xL. J Immunol. Dec. 1, 1996;157(11):4918-25.

Yi et al., CpG oligodeoxyribonucleotides rescue mature spleen B cells from spontaneous apoptosis and promote cell cycle entry. J Immunol. Jun. 15, 1998;160(12):5898-906.

Yi et al., IFN-gamma promotes IL-6 and IgM secretion in response to CpG motifs in bacterial DNA and oligodeoxynucleotides. J Immunol. Jan. 15, 1996;156(2):558-64.

Yi et al., Rapid immune activation by CpG motifs in bacterial DNA. Systemic induction of IL-6 transcription through an antioxidant-sensitive pathway. J Immunol. Dec. 15, 1996;157(12):5394-402.

Yi et al., Rapid induction of mitogen-activated protein kinases by immune stimulatory CpG DNA. J Immunol. Nov. 1, 1998;161(9):4493-7.

Yu et al., Potent CpG oligonucleotides containing phosphodiester linkages: in vitro and in vivo immunostimulatory properties. Biochem Biophys Res Commun. Sep. 13, 2002;297(1):83-90.

Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.

Zhao et al., Pattern and kinetics of cytokine production following administration of phosphorothioate oligonucleotides in mice. Antisense Nucleic Acid Drug Dev. Oct. 1997;7(5):495-502.

Zips et al., New anticancer agents: in vitro and in vivo evaluation. In Vivo. Jan.-Feb. 2005;19(1):1-7.

Baines et al, Immune-mediated tumor regression induced by CpG-containing oligodeoxynucleotides. Clin Cancer Res. Jul. 2003;9(7):2693-700.

Dittmer et al., Treatment of infectious diseases with immunostimulatory oligodeoxynucleotides containing CpG motifs. Curr Opin Microbiol. Oct. 2003;6(5):472-7. Review.

Kline et al., Ch. 26: DNA Immunomodulation of asthma. In Inflammatory Mechanisms in Allergic Diseases. Ed., Zeiman et al. Marcel Dekker, Inc. 2002;551-64.

Krieg et al., Identification of an oligodeoxynucleotide sequence motif that specifically inhibits phosphorylation by protein tyrosine kinases. Antisense Nucleic Acid Drug Dev. Apr. 1997;7(2):115-23.

Uhlmann, Oligonucleotide technologies: synthesis, production, regulations and applications. Nov. 29-30th, 2000, Hamburg, Germany. Expert Opin Biol Ther. Mar. 2001;1(2):319-28.

Verthelyi et al., *CpG oligodeoxynucleotides as vaccine adjuvants in primates*. J Immunol. Feb. 15, 2002;168(4):1659-63.

Vollmer et al., Identification of a new class of CpG oligonucleotides capable of inducing both B cell proliferation and high IFN-alpha secretion from PBMC of HCV chronic carriers. Antiv Ther. 2002;7:L115.

Senuma et al., Therapeutic effect of CpG motifs on the development of chronic graft-versus-host disease in mice. Cytokine. Oct. 7, 2002;20(1):23-9.

Luganini et al., Phosphorothioate-modified oligodeoxynucleotides inhibit human cytomegalovirus replication by blocking virus entry. Antimicrob Agents Chemother. Mar. 2008;52(3):1111-20. Epub Jan. 7, 2008.

\* cited by examiner

Fig. 11
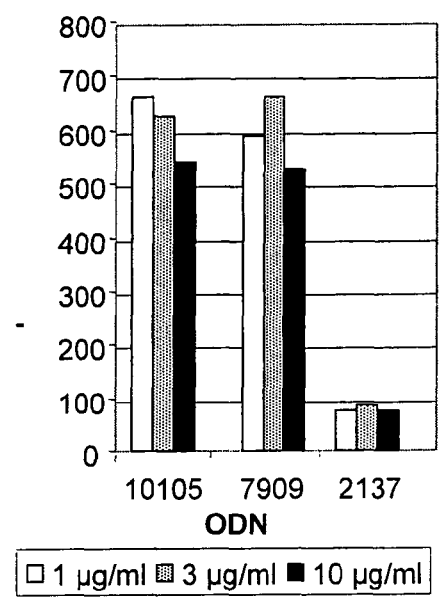
A. IL-10 conc. (pg/ml)
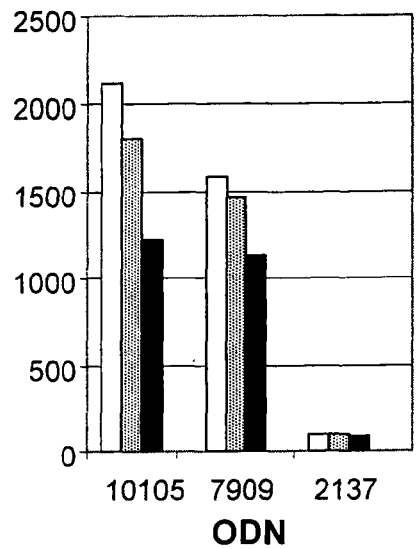
B. IL-12 conc. (pg/ml)
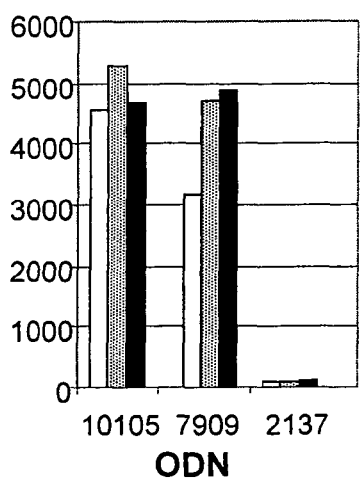
C. IL-6 conc. (pg/ml)
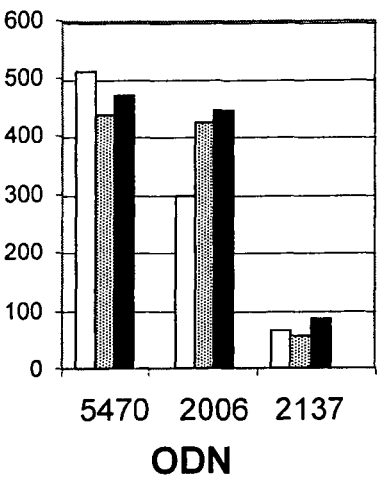
D. TNF-alpha conc. (pg/ml)

NUCLEIC ACID COMPOSITIONS FOR STIMULATING IMMUNE RESPONSES

RELATED APPLICATIONS

This application claims priority under 35 U.S.C. §119(e) to U.S. Provisional Application Ser. No. 60/394,164, entitled "NUCLEIC ACID COMPOSITIONS FOR STIMULATING IMMUNE RESPONSES", filed on Jul. 3, 2002, which is herein incorporated by reference in its entirety.

FIELD OF THE INVENTION

The present invention relates generally to immunostimulatory nucleic acids, compositions thereof and methods of using the immunostimulatory nucleic acids.

BACKGROUND OF THE INVENTION

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P., et al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10).

The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are essentially abolished if the CpG motif is methylated, changed to a GpC, or otherwise eliminated or altered (Krieg et al, 1995 Nature 374:546-549; Hartmann et al, 1999 Proc. Natl. Acad. Sci USA 96:9305-10). Phosphodiester CpG ODN can be formulated in lipids, alum, or other types of vehicles with depot properties or improved cell uptake in order to enhance the immune stimulatory effects (Yamamoto et al, 1994 Microbiol. Immunol. 38:831-836; Gramzinski et al, 1998 Mol. Med. 4:109-118).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci USA 96:9305-10; Liang, 1996 J. Clin. Invest. 98:1119-1129).

Several past investigators have looked at whether the nucleotide content of ODN may have effects independently of the sequence of the ODN. Interestingly, antisense ODN have been found to be generally enriched in the content of GG, CCC, CC, CAC, and CG sequences, while having reduced frequency of TT or TCC nucleotide sequences compared to what would be expected if base usage were random (Smetsers et al., 1996 Antisense Nucleic Acid Drug Develop. 6:63-67). This raised the possibility that the over-represented sequences may comprise preferred targeting elements for antisense oligonucleotides or visa versa. One reason to avoid the use of thymidine-rich ODN for antisense experiments is that degradation of the ODN by nucleases present in cells releases free thymidine which competes with $^3$H-thymidine which is frequently used in experiments to assess cell proliferation (Matson et al., 1992 Antisense Research and Development 2:325-330).

SUMMARY OF THE INVENTION

The invention is based in part on the surprising discovery that a new family of nucleic acids that induce higher levels of immune stimulation than previously known nucleic acids. This finding was surprising in part because more than 100 nucleic acid sequences were screened prior to discovering those disclosed herein.

The invention provides in one aspect, a composition comprising an immunostimulatory nucleic acid molecule comprising the nucleotide sequence of SEQ ID NO:1.

The invention further provides in another aspect, a method for stimulating an immune response in a subject in need thereof comprising administering to a subject an immunostimulatory nucleic acid molecule comprising the nucleotide sequence of SEQ ID NO:1, in an amount effective to stimulate an immune response.

Various embodiments of the invention apply equally to the aspects provided herein and some of these are recited below.

In one embodiment, the immunostimulatory nucleic acid molecule consists of the nucleotide sequence of SEQ ID NO:1.

In another embodiment, the composition further comprises an antigen. Alternatively, the subject to be treated is further administered an antigen. The antigen may be selected from the group consisting of a microbial antigen, a self antigen, a cancer antigen, and an allergen, but it is not so limited. In one embodiment, the microbial antigen is selected from the group consisting of a bacterial antigen, a viral antigen, a fungal antigen and a parasitic antigen. In another embodiment, the antigen is encoded by a nucleic acid vector. In a related embodiment, the nucleic acid vector is separate from the immunostimulatory nucleic acid. The antigen may be a peptide antigen.

In another embodiment, the composition further comprises an adjuvant, or the subject is further administered an adjuvant. The adjuvant may be a mucosal adjuvant, but it is not so limited.

In another embodiment, the composition further comprises a cytokine, or the subject is further administered a cytokine.

In still another embodiment, the composition further comprises a therapeutic agent selected from the group consisting of an anti-microbial agent, an anti-cancer agent, and an allergy/asthma medicament, or the subject is further administered a therapeutic agent selected from the same group. In a related embodiment, the anti-microbial agent is selected from the group consisting of an anti-bacterial agent, an anti-viral agent, an anti-fungal agent, and an anti-parasite agent. In another related embodiment, the anti-cancer agent is selected from the group consisting of a chemotherapeutic agent, a cancer vaccine, and an immunotherapeutic agent. In still another related embodiment, the allergy/asthma medicament is selected from the group consisting of PDE-4 inhibitor, bronchodilator/beta-2 agonist, K+ channel opener, VLA-4 antagonist, neurokin antagonist, TXA2 synthesis inhibitor, xanthanine, arachidonic acid antagonist, 5 lipoxygenase inhibitor, thromboxin A2 receptor antagonist, thromboxane A2 antagonist, inhibitor of 5-lipox activation protein, and protease inhibitor.

The immunostimulatory nucleic acid may in some embodiments have a nucleotide backbone which includes at least one backbone modification. In one embodiment, the backbone modification is a phosphorothioate modification. In another embodiment, the nucleotide backbone is chimeric. In one embodiment, the nucleotide backbone is entirely modified.

In one embodiment, the composition further comprises a pharmaceutically acceptable carrier.

In one embodiment, the immunostimulatory nucleic acid is free of methylated CpG dinucleotides. In another embodiment, the immunostimulatory nucleic acid includes at least four CpG motifs. In yet another embodiment, the immunostimulatory nucleic acid is T-rich. In a related embodiment, the immunostimulatory nucleic acid includes a poly-T sequence. In another embodiment, the immunostimulatory nucleic acid includes a poly-G sequence.

In certain embodiments, the immunostimulatory nucleic acid is formulated in a variety of ways. In one embodiment, the immunostimulatory nucleic acid is formulated for oral administration. The immunostimulatory nucleic acid may also be formulated as a nutritional supplement. In a related embodiment, the nutritional supplement is formulated as a capsule, a pill, or a sublingual tablet. In another embodiment, the immunostimulatory nucleic acid is formulated for local administration. The immunostimulatory nucleic acid may also be formulated for parenteral administration or it may be formulated in a sustained release device. The sustained release device may be a microparticle but it is not so limited. In another embodiment, the immunostimulatory nucleic acid is formulated for delivery to a mucosal surface. The mucosal surface may be selected from the group consisting of an oral, nasal, rectal, vaginal, and ocular surface, but is not so limited.

In one embodiment, the immunostimulatory nucleic acid stimulates a mucosal immune response. In another embodiment, the immunostimulatory nucleic acid stimulates a systemic immune response. In important embodiments, the immunostimulatory nucleic acid stimulates both a mucosal and systemic immune response. The immune response is an antigen-specific immune response, in some embodiments. In related embodiments, the immunostimulatory nucleic acid is provided in an amount effective to stimulate a mucosal immune response. In other embodiments, the immunostimulatory nucleic acid is provided in an amount effective to stimulate a systemic immune response. In still other embodiments, the immunostimulatory nucleic acid is provided in an amount effective to stimulate an innate immune response.

In various embodiments, the immunostimulatory nucleic acid is intended for treatment or prevention of a variety of diseases. Thus, in one embodiment, the immunostimulatory nucleic acid is provided in an amount effective to treat or prevent an infectious disease. In another embodiment, the immunostimulatory nucleic acid is provided in an amount effective to treat or prevent an allergy. In still another embodiment, the immunostimulatory nucleic acid is provided in an amount effective to treat or prevent asthma. In yet a further embodiment, the immunostimulatory nucleic acid is provided in an amount effective to treat or prevent a cancer.

In a related embodiment, the infectious disease is a herpes simplex virus infection. In another embodiment, the immunostimulatory nucleic acid is intended for administration to a subject that has or is at risk of developing an infection. The infection may be selected from the group consisting of a bacterial infection, a viral infection, a fungal infection, and a parasite infection. In one embodiment, the viral infection is selected from the group consisting of Human immunodeficiency viruses (HIV-1 and HIV-2), Human T lymphotrophic virus type I (HTLV-I), Human T lymphotrophic virus type II (HTLV-II), Herpes simplex virus type I (HSV-1), Herpes simplex virus type 2 (HSV-2), Human papilloma virus (multiple types), Hepatitis A virus, Hepatitis B virus, Hepatitis C and D viruses, Epstein-Barr virus (EBV), Cytomegalovirus and Molluscum contagiosum virus. In an important embodiment, the viral infection is a herpes simplex virus infection.

In other embodiments, the infection is an infection with a microbial species selected from the group consisting of *herpesviridae, retroviridae, orthomyroviridae, toxoplasma, haemophilus, campylobacter, clostridium, E. coli*, and *staphylococcus*. In related embodiments, the antigen to be administered to the subject or to be included in the composition is from one of the foregoing species.

In other embodiments, the immunostimulatory nucleic acid is intended from administration to a subject that has or is at risk of developing allergy, or a subject that has or is at risk of developing asthma, or a subject that has or is at risk of developing a cancer.

In embodiments relating to the treatment of a subject, the method may further comprise isolating an immune cell from the subject, contacting the immune cell with an effective amount to activate the immune cell of the immunostimulatory nucleic acid and re-administering the activated immune cell to the subject. In one embodiment, the immune cell is a leukocyte. In another embodiment, the immune cell is a dendritic cell. In another embodiment, the method further comprises contacting the immune cell with an antigen.

In important embodiments, the subject is a human. In other embodiments, the subject is selected from the group consisting of a dog, cat, horse, cow, pig, sheep, goat, chicken, monkey and fish.

Accordingly, the methods provided herein can be used on a subject that has or is at risk of developing an infectious disease and therefore the method is a method for treating or preventing the infectious disease. The methods can also be used on a subject that has or is at risk of developing asthma and the method is a method of treating or preventing asthma in the subject. The method can also be used on a subject that has or is at risk of developing allergy and the method is a method of treating or preventing allergy. And it can further be used on a subject that has or is at risk of developing a cancer and the method is a method of treating or preventing the cancer. In one embodiment, the cancer is selected from the group consisting of biliary tract cancer; bone cancer; brain and CNS cancer; breast cancer; cervical cancer; choriocarcinoma; colon cancer; connective tissue cancer; endometrial cancer; esophageal cancer; eye cancer; gastric cancer; Hodgkin's lymphoma; intraepithelial neoplasms; larynx cancer; lymphomas; liver cancer; lung cancer (e.g. small cell and non-small cell); melanoma; neuroblastomas; oral cavity cancer; ovarian cancer; pancreas cancer; prostate cancer; rectal cancer; sarcomas; skin cancer; testicular cancer; thyroid cancer; and renal cancer.

In yet another embodiment of the therapeutic or prophylactic methods provided herein, the method may further comprise administering an antibody specific for a cell surface antigen, and wherein the immune response results in antigen dependent cellular cytotoxicity (ADCC).

The invention provides in another aspect, a method for preventing disease in a subject, comprising administering to the subject an immunostimulatory nucleic acid on a regular basis to prevent disease in the subject, wherein the immunostimulatory nucleic acid has a nucleotide sequence comprising SEQ ID NO:1.

In yet another aspect, the invention provides a method for inducing an innate immune response, comprising administering to the subject an immunostimulatory nucleic acid in an amount effective for activating an innate immune response, wherein the immunostimulatory nucleic acid has a nucleotide sequence comprising SEQ ID NO:1.

In still another aspect, the invention provides a method for identifying an immunostimulatory nucleic acid comprising measuring a control level of activation of an immune cell population contacted with an immunostimulatory nucleic acid comprising a nucleotide sequence of SEQ ID NO:1, measuring a test level of activation of an immune cell population contacted with a test nucleic acid, and comparing the control level of activation to the test level of activation, wherein a test level that is equal to or above the control level is indicative of an immunostimulatory nucleic acid.

These and other aspects and embodiments of the invention will be described in greater detail herein.

BRIEF DESCRIPTION OF THE DRAWINGS

FIG. 11: Naïve BALB/c mouse splenocytes ($5 \times 10^6$/ml) were incubated with media (negative control) or different amounts of CpG ODN 7909, 10105 or control ODN 2137. Supernatants were harvested at 6 hr (for TNF-alpha, panel D), 24 hr (IL-12, panel B) or 48 hr (for IL-6, panel C, and IL-10, panel A).

DETAILED DESCRIPTION OF THE INVENTION

Figure 1:
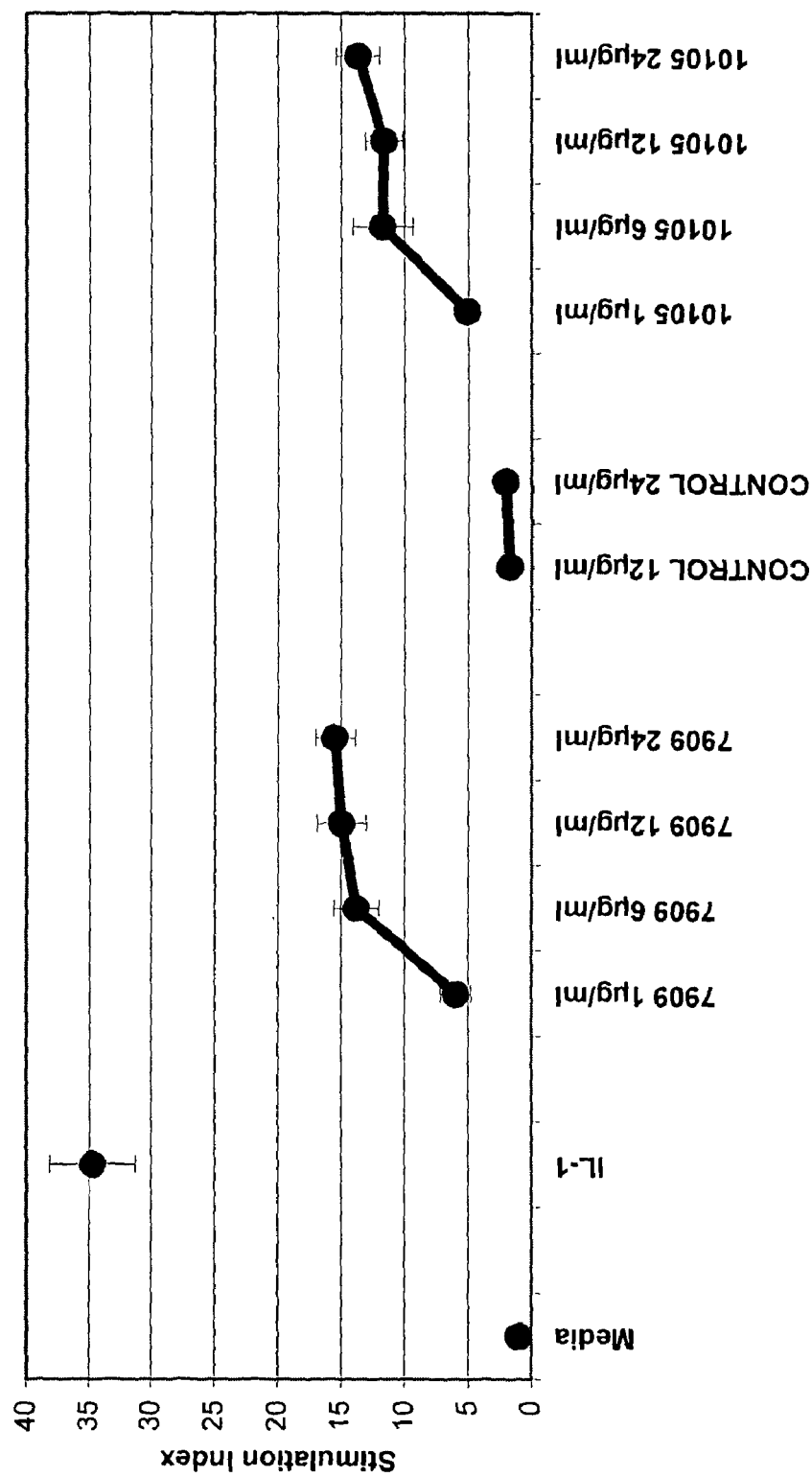
FIG. 1: TLR9 engagement by ODNs 7909 and 10105. A TLR9-expressing cell line was incubated with the indicated concentrations of ODNs as described in Materials and Methods. Shown is the mean Stimulation Index above media control for 4 independent experiments. IL-1 was used as a positive control for the reporter gene.

It was known in the prior art that CpG containing nucleic acids stimulate the immune system can thereby be used to treat cancer, infectious diseases, allergy, asthma and other disorders, and to help protect against opportunistic infections following cancer chemotherapies. The strong yet balanced, cellular and humoral immune responses that result from CpG stimulation reflect the body's own natural defense system against invading pathogens and cancerous cells. CpG sequences, while relatively rare in human DNA, are commonly found in the DNA of infectious organisms such as bacteria. The human immune system has apparently evolved to recognize CpG sequences as an early warning sign of infection, and to initiate an immediate and powerful immune response against invading pathogens without causing adverse reactions frequently seen with other immune stimulatory agents. Thus, CpG containing nucleic acids, relying on this innate immune defense mechanism, can utilize a unique and natural pathway for immune therapy.

The effects of CpG nucleic acids on immune modulation were discovered by the inventor of the instant patent application and have been described extensively in co-pending patent applications, such as U.S. patent application Ser. Nos: 08/386,063 filed on Feb. 2, 1995 (and related PCT US95/01570); 08/738,652 filed on Oct. 30, 1996; 08/960,774 filed on Oct. 30, 1997 (and related PCT/US97/19791, WO 98/18810); 09/191,170 filed on Nov. 13, 1998; 09/030,701 filed on Feb. 25, 1998 (and related PCT/US98/03678; 09/082,649 filed on May 20, 1998 (and related PCT/US98/10408); 09/325,193 filed on Jun. 3, 1999 (and related PCT/US98/04703); 09/286,098 filed on Apr. 2, 1999 (and related PCT/US99/07335); 09/306,281 filed on May 6, 1999 (and related PCT/US99/09863). The entire contents of each of these patents and patent applications is hereby incorporated by reference.

The invention is based, in part, on the unexpected discovery of a family of nucleic acids that is as immunostimulatory as previously reported CpG nucleic acids. This family of nucleic acids comprises the nucleotide sequence having the formula of 5' $X_1X_2X_3\ X_4X_5X_6\ X_7X_8X_9\ X_{10}X_{11}X_{12}\ X_{13}X_{14}X_{15}$ TTT TTT CGA 3' (SEQ ID NO:3)

wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, and $X_{15}$ are independently selected residues that may be selected from the group of nucleotides consisting of adenosine, guanosine, thymidine, and cytosine. In some embodiments, there may be no flanking residues. Such a nucleic acid would comprise a nucleotide sequence of 5' TTT TTT CGA 3' (SEQ ID NO:4).

In other embodiments, the nucleic acid may lack $X_1$; $X_1$ and $X_2$; $X_1$, $X_2$ and $X_3$; $X_1$, $X_2$, $X_3$ and $X_4$; or $X_1$, $X_2$, $X_3$, $X_4$ and $X_5$, $X_1$ through $X_6$, $X_1$ through $X_7$, $X_1$ through $X_8$, $X_1$ through $X_9$, $X_1$ through $X_{10}$, $X_1$ through $X_{11}$, $X_1$ through $X_{12}$, $X_1$ through $X_{13}$, $X_1$ through $X_{14}$, and $X_1$ through $X_{15}$.

In various embodiments, $X_1$ is a thymidine, and/or $X_2$ is cytosine, and/or $X_3$ is a guanosine, and/or $X_4$ is a thymidine, and/or $X_5$ is a cytosine, and/or $X_6$ is a guanosine, and/or $X_7$ is a thymidine, and/or $X_8$ is a thymidine, and/or $X_9$ is a thymidine, and/or $X_{10}$ is a thymidine, and/or $X_{11}$ is a guanosine, and/or $X_{12}$ is a thymidine, and/or $X_{13}$ is a cytosine, and/or $X_{14}$ is a guanosine, and/or $X_{15}$ is a thymidine. Those of ordinary skill in the art will be able to determine the sequence of the remaining nucleic acids belonging to this family.

The nucleic acids of this family are generally at least 9 nucleotides in length. In some embodiments, the nucleic acids are at least 10, at least 12, at least 15, at least 18, at least 20, at least 22, and at least 24 nucleotides in length. In a preferred embodiment, the nucleic acids are 24 nucleotides in length. In still further embodiments, the nucleic acids are more than 24 nucleotides in length. Examples include nucleic acids that are at least 50, at least 75, at least 100, at least 200, at least 500, at least 1000 nucleotides in length, or longer. Preferably, the nucleic acids are 9-100, and more preferably 24-100 nucleotides in length.

All the nucleic acids of this first family contain at least one CpG motif. These nucleic acids may contain two, three, four or more CpG motifs. The CpG motifs may be contiguous to each other, or alternatively, they may be spaced apart from each other at constant or random distances.

The nucleic acids of this family also contain an overrepresentation of thymidine nucleotides. These nucleic acids may contain at least 60%, at least 55%, or at least 50% thymidines.

The invention is further premised, in part, on the unexpected discovery of another family of nucleic acids that is as immunostimulatory as previously reported CpG nucleic acids. This family of nucleic acids comprises the nucleotide sequence having the formula of

5' TCG TCG TTT TGT CGT TTT T $X_1X_2\ X_3X_4X_5$ 3' (SEQ ID NO:5)

wherein $X_1$ through $X_5$ are independently selected residues that may be selected from the group of nucleotides consisting of adenosine, guanosine, thymidine, and cytosine. In some embodiments, there may be no flanking residues. As an example, the nucleic acid may comprise a nucleotide sequence of 5' TCG TCG TTT TGT CGT TTT T 3' (SEQ ID NO:6).

In other embodiments, the nucleic acid may lack $X_5$; $X_5$ and $X_4$; $X_5$, $X_4$ and $X_3$; $X_5$ through $X_2$; and $X_5$ through $X_1$.

In various embodiments, $X_1$ is a thymidine, and/or $X_2$ is thymidine, and/or $X_3$ is a cytosine, and/or $X_4$ is a guanosine, and/or $X_5$ is an adenine. Those of ordinary skill in the art will be able to determine the sequence of the remaining nucleic acids belonging to this family.

The nucleic acids of this family are generally at least 19 nucleotides in length. In some embodiments, the nucleic acids are at least 20, at least 22, and at least 24 nucleotides in length. In a preferred embodiment, the nucleic acids are 24 nucleotides in length. In still further embodiments, the nucleic acids are more than 24 nucleotides in length. Examples include nucleic acids that are at least 50, at least 75, at least 100, at least 200, at least 500, at least 1000 nucleotides in length, or longer. Preferably, the nucleic acids are 19-100, and more preferably 24-100 nucleotides in length.

All the nucleic acids of this second family contain at least three CpG motifs. These nucleic acids may contain four or more CpG motifs, depending upon the embodiment. The CpG motifs may be contiguous to each other, or alternatively, they may be spaced apart from each other at constant or random distances.

The nucleic acids of this family also contain an overrepresentation of thymidine nucleotides. These nucleic acids may contain at least 60%, at least 55%, or at least 50% thymidines.

In another aspect, the invention provides a nucleic acid comprising the nucleotide sequence of TCG TCG TTT TGT CGT TTT TTT CGA (SEQ ID NO:1). As described in greater detail in the Examples, this nucleic acid was identified only after screening a multitude of nucleic acids for those having similar or greater immunostimulatory activity than previously identified immunostimulatory nucleic acids. More specifically, the nucleic acids were compared to a nucleic acid having a nucleotide sequence of TCG TCG TTT TGT CGT TTT GTC GTT (SEQ ID NO:2) that was previously shown to be immunostimulatory. The nucleic acid comprising SEQ ID NO:1 was identified only after screening approximately 165 nucleic acids for those having immunostimulatory capacity similar to or greater than that of nucleic acids comprising SEQ ID NO:2. The difference in activity is surprising because there is 79% identity between SEQ ID NO:1 and SEQ ID NO:2 (i.e., five of the last 3' nucleotides differ between SEQ ID NO:1 and SEQ ID NO:2). It was unexpected that such a change in sequence would result in an increase in immunostimulation.

In yet other aspects of the invention, nucleic acids having the following nucleotide sequences are provided: 5' TCG TCG TTT TGT CGT TTT TTT CG 3' (SEQ ID NO:7);

```
5' TCG TCG TTT TGT CGT TTT TTT C 3';  (SEQ ID NO: 8)

5' TCG TCG TTT TGT CGT TTT TTT 3';    (SEQ ID NO: 9)

5' TCG TCG TTT TGT CGT TTT TT 3';     (SEQ ID NO: 10)

5' CG TCG TTT TGT CGT TTT TTT
CGA 3';                                (SEQ ID NO: 11)

5' G TCG TTT TGT CGT TTT TTT CGA 3';  (SEQ ID NO: 12)

5' TCG TTT TGT CGT TTT TTT CGA 3';    (SEQ ID NO: 13)

5' CG TTT TGT CGT TTT TTT CGA 3';     (SEQ ID NO: 14)

5' G TTT TGT CGT TTT TTT CGA 3';      (SEQ ID NO: 15)

5' TTT TGT CGT TTT TTT CGA 3';        (SEQ ID NO: 16)

5' TT TGT CGT TTT TTT CGA 3';         (SEQ ID NO: 17)

5' T TGT CGT TTT TTT CGA 3';          (SEQ ID NO: 18)

5' TGT CGT TTT TTT CGA 3';            (SEQ ID NO: 19)

5' GT CGT TTT TTT CGA 3';             (SEQ ID NO: 20)

5' T CGT TTT TTT CGA 3';              (SEQ ID NO: 21)

5' CGT TTT TTT CGA 3';                (SEQ ID NO: 22)

5' GT TTT TTT CGA 3';                 (SEQ ID NO: 23)

and

5' T TTT TTT CGA 3'.                  (SEQ ID NO: 24)
```

These immunostimulatory nucleic acids are capable of activating the innate immune system, and augmenting both humoral and cellular antigen specific responses when co-administered with an antigen, such as Hepatitis B surface antigen. The Examples provided herein demonstrate that these nucleic acids can stimulate human immune cells in vitro, and murine cells in vitro and in vivo. When compared to a sequence known to be a potent adjuvant, the nucleic acid of SEQ ID NO:1 is found to work as well or better as a vaccine adjuvant.

The CpG motifs of the nucleic acids described herein are preferably unmethylated. An unmethylated CpG motif is an unmethylated cytosine-guanine dinucleotide sequence (i.e. an unmethylated 5' cytosine followed by 3' guanosine and linked by a phosphate bond). All the nucleic acid described herein are immunostimulatory. In some embodiments of the invention, the CpG motifs are methylated. A methylated CpG motif is a methylated cytosine-guanine dinucleotide sequence (i.e., a methylated 5' cytosine followed by a 3' guanosine and linked by a phosphate bond).

A CpG nucleic acid is a nucleic acid that comprises the formula $$5' X_1 X_2 CGX_3 X_4 3'$$

wherein C is unmethylated, wherein $X_1X_2$ and $X_3X_4$ are nucleotides. In a related embodiment, the 5' $X_1 X_2CGX_3 X_4$ 3' sequence is a non-palindromic sequence. In certain embodiments, $X_1X_2$ are nucleotides selected from the group consisting of GpT, GpG, GpA, ApA, ApT, ApG, CpT, CpA, CpG, TpA, TpT, and TpG; and $X_3X_4$ are nucleotides selected from the group consisting of TpT, CpT, ApT, TpG, ApG, CpG, TpC, ApC, CpC, TpA, ApA, and CpA. In more particular embodiments, $X_1X_2$ are nucleotides selected from the group consisting of GpA and GpT; and $X_3X_4$ are TpT. In yet other embodiments, $X_1X_2$ are both purines and $X_3X_4$ are both pyrimidines. In another embodiment, $X_2$ is a T and $X_3$ is a pyrimidine. Examples of CpG nucleic acids are described in U.S. Non-Provisional patent application Ser. No. 09/669,187, filed Sep. 25, 2000, and in published PCT Patent Application PCT/US00/26383, having publication number WO01/22972.

The nucleic acids of the invention can further contain other immunostimulatory motifs such as poly T motifs, poly G motifs, TG motifs, poly A motifs, poly C motifs, and the like, provided that the core sequences of SEQ ID NO:4 and SEQ ID NO:6 are present. These immunostimulatory motifs are described in greater detail below or in U.S. Non-Provisional patent application Ser. No. 09/669,187, filed Sep. 25, 2000, and published PCT Patent Application PCT/US00/26383, having publication number WO01/22972

A T-rich nucleic acid is a nucleic acid which includes at least one poly T sequence and/or which has a nucleotide composition of greater than 25% T nucleotide residues. A nucleic acid having a poly-T sequence includes at least four Ts in a row, such as 5'TTTT3'. Preferably a T-rich nucleic acid includes more than one poly T sequence. In preferred embodiments the T-rich nucleic acid may have 2, 3, 4, etc poly T sequences. Other T-rich nucleic acids according to the invention have a nucleotide composition of greater than 25% T nucleotide residues, but do not necessarily include a poly T sequence. In these T-rich nucleic acids the T nucleotide resides may be separated from one another by other types of nucleotide residues, i.e., G, C, and A. In some embodiments the T-rich nucleic acids have a nucleotide composition of greater than 35%, 40%, 50%, 60%, 70%, 80%, 90%, and 99%, T nucleotide residues and every integer % in between. Preferably the T-rich nucleic acids have at least one poly T sequence and a nucleotide composition of greater than 25% T nucleotide residues.

Poly G nucleic acids preferably are nucleic acids having the following formulas:

$$5' X_1X_2GGGX_3X_4 3'$$

wherein $X_1$, $X_2$, $X_3$, and $X_4$ are nucleotides. In preferred embodiments at least one of $X_3$ and $X_4$ are a G. In other embodiments both of $X_3$ and $X_4$ are a G. In yet other embodiments the preferred formula is 5' GGGNGGG 3' (SEQ ID NO:28) or 5' GGGNGGGNGGG 3' (SEQ ID NO:29), wherein N represents between 0 and 20 nucleotides.

A C-rich nucleic acid is a nucleic acid molecule having at least one or preferably at least two poly-C regions or which is composed of at least 50% C nucleotides. A poly-C region is at least four C residues in a row. Thus a poly-C region is encompassed by the formula 5'CCCC 3'. In some embodiments it is preferred that the poly-C region have the formula 5'CCCCCC 3'. Other C-rich nucleic acids according to the invention have a nucleotide composition of greater than 50% C nucleotide residues, but do not necessarily include a poly C sequence. In these C-rich nucleic acids the C nucleotide residues may be separated from one another by other types of nucleotide residues, i.e., G, T, and A. In some embodiments the C-rich nucleic acids have a nucleotide composition of greater than 60%, 70%, 80%, 90%, and 99%, C nucleotide residues and every integer % in between. Preferably the C-rich nucleic acids have at least one poly C sequence and a nucleotide composition of greater than 50% C nucleotide residues, and in some embodiments are also T-rich.

The immunostimulatory nucleic acids can be double-stranded or single-stranded. Generally, double-stranded molecules are more stable in vivo, while single-stranded molecules have increased immune activity. Thus in some aspects of the invention it is preferred that the nucleic acid be single stranded and in other aspects it is preferred that the nucleic acid be double stranded.

The terms "nucleic acid" and "oligonucleotide" are used interchangeably herein to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g., genomic or cDNA), but are preferably synthetic (e.g. produced by nucleic acid synthesis).

The immunostimulatory oligonucleotides of the instant invention can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

For example, the oligonucleotides may comprise one or more modifications and wherein each modification is independently selected from:

a) the replacement of a phosphodiester internucleoside bridge located at the 3' and/or the 5' end of a nucleoside by a modified internucleoside bridge, b) the replacement of phosphodiester bridge located at the 3' and/or the 5' end of a nucleoside by a dephospho bridge, c) the replacement of a sugar phosphate unit from the sugar phosphate backbone by another unit, d) the replacement of a β-D-ribose unit by a modified sugar unit, and e) the replacement of a natural nucleoside base by a modified nucleoside base.

More detailed examples for the chemical modification of an oligonucleotide are as follows.

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, thymidine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art. In all of the foregoing embodiments, an X residue can also be a non-naturally occurring nucleotide, or a nucleotide analog, such as those described herein.

A modified base is any base which is chemically distinct from the naturally occurring bases typically found in DNA and RNA such as T, C, G, A, and U, but which share basic chemical structures with these naturally occurring bases. The modified nucleoside base may be, for example, selected from hypoxanthine, uracil, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleosides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleoside bases. This list is meant to be exemplary and is not to be interpreted to be limiting.

In particular formulas described herein a set of modified bases is defined. For instance the letter Y is used to refer to a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer). The letter Z is used to refer to guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

The oligonucleotides may include modified internucleotide linkages, such as those described in a or b above. These modified linkages may be partially resistant to degradation (e.g., are stabilized). A "stabilized nucleic acid molecule" shall mean a nucleic acid molecule that is relatively resistant to in vivo degradation (e.g. via an exo- or endo-nuclease). Stabilization can be a function of length or secondary structure. Nucleic acids that are tens to hundreds of kilobases long are relatively resistant to in vivo degradation. For shorter nucleic acids, secondary structure can stabilize and increase their effect. For example, if the 3' end of an nucleic acid has self-complementarity to an upstream region, so that it can fold back and form a sort of stem loop structure, then the nucleic acid becomes stabilized and therefore exhibits more activity.

Nucleic acid stabilization can also be accomplished via phosphate backbone modifications. Oligonucleotides having phosphorothioate linkages, in some embodiments, may provide maximal activity and protect the oligonucleotide from degradation by intracellular exo- and endo-nucleases.

It has been demonstrated that modification of the nucleic acid backbone provides enhanced activity of nucleic acids when administered in vivo. Constructs having phosphorothioate linkages provide maximal activity and protect the nucleic acid from degradation by intracellular exo- and endo-nucleases. Other modified nucleic acids include phosphodiester modified nucleic acids, combinations of phosphodiester and phosphorothioate nucleic acid, methylphosphonate, methylphosphorothioate, phosphorodithioate, p-ethoxy, and combinations thereof. Each of these combinations and their particular effects on immune cells is discussed in more detail with respect to CpG nucleic acids in PCT Published Patent Applications PCT/US95/01570 (WO 96/02555) and PCT/US97/19791 (WO 98/18810) and in U.S. Pat. No. 6,194,388 B1 issued Feb. 27, 2001 and U.S. Pat. No. 6,239,116 B1 issued May 29, 2001, the entire contents of which are hereby incorporated by reference. It is believed that these modified nucleic acids may show more stimulatory activity due to enhanced nuclease resistance, increased cellular uptake, increased protein binding, and/or altered intracellular localization.

Other stabilized nucleic acids include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The oligonucleotides may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'-3'-linkage may be a phosphodiester, phosphorothioate or any other modified internucleoside bridge. Methods for accomplishing such linkages are known in the art. For instance, such linkages have been described in Seliger, H. et al., Oligonucleotide analogs with terminal 3'-3'- and 5'-5'-internucleotidic linkages as antisense inhibitors of viral gene expression, Nucleosides & Nucleotides (1991), 10(1-3), 469-77 and Jiang, et al., Pseudocyclic oligonucleotides: in vitro and in vivo properties, Bioorganic & Medicinal Chemistry (1999), 7(12), 2727-2735.

Additionally, 3'3'-linked ODNs where the linkage between the 3'-terminal nucleosides is not a phosphodiester, phosphorothioate or other modified bridge, can be prepared using an additional spacer, such as tri- or tetra-ethyleneglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, $NR^1R^2$-phosphoramidate, boranophosphate, α-hydroxybenzyl phosphonate, phosphate-$(C_1$-$C_{21})$—O-alkyl ester, phosphate-$[(C_6$-$C_{12})$aryl-$(C_1$-$C_{12})$—O-alkyl]ester, $(C_1$-$C_8)$alkylphosphonate and/or $(C_6$-$C_{12})$arylphosphonate bridges, $(C_7$-$C_{12})$-α-hydroxymethyl-aryl (e.g., disclosed in WO 95/01363), wherein $(C_6$-$C_{12})$aryl, $(C_6$-$C_{20})$aryl and $(C_6$-$C_{14})$aryl are optionally substituted by halogen, alkyl, alkoxy, nitro, cyano, and where $R^1$ and $R^2$ are, independently of each other, hydrogen, $(C_1$-$C_8)$-alkyl, $(C_6$-$C_{20})$-aryl, $(C_6$-$C_{14})$-aryl-$(C_1$-$C_8)$-alkyl, preferably hydrogen, $(C_1$-$C_8)$-alkyl, preferably $(C_1$-$C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

The compositions of the invention may optionally be have chimeric backbones. As used herein, a chimeric backbone is one that comprises more than one type of linkage. In one embodiment, the chimeric backbone can be represented by the formula: 5' $Y_1N_1ZN_2Y_2$ 3'. $Y_1$ and $Y_2$ are nucleic acid molecules having between 1 and 10 nucleotides. $Y_1$ and $Y_2$ each include at least one modified internucleotide linkage. Since at least 2 nucleotides of the chimeric oligonucleotides include backbone modifications these nucleic acids are an example of one type of "stabilized immunostimulatory nucleic acids."

With respect to the chimeric oligonucleotides, $Y_1$ and $Y_2$ are considered independent of one another. This means that each of $Y_1$ and $Y_2$ may or may not have different sequences and different backbone linkages from one anther in the same molecule. In some embodiments $Y_1$ and/or $Y_2$ have between 3 and 8 nucleotides. $N_1$ and $N_2$ are nucleic acid molecules having between 0 and 5 nucleotides as long as $N_1ZN_2$ has at least 6 nucleotides in total. The nucleotides of $N_1ZN_2$ have a phosphodiester backbone and do not include nucleic acids having a modified backbone. Z is an immunostimulatory nucleic acid motif, preferably selected from those recited herein.

The center nucleotides ($N_1ZN_2$) of the formula $Y_1N_1ZN_2Y_2$ have phosphodiester internucleotide linkages and $Y_1$ and $Y_2$ have at least one, but may have more than one or even may have all modified internucleotide linkages. In preferred embodiments $Y_1$ and/or $Y_2$ have at least two or between two and five modified internucleotide linkages or $Y_1$ has two modified internucleotide linkages and $Y_2$ has five modified internucleotide linkages or $Y_1$ has five modified internucleotide linkages and $Y_2$ has two modified internucleotide linkages. The modified internucleotide linkage, in some embodiments is a phosphorothioate modified linkage, a phosphorodithioate modified linkage or a p-ethoxy modified linkage.

The nucleic acids also include nucleic acids having backbone sugars which are covalently attached to low molecular weight organic groups other than a hydroxyl group at the 2' position and other than a phosphate group at the 5' position. Thus, modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have amino acid backbone with nucleic acid bases). In some embodiments, the nucleic acids are homogeneous in backbone composition. Other examples are described in more detail below.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O-($C_1$-$C_6$)alkyl-ribose, preferably 2'-O—($C_1$-$C_6$) alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some embodiments the sugar is 2'-O-methylribose, particularly for one or both nucleotides linked by a phosphodiester or phosphodiester-like internucleoside linkage.

For use in the instant invention, the oligonucleotides of the invention can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler et al., *Nucl. Acid. Res.* 14:5399-5407, 1986,; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These oligonucleotides are referred to as synthetic oligonucleotides. Alternatively, T-rich and/or TG dinucleotides can be produced on a large scale in plasmids, (see Sambrook, T., et al., "Molecular Cloning: A Laboratory Manual", Cold Spring Harbor laboratory Press, New York, 1989) and separated into smaller pieces or administered whole. Nucleic acids can be prepared from existing nucleic acid sequences (e.g., genomic or cDNA) using known techniques, such as those employing restriction enzymes, exonucleases or endonucleases.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., *Chem. Rev.* 90:544, 1990; Goodchild, J., *Bioconjugate Chem.* 1:165, 1990).

Nucleic acids prepared in this manner are referred to as isolated nucleic acid. An "isolated nucleic acid" generally refers to a nucleic acid which is separated from components with which it is normally associated in nature. As an example, an isolated nucleic acid may be one which is separated from a cell, from a nucleus, from mitochondria or from chromatin.

In the case where the nucleic acid is administered in conjunction with an antigen that is encoded in a nucleic acid vector (as described herein), it is preferred that the backbone of the nucleic acid be a chimeric combination of phosphodiester and phosphorothioate (or other phosphate modification) . The cell may have a problem taking up a plasmid vector in the presence of completely phosphorothioate nucleic acid. Thus when both a vector and a nucleic acid are delivered to a subject, it is preferred that the nucleic acid have a chimeric backbone or have a phosphorothioate backbone but that the plasmid be associated with a vehicle that delivers it directly into the cell, thus avoiding the need for cellular uptake. Such vehicles are known in the art and include, for example, liposomes and gene guns.

The invention further embraces the use of any of these foregoing nucleic acids in the methods recited herein, as well as all previously described and previously known uses of immunostimulatory nucleic acids.

It has been discovered according to the invention that the immunostimulatory nucleic acids have surprisingly increased immune stimulatory effects. For example, it has been demonstrated that the nucleic acids described herein are able to provide protection against infection, probably by generally stimulating the immune system. The Examples illustrate the ability of the nucleic acid having a nucleotide sequence of SEQ ID NO:1 to protect murine subjects challenged with Herpes Simplex Virus 2 (HSV-2). The nucleic acid can administered prior to or at the same time as viral challenge.

The demonstrated ability of these nucleic acids to induce immune stimulation is evidence that the nucleic acids are effective therapeutic agents for vaccination, cancer immunotherapy, asthma immunotherapy, general enhancement of immune function, enhancement of hematopoietic recovery following radiation or chemotherapy, and other immune modulatory applications in humans and other subjects.

The nucleic acids of the invention can be used as stand alone therapies. A stand alone therapy is a therapy in which a prophylactically or therapeutically beneficial result can be achieved from the administration of a single agent or composition. Accordingly, the nucleic acids disclosed herein can be used alone in the prevention or treatment of infectious disease, cancer, and asthma and allergy, because the nucleic acids are capable of inducing immune responses that are beneficial to the therapeutic outcome of these diseases. Some of the methods described herein relate to the use of nucleic acids as a stand alone therapy, while others related to the use of the nucleic acids in combination with other therapeutic agents.

When used in a vaccine, the nucleic acid is administered with an antigen. Preferably, the antigen is specific for the disorder sought to be prevented or treated. For example, if the disorder is an infectious disease, the antigen is preferably derived from the infectious organism (e.g., bacterium, virus, parasite, fungus, etc.). If the disorder is a cancer, the antigen is preferably a cancer antigen.

The immunostimulatory nucleic acids are useful in some aspects of the invention as a prophylactic vaccine for the prevention of an infection (i.e., an infectious disease), a cancer, an allergy, or asthma. Preferably, prophylactic vaccination is used in subjects that are not diagnosed with one of these conditions, and more preferably the subjects are considered at risk of developing one of these conditions. For example, the subject may be one that is at risk of developing an infection with an infectious organism, or one that is at risk of developing a cancer in which a specific cancer antigen has been identified, or one that is at risk of developing an allergy for which an allergen is known, or one that is at risk of developing asthma where the predisposition to asthma is known.

A subject at risk, as used herein, is a subject who has any risk of exposure to an infection causing pathogen, a carcinogen, or an allergen. A subject at risk also includes subjects that have a predisposition to developing such disorders. Some predispositions can be genetic (and can thereby be identified either by genetic analysis or by family history). Some predispositions are environmental (e.g., prior exposure to carcinogens, etc.) An example of a subject at risk of developing an infection is a subject living in or expecting to travel to an area where a particular type of infectious agent is or has been found, or it may be a subject who through lifestyle or medical procedures is exposed to an organism either directly or indirectly by contact with bodily fluids that may contain infectious organisms. Subjects at risk of developing infection also include general populations to which a medical agency recommends vaccination for a particular infectious organism.

If the antigen is an allergen and the subject develops allergic responses to that particular antigen and the subject may be exposed to the antigen, i.e., during pollen season, then that subject is at risk of exposure to the antigen. A subject at risk of developing an allergy to asthma includes those subjects that have been identified as having an allergy or asthma but that don't have the active disease during the immunostimulatory nucleic acid treatment as well as subjects that are considered to be at risk of developing these diseases because of genetic or environmental factors.

The immunostimulatory nucleic acids can also be given without the antigen or allergen for shorter term protection against infection, allergy or cancer, and in this case repeated doses will allow longer term protection.

A subject at risk of developing a cancer is one who is who has a high probability of developing cancer (e.g., a probability that is greater than the probability within the general public). These subjects include, for instance, subjects having a genetic abnormality, the presence of which has been demonstrated to have a correlative relation to a likelihood of developing a cancer that is greater than the likelihood of the general public, and subjects exposed to cancer causing agents (i.e., carcinogens) such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a immunostimulatory nucleic acid, the subject may be able to kill the cancer cells as they develop. If a tumor begins to form in the subject, the subject will develop a specific immune response against the tumor antigen.

In addition to the use of the immunostimulatory nucleic acids as a prophylactic, the invention also encompasses the use of the immunostimulatory nucleic acids for the treatment of a subject having an infection, an allergy, asthma, or a cancer.

A subject having an infection is a subject that has been exposed to an infectious pathogen and has acute or chronic detectable levels of the pathogen in the body, or in bodily waste. When used therapeutically, the immunostimulatory nucleic acids can be used as a stand alone or in combination with another therapeutic agent. For example, the immunostimulatory nucleic acids can be used therapeutically with an antigen to mount an antigen specific systemic or mucosal immune response that is capable of reducing the level of, or eradicating, the infectious pathogen.

An infectious disease, as used herein, is a disease arising from the presence of a foreign microorganism in the body. It is particularly important to develop effective vaccine strategies and treatments to protect the body's mucosal surfaces, which are the primary site of pathogenic entry.

As used herein, the term treat, treated, or treating when used with respect to an infectious disease refers to a prophylactic treatment which increases the resistance of a subject (a subject at risk of infection) to infection with a pathogen or, in other words, decreases the likelihood that the subject will become infected with the pathogen as well as a treatment after the subject (a subject who has been infected) has become infected in order to fight the infection, e.g., reduce or eliminate the infection or prevent it from becoming worse.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Currently, allergic diseases are generally treated by the injection of small doses of antigen followed by subsequent increasing dosage of antigen. It is believed that this procedure induces tolerization to the allergen to prevent further allergic reactions. These methods, however, can take several years to be effective and are associated with the risk of side effects such as anaphylactic shock. The methods of the invention avoid these problems.

Allergies are generally caused by IgE antibody generation against harmless allergens. The cytokines that are induced by systemic or mucosal administration of immunostimulatory nucleic acids are predominantly of a class called Th1 (examples are IL-12 and IFN-γ) and these induce both humoral and cellular immune responses. The types of antibodies associated with a Th1 response are generally more protective because they have high neutralization and opsonization capabilities. The other major type of immune response, which is associated with the production of IL-4, IL-5 and IL-10 cytokines, is termed a Th2 immune response. Th2 responses involve predominately antibodies and these have less protective effect against infection and some Th2 isotypes (e.g., IgE) are associated with allergy. In general, it appears that allergic diseases are mediated by Th2 type immune responses while Th1 responses provide the best protection against infection, although excessive Th1 responses are associated with autoimmune disease. Based on the ability of the immunostimulatory nucleic acids to shift the immune response in a subject from a Th2 (which is associated with production of IgE antibodies and allergy) to a Th1 response (which is protective against allergic reactions), an effective dose for inducing an immune response of a immunostimulatory nucleic acid can be administered to a subject to treat or prevent an allergy.

Thus, the immunostimulatory nucleic acids have significant therapeutic utility in the treatment of allergic and non-allergic conditions such as asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

Some cancer cells are antigenic and thus can be targeted by the immune system. In one aspect, the combined administration of immunostimulatory nucleic acids and cancer medicaments, particularly those which are classified as cancer immunotherapies, is useful for stimulating a specific immune response against a cancer antigen.

The theory of immune surveillance is that a prime function of the immune system is to detect and eliminate neoplastic cells before a tumor forms. A basic principle of this theory is that cancer cells are antigenically different from normal cells and thus elicit immune reactions that are similar to those that cause rejection of immunologically incompatible allografts. Studies have confirmed that tumor cells differ, either qualitatively or quantitatively, in their expression of antigens. Such antigens are referred to interchangeably as tumor antigens or cancer antigens. Some of these antigens may in turn be tumor-specific antigens or tumor-associated antigens. "Tumor-specific antigens" are antigens that are specifically present in tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen dependent nor MHC restricted once activated. Activated macrophages are through to decrease the growth rate of the tumors they infiltrate. In vitro assays have identified other immune mechanisms such as antibody-dependent, cell-mediated cytotoxic reactions and lysis by antibody plus complement. However, these immune effector mechanisms are thought to be less important in vivo than the function of NK, CTLs, LAK, and macrophages in vivo (for review see Piessens, W. F., and David, J., "Tumor Immunology", In: *Scientific American Medicine*, Vol. 2, Scientific American Books, N.Y., pp. 1-13, 1996.

The goal of immunotherapy is to augment a patient's immune response to an established tumor. One method of immunotherapy includes the use of adjuvants. Adjuvant substances derived from microorganisms, such as bacillus Calmette-Guerin, heighten the immune response and enhance resistance to tumors in animals.

An "antigen" as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens. The term antigen broadly includes any type of molecule which is recognized by a host immune system as being foreign. Antigens include but are not limited to cancer antigens, microbial antigens, and allergens.

A "microbial antigen" as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

A "cancer antigen" as used herein is a compound, such as a peptide or protein, present in a tumor or cancer cell and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

Cancer or tumor antigens are differentially expressed by cancer cells and can thereby be exploited in order to target cancer cells. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

In some aspects of the invention, the subject is "exposed to" the antigen. As used herein, the term "exposed to" refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the immunostimulatory nucleic acid are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

Active exposure of the antigen can occur at any time relative to the administration of the immunostimulatory nucleic acid, including prior to, simultaneously with, or following nucleic acid administration. In some embodiments, the nucleic acid is administered at the same time, or substantially the same time (e.g., within an hour) of exposure to the antigen, but is administered in a different formulation. As an example, the antigen may be administered locally, and the nucleic acid may be administered systemically, or vice versa.

The methods in which a subject is passively exposed to an antigen can be particularly dependent on timing of administration of the immunostimulatory nucleic acid. For instance, in a subject at risk of developing a cancer or an infectious disease or an allergic or asthmatic response, the subject may be administered the immunostimulatory nucleic acid on a regular basis when that risk is greatest, i.e., during allergy season or after exposure to a cancer causing agent. Additionally the immunostimulatory nucleic acid may be administered to travelers before they travel to foreign lands where they are at risk of exposure to infectious agents. Likewise the immunostimulatory nucleic acid may be administered to soldiers or civilians at risk of exposure to biowarfare to induce a systemic or mucosal immune response to the antigen when and if the subject is exposed to it.

A subject preferably is a non-rodent subject. A non-rodent subject shall mean a human or vertebrate animal including but not limited to a dog, cat, horse, cow, pig, sheep, goat, chicken, primate, e.g., monkey, and fish (aquaculture species), e.g. salmon, but specifically excluding rodents such as rats and mice.

Antigens can be derived from various sources including tumor, non-tumor cancers, allergens, and infectious pathogens. Each of the lists recited herein is not intended to be limiting.

Examples of viruses that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of *Spongiform encephalopathies,* the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Although many of the microbial antigens described herein relate to human disorders, the invention is also useful for treating other non-human vertebrates. Non-human vertebrates are also capable of developing infections which can be prevented or treated with the immunostimulatory nucleic acids disclosed herein. For instance, in addition to the treatment of infectious human diseases, the methods of the invention are useful for treating infections of animals.

Both gram negative and gram positive bacteria serve as antigens in vertebrate animals. Such gram positive bacteria include, but are not limited to, Pasteurella species, Staphylococci species, and Streptococcus species. Gram negative bacteria include, but are not limited to, *Escherichia coli,* Pseudomonas species, and *Salmonella* species. Specific examples of infectious bacteria include but are not limited to, *Helicobacter pyloris, Borelia burgdorferi, Legionella pneumophilia,* Mycobacteria sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus antracis*, corynebacterium diphtheriae, corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue, Leptospira, Rickettsia*, and *Actinomyces israelli*.

Polypeptides of bacterial pathogens include but are not limited to an iron-regulated outer membrane protein, (IROMP), an outer membrane protein (OMP), and an A-protein of Aeromonis salmonicida which causes furunculosis, p57 protein of Renibacterium salmoninarum which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (IROMP), and a structural protein of Pasteurellosis; an OMP and a flagellar protein of Vibrosis anguillarum and V. ordalii; a flagellar protein, an OMP protein, aroA, and purA of Edwardsiellosis ictaluri and E. tarda; and surface antigen of Ichthyophthirius; and a structural and regulatory protein of Cytophaga columnari; and a structural and regulatory protein of Rickettsia.

Polypeptides of a parasitic pathogen include but are not limited to the surface antigens of Ichthyophthirius.

Examples of fungi include *Cryptococcus neoformans, Histoplasma capsulatum, Coccidioides immitis, Blastomyces dermatitidis, Chlamydia trachomatis, Candida albicans*. Other infectious organisms (i.e., protists) include *Plasmodium* spp. such as *Plasmodium falciparum, Plasmodium malariae, Plasmodium ovale*, and *Plasmodium* vivax and *Toxoplasma gondii*. Blood-borne and/or tissues parasites include Plasmodium spp., *Babesia microti, Babesia divergens, Leishmania tropica*, Leishmania spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*. Other medically relevant microorganisms have been described extensively in the literature, e.g., see C. G. A Thomas, *Medical Microbiology*, Bailliere Tindall, Great Britain 1983, the entire contents of which is hereby incorporated by reference.

Many vaccines for the treatment of non-human vertebrates are disclosed in Bennett, K. *Compendium of Veterinary Products*, 3rd ed. North American Compendiums, Inc., 1995. As discussed above, antigens include infectious microbes such as virus, parasite, bacteria and fungi and fragments thereof, derived from natural sources or synthetically. Infectious viruses of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-I, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are antigens in vertebrate animals include, but are not limited to, members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Hepatitis virus, Human enteric corona virus, and Feline infectious peritonitis (Feline coronavirus).

Illustrative DNA viruses that are antigens in vertebrate animals include, but are not limited to, the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine and monkeys); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D, E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

The immunostimulatory nucleic acids can also be used to induce an immune response, such as an antigen specific immune response, birds such as hens, chickens, turkeys, ducks, geese, quail, and pheasant. Birds are prime targets for many types of infections.

Hatching birds are exposed to pathogenic microorganisms shortly after birth. Although these birds are initially protected against pathogens by maternal derived antibodies, this protection is only temporary, and the bird's own immature immune system must begin to protect the bird against the pathogens. It is often desirable to prevent infection in young birds when they are most susceptible. It is also desirable to prevent against infection in older birds, especially when the birds are housed in closed quarters, leading to the rapid spread of disease. Thus, it is desirable to administer the Immunostimulatory nucleic acid and the non-nucleic acid adjuvant of the invention to birds to enhance an antigen-specific immune response when antigen is present.

An example of a common infection in chickens is chicken infectious anemia virus (CIAV). CIAV was first isolated in Japan in 1979 during an investigation of a Marek's disease vaccination break (Yuasa et al., 1979, Avian Dis. 23:366-385). Since that time, CIAV has been detected in commercial poultry in all major poultry producing countries (van Bulow et al., 1991, pp. 690-699) in Diseases of Poultry, 9th edition, Iowa State University Press).

CIAV infection results in a clinical disease, characterized by anemia, hemorrhage and immunosuppression, in young susceptible chickens. Atrophy of the thymus and of the bone marrow and consistent lesions of CIAV-infected chickens are also characteristic of CIAV infection. Lymphocyte depletion in the thymus, and occasionally in the bursa of Fabricius, results in immunosuppression and increased susceptibility to secondary viral, bacterial, or fungal infections which then complicate the course of the disease. The immunosuppression may cause aggravated disease after infection with one or more of Marek's disease virus (MDV), infectious bursal disease virus, reticuloendotheliosis virus, adenovirus, or reovirus. It has been reported that pathogenesis of MDV is enhanced by CIAV (DeBoer et al., 1989, p. 28 In Proceedings of the 38th Western Poultry Diseases Conference, Tempe, Ariz.). Further, it has been reported that CIAV aggravates the signs of infectious bursal disease (Rosenberger et al., 1989, Avian Dis. 33:707-713). Chickens develop an age resistance to experimentally induced disease due to CAA. This is essentially complete by the age of 2 weeks, but older birds are still susceptible to infection (Yuasa, N. et al., 1979 supra; Yuasa, N. et al., Arian Diseases 24, 202-209, 1980). However, if chickens are dually infected with CAA and an immunosuppressive agent (IBDV, MDV etc.), age resistance against the disease is delayed (Yuasa, N. et al., 1979 and 1980 supra; Bulow von V. et al., J. Veterinary Medicine 33, 93-116, 1986). Characteristics of CIAV that may potentiate disease transmission include high resistance to environmental inactivation and some common disinfectants. The economic impact of CIAV infection on the poultry industry is clear from the fact that 10% to 30% of infected birds in disease outbreaks die.

Vaccination of birds, like other vertebrate animals can be performed at any age. Normally, vaccinations are performed at up to 12 weeks of age for a live microorganism and between 14-18 weeks for an inactivated microorganism or other type of vaccine. For in ovo vaccination, vaccination can be performed in the last quarter of embryo development. The vaccine may be administered subcutaneously, by spray, orally, intraocularly, intratracheally, nasally, or by other mucosal delivery methods described herein. Thus, the immunostimulatory nucleic acids of the invention can be administered to birds and other non-human vertebrates using routine vaccination schedules and the antigen can be administered after an appropriate time period as described herein. Cattle and livestock are also susceptible to infection. Diseases which affect these animals can produce severe economic losses, especially amongst cattle. The methods of the invention can be used to protect against infection in livestock, such as cows, horses, pigs, sheep, and goats.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the pestivirus genus. Although, Pestiviruses were previously classified in the Togaviridae family, some studies have suggested their reclassification within the Flaviviridae family along with the flavivirus and hepatitis C virus (HCV) groups (Francki, et al., 1991).

BVDV, which is an important pathogen of cattle can be distinguished, based on cell culture analysis, into cytopathogenic (CP) and noncytopathogenic (NCP) biotypes. The NCP biotype is more widespread although both biotypes can be found in cattle. If a pregnant cow becomes infected with an NCP strain, the cow can give birth to a persistently infected and specifically immunotolerant calf that will spread virus during its lifetime. The persistently infected cattle can succumb to mucosal disease and both biotypes can then be isolated from the animal. Clinical manifestations can include abortion, teratogenesis, and respiratory problems, mucosal disease and mild diarrhea. In addition, severe thrombocytopenia, associated with herd epidemics, that may result in the death of the animal has been described and strains associated with this disease seem more virulent than the classical BVDVs.

Equine herpes viruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Primary infection of upper respiratory tract of young horses results in a febrile illness which lasts for 8 to 10 days. Immunologically experienced mares may be re-infected via the respiratory tract without disease becoming apparent, so that abortion usually occurs without warning. The neurological syndrome is associated with respiratory disease or abortion and can affect animals of either sex at any age, leading to lack of co-ordination, weakness and posterior paralysis (Telford, E. A. R. et al., Virology 189, 304-316, 1992). Other EHV's include EHV-2, or equine cytomegalovirus, EHV-3, equine coital exanthema virus, and EHV-4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al. (1990) Lancet 36:1538-1541; Desrosiers et al. PNAS USA (1989) 86:6353-6357; Murphey-Corb et al. (1989) Science 246:1293-1297; and Carlson et al. (1990) AIDS Res. Human Retroviruses 6:1239-1246). A recombinant HIV gp120 vaccine has been reported to afford protection in chimpanzees (Berman et al. (1990) Nature 345:622-625).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to protect them against infection.

Domestic cats may become infected with several retroviruses, including but not limited to feline leukemia virus (FeLV), feline sarcoma virus (FeSV), endogenous type C-oncornavirus (RD-114), and feline syncytia-forming virus (FeSFV). Of these, FeLV is the most significant pathogen, causing diverse symptoms, including lymphoreticular and myeloid neoplasms, anemias, immune mediated disorders, and an immunodeficiency syndrome which is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (also referred to as feline immunodeficiency) was first reported in Pedersen et al. (1987) Science 235:790-793. Characteristics of FIV have been reported in Yamamoto et al. (1988) Leukemia, December Supplement 2:204S-215S; Yamamoto et al. (1988) Am. J. Vet. Res. 49:1246-1258; and Ackley et al. (1990) J. Virol. 64:5652-5655. Cloning and sequence analysis of FIV have been reported in Olmsted et al. (1989) Proc. Natl. Acad. Sci. USA 86:2448-2452 and 86:4355-4360.

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old.

Viral, bacterial, and parasitic diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Nucleic acid based vaccinations are described in U.S. Pat. No. 5,780,448 issued to Davis.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered by immersion or orally.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

Polypeptides of viral aquaculture pathogens include but are not limited to glycoprotein (G) or nucleoprotein (N) of viral hemorrhagic septicemia virus (VHSV); G or N proteins of infectious hematopoietic necrosis virus (IHNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Typical parasites infecting horses are Gasterophilus spp.; *Eimeria leuckarti*, Giardia spp.; *Tritrichomonas equi*; Babesia spp. (RBC's), *Theileria equi*; Trypanosoma spp.; *Klossiella equi*; Sarcocystis spp. Typical parasites infecting swine include *Eimeria bebliecki, Eimeria scabra, Isospora suis*, Giardia spp.; *Balantidium coli, Entamoeba histolytica; Toxoplasma gondii* and Sarcocystis spp., and *Trichinella spiralis*.

The major parasites of dairy and beef cattle include Eimeria spp., Cryptosporidium sp., Giardia spp.; *Toxoplasma gondii; Babesia bovis* (RBC), *Babesia bigemina* (RBC), Trypanosoma spp. (plasma), Theileria spp. (RBC); *Theileria parva* (lymphocytes); *Tritrichomonas foetus*; and Sarcocystis spp.

The major parasites of raptors include *Trichomonas gallinae*; Coccidia (Eimeria spp.); *Plasmodium relictum, Leucocytozoon danilewskyi* (owls), Haemoproteus spp., Trypanosoma spp.; *Histomonas; Cryptosporidium meleagridis, Cryptosporidium baileyi, Giardia, Eimeria; Toxoplasma.*

Typical parasites infecting sheep and goats include Eimeria spp., Cryptosporidium sp., Giardia sp.; *Toxoplasma gon-*

*dii*; *Babesia* spp. (RBC), *Trypanosoma* spp. (plasma), *Theileria* spp. (RBC); and *Sarcocystis* spp.

Typical parasitic infections in poultry include coccidiosis caused by *Eimeria acervulina, E. necatrix, E. tenella, Isospora* spp. and *Eimeria truncata*; histomoniasis, caused by *Histomonas meleagridis* and *Histomonas gallinarum*; trichomoniasis caused by *Trichomonas gallinae*; and hexamitiasis caused by *Hexamita meleagridis*. Poultry can also be infected *Emeria maxima, Emeria meleagridis, Eimeria adenoeides, Eimeria meleagrimitis, Cryptosporidium, Eimeria brunetti, Emeria adenoeides, Leucocytozoon* spp., *Plasmodium* spp., *Hemoproteus meleagridis, Toxoplasma gondii* and *Sarcocystis*.

The methods of the invention can also be applied to the treatment and/or prevention of parasitic infection in dogs, cats, birds, fish and ferrets. Typical parasites of birds include *Trichomonas gallinae*; Eimeria spp., Isospora spp., Giardia; Cryptosporidium; Sarcocystis spp., *Toxoplasma gondii*, Haemoproteus/Parahaemoproteus, Plasmodium spp., Leucocytozoon/Akiba, Atoxoplasma, Trypanosoma spp. Typical parasites infecting dogs include *Trichinella spiralis*; Isospora spp., Sarcocystis spp., Cryptosporidium spp., Hammondia spp., *Giardia duodenalis* (canis); *Balantidium coli, Entamoeba histolytica; Hepatozoon canis; Toxoplasma gondii, Trypanosoma cruzi; Babesia canis; Leishmania amastigotes; Neospora caninum*.

Typical parasites infecting feline species include Isospora spp., *Toxoplasma gondii*, Sarcocystis spp., *Hammondia hammondi*, Besnoitia spp., Giardia spp.; *Entamoeba histolytica; Hepatozoon canis*, Cytauxzoon sp., Cytauxzoon sp., Cytauxzoon sp. (red cells, RE cells).

Typical parasites infecting fish include Hexamita spp., Eimeria spp.; Cryptobia spp., Nosema spp., Myxosoma spp., Chilodonella spp., Trichodina spp.; Plistophora spp., *Myxosoma Henneguya*; Costia spp., Ichthyophithirius spp., and Oodinium spp.

Typical parasites of wild mammals include Giardia spp. (carnivores, herbivores), Isospora spp. (carnivores), Eimeria spp. (carnivores, herbivores); Theileria spp. (herbivores), Babesia spp. (carnivores, herbivores), Trypanosoma spp. (carnivores, herbivores); Schistosoma spp. (herbivores); *Fasciola hepatica* (herbivores), *Fascioloides magna* (herbivores), *Fasciola gigantica* (herbivores), *Trichinella spiralis* (carnivores, herbivores).

Parasitic infections in zoos can also pose serious problems. Typical parasites of the bovidae family (blesbok, antelope, banteng, eland, gaur, impala, klipspringer, kudu, gazelle) include Eimeria spp. Typical parasites in the pinnipedae family (seal, sea lion) include *Eimeria phocae*. Typical parasites in the camelidae family (camels, llamas) include Eimeria spp. Typical parasites of the giraffidae family (giraffes) include Eimeria spp. Typical parasites in the elephantidae family (African and Asian) include Fasciola spp. Typical parasites of lower primates (chimpanzees, orangutans, apes, baboons, macaques, monkeys) include Giardia sp.; *Balantidium coli, Entamoeba histolytica*, Sarcocystis spp., *Toxoplasma gondii*; Plasmodim spp. (RBC), Babesia spp. (RBC), Trypanosoma spp. (plasma), Leishmania spp. (macrophages).

Cancer is one of the leading causes of death in companion animals (i.e., cats and dogs). Cancer usually strikes older animals which, in the case of house pets, have become integrated into the family. Forty-five % of dogs older than 10 years of age, are likely to succumb to the disease. The most common treatment options include surgery, chemotherapy and radiation therapy. Others treatment modalities which have been used with some success are laser therapy, cryotherapy, hyperthermia and immunotherapy. The choice of treatment depends on type of cancer and degree of dissemination. Unless the malignant growth is confined to a discrete area in the body, it is difficult to remove only malignant tissue without also affecting normal cells.

Malignant disorders commonly diagnosed in dogs and cats include but are not limited to lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma. Other neoplasias in dogs include genital squamous cell carcinoma, transmissable venereal tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an evermore popular house pet is known to develop insulinoma, lymphoma, sarcoma, neuroma, pancreatic islet cell tumor, gastric MALT lymphoma and gastric adenocarcinoma.

Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lumphadenitis (CLA): chronic, infectious, contagious disease of sheep and goats caused by the bacterium Corynebacterium pseudotuberculosis, and contagious lung tumor of sheep caused by jaagsiekte.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); Dermatophagoides (e.g. *Dermatophagoides farinae*); Felis (*Felis domesticus*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alder; Alnus (*Alnus gultinoasa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*);

Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

The antigen may be an antigen that is encoded by a nucleic acid vector or it may be not encoded in a nucleic acid vector. In the former case the nucleic acid vector is administered to the subject and the antigen is expressed in vivo. In the latter case the antigen may be administered directly to the subject. An antigen not encoded in a nucleic acid vector as used herein refers to any type of antigen that is not a nucleic acid. For instance, in some aspects of the invention the antigen not encoded in a nucleic acid vector is a polypeptide. Minor modifications of the primary amino acid sequences of polypeptide antigens may also result in a polypeptide which has substantially equivalent antigenic activity as compared to the unmodified counterpart polypeptide. Such modifications may be deliberate, as by site-directed mutagenesis, or may be spontaneous. All of the polypeptides produced by these modifications are included herein as long as antigenicity still exists. The polypeptide may be, for example, a viral polypeptide.

The term "substantially purified" as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are described above, and included within the invention.

The invention also utilizes polynucleotides encoding the antigenic polypeptides. It is envisioned that the antigen may be delivered to the subject in a nucleic acid molecule which encodes for the antigen such that the antigen must be expressed in vivo. Such antigens delivered to the subject in a nucleic acid vector are referred to as antigens encoded by a nucleic acid vector. The nucleic acid encoding the antigen is operatively linked to a gene expression sequence which directs the expression of the antigen nucleic acid within a eukaryotic cell. The gene expression sequence is any regulatory nucleotide sequence, such as a promoter sequence or promoter-enhancer combination, which facilitates the efficient transcription and translation of the antigen nucleic acid to which it is operatively linked.

The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, b-actin promoter and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

The antigen nucleic acid is operatively linked to the gene expression sequence. As used herein, the antigen nucleic acid sequence and the gene expression sequence are said to be operably linked when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the antigen sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein.

Thus, a gene expression sequence would be operably linked to an antigen nucleic acid sequence if the gene expression sequence were capable of effecting transcription of that antigen nucleic acid sequence such that the resulting transcript is translated into the desired protein or polypeptide.

The antigen nucleic acid of the invention may be delivered to the immune system alone or in association with a vector. In its broadest sense, a vector is any vehicle capable of facilitating the transfer of the antigen nucleic acid to the cells of the immune system so that the antigen can be expressed and presented on the surface of the immune cell. The vector generally transports the nucleic acid to the immune cells with reduced degradation relative to the extent of degradation that would result in the absence of the vector. The vector optionally includes the above-described gene expression sequence to enhance expression of the antigen nucleic acid in immune cells. In general, the vectors useful in the invention include, but are not limited to, plasmids, phagemids, viruses, other vehicles derived from viral or bacterial sources that have been manipulated by the insertion or incorporation of the antigen nucleic acid sequences. Viral vectors are a preferred type of vector and include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo.

Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., Gene Transfer and Expression, A Laboratory Manual W. H. Freeman C. O., New York (1990) and Murry, E. J. Methods in Molecular Biology, vol. 7, Humana Press, Inc., Cliffton, N.J. (1991).

A preferred virus for certain applications is the adeno-associated virus, a double-stranded DNA virus. The adeno-associated virus can be engineered to be replication-deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlue-Script. Other plasmids are well-known to those of ordinary skill in the art. Additionally, plasmids may be custom designed using restriction enzymes and ligation reactions to remove and add specific fragments of DNA.

It has recently been discovered that gene carrying plasmids can be delivered to the immune system using bacteria. Modified forms of bacteria such as *Salmonella* can be transfected with the plasmid and used as delivery vehicles. The bacterial delivery vehicles can be administered to a host subject orally or by other administration means. The bacteria deliver the plasmid to immune cells, e.g. B cells, dendritic cells, likely by passing through the gut barrier. High levels of immune protection have been established using this methodology. Such methods of delivery are useful for the aspects of the invention utilizing systemic delivery of antigen, Immunostimulatory nucleic acid and/or other therapeutic agent.

Thus, in addition to being suitable as stand alone agents, the immunostimulatory nucleic acids are useful, inter alia, as vaccine adjuvants. It was previously established that CpG oligonucleotides are excellent vaccine adjuvants. In order to identify the best immunostimulatory nucleic acids for use as a vaccine adjuvant in humans and other non-rodent animals, in vivo screening of different nucleic acids for this purpose was conducted. Several in vitro assays were evaluated in mice for their predictive value of adjuvant activity in vivo. During the course of this study, an in vitro test that is predictive of in vivo efficacy was identified. It was discovered, rather surprisingly, that both B cell and NK cell activation correlated particularly well with the ability of an immunostimulatory nucleic acid to enhance an in vivo immune response against an antigen.

The nucleic acids are also useful for improving survival, differentiation, activation and maturation of dendritic cells. The immunostimulatory nucleic acids have the unique capability to promote cell survival, differentiation, activation and maturation of dendritic cells. Dendritic precursor cells isolated from blood by immunomagnetic cell sorting develop morphologic and functional characteristics of dendritic cells during a two day incubation with GM-CSF. Without GM-CSF these cells undergo apoptosis. The immunostimulatory nucleic acids are superior to GM-CSF in promoting survival and differentiation of dendritic cells (MHC II expression, cell size, granularity). The immunostimulatory nucleic acids also induce maturation of dendritic cells. Since dendritic cells form the link between the innate and the acquired immune system, by presenting antigens as well as through their expression of pattern recognition receptors which detect microbial molecules like LPS in their local environment, the ability to activate dendritic cells with immunostimulatory nucleic acids supports the use of these immunostimulatory nucleic acid based strategies for in vivo and ex-vivo immunotherapy against disorders such as cancer and allergic or infectious diseases. The immunostimulatory nucleic acids are also useful for activating and inducing maturation of dendritic cells.

Immunostimulatory nucleic acids also increase natural killer cell lytic activity and antibody dependent cellular cytotoxicity (ADCC). ADCC can be performed using a immunostimulatory nucleic acid in combination with an antibody specific for a cellular target, such as a cancer cell. When the immunostimulatory nucleic acid is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available. Examples of these antibodies are listed below among the list of cancer immunotherapies.

The nucleic acids are also useful for redirecting an immune response from a Th2 immune response to a Th1 immune response. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-γ and GM-CSF). The redirection or rebalance of the immune response from a Th2 to a Th1 response is particularly useful for the treatment or prevention of asthma. For instance, an effective amount for treating asthma can be that amount; useful for redirecting a Th2 type of immune response that is associated with asthma to a Th1 type of response. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. The immunostimulatory nucleic acids of the invention cause an increase in Th1 cytokines which helps to rebalance the immune system, preventing or reducing the adverse effects associated with a predominately Th2 immune response.

The invention also includes a method for inducing antigen non-specific innate immune activation and broad spectrum resistance to infectious challenge using the immunostimulatory nucleic acids. The term antigen non-specific innate immune activation as used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The nucleic acids of the invention can be used in combination with other therapeutic agents including anti-microbial agents, adjuvants, cytokines, anti-cancer therapies, allergy medicaments, asthma medicaments, and the like.

The nucleic acids of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions.

Antibiotics are low molecular weight molecules which are produced as secondary metabolites by cells, such as microorganisms. In general, antibiotics interfere with one or more bacterial functions or structures which are specific for the microorganism and which are not present in host cells. Antiviral agents can be isolated from natural sources or synthesized and are useful for killing or inhibiting viruses. Antifungal agents are used to treat superficial fungal infections as well as opportunistic and primary systemic fungal infections. Anti-parasite agents kill or inhibit parasites.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics.

Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Anti-bacterial agents useful in the invention include but are not limited to natural penicillins, semi-synthetic penicillins, clavulanic acid, cephalosporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, carbapenems, imipenems, monobactems, euztreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim; Acedapsone Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone Daptomycin; Demeclocycline; Demeclocycline Hydrochloride; Demecycline; Denofungin; Diaveridine; Dicloxacillin;

Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffunycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine). The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immunocompromised children and neonates), human rabies immunoglobulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Another type of immunoglobulin therapy is active immunization. This involves the administration of antibodies or antibody fragments to viral surface proteins. Two types of vaccines which are available for active immunization of hepatitis B include serum-derived hepatitis B antibodies and recombinant hepatitis B antibodies. Both are prepared from HBsAg. The antibodies are administered in three doses to subjects at high risk of infection with hepatitis B virus, such as health care workers, sexual partners of chronic carriers, and infants.

Thus, anti-viral agents useful in the invention include but are not limited to immunoglobulins, amantadine, interferon, nucleoside analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream). Some examples of commercially-available agents are shown in Table 1.

TABLE 1

| Company | Brand Name | Generic Name | Indication | Mechanism of Action |
| --- | --- | --- | --- | --- |
| PHARMACIA & UPJOHN | PNU 196443 | PNU 196443 | Anti Fungal | n/k |
| Lilly | LY 303366 | Basiungin/ECB | Fungal Infections | Anti-fungal/cell wall inhibitor, glucose synthase inhibitor |
| Bayer | Canesten | Clotrimazole | Fungal Infections | Membrane integrity destabilizer |
| Fujisawa | FK 463 | FK 463 | Fungal Infections | Membrane integrity destabilizer |
| Mylan | Sertaconzaole | Sertaconzole | Fungal Infections | Membrane integrity destabilizer |
| Genzyme | Chitinase | Chitinase | Fungal Infections, Systemic | Chitin Breakdown |
| Liposome | Abelcet | Amphotericin B, Liposomal | Fungal Infections, Systemic | Membrane integrity destabilizer |
| Sequus | Amphotec | Amphotericin B, Liposomal | Fungal Infections, Systemic | Membrane integrity destabilizer |
| Bayer | BAY 38-9502 | BAY 38-9502 | Fungal Infections, Systemic | Membrane integrity destabilizer |
| Pfizer | Diflucan | Fluconazole | Fungal Infections, Systemic | Membrane integrity destabilizer |
| Johnson & Johnson | Sporanox | Itraconazole | Fungal Infections, Systemic | Membrane integrity destabilizer |
| Sepracor | Itraconzole (2R, 4S) | Itraconzole (2R, 4S) | Fungal Infections, Systemic | Membrane integrity destabilizer |
| Johnson & Johnson | Nizoral | Ketoconazole | Fungal Infections, Systemic | Membrane integrity destabilizer |
| Johnson & Johnson | Monistat | Miconazole | Fungal Infections, Systemic | Membrane integrity destabilizer |
| Merck | MK 991 | MK 991 | Fungal Infections, Systemic | Membrane integrity destabilizer |
| Bristol Myers Sq'b | Pradimicin | Pradimicin | Fungal Infections, Systemic | Membrane integrity destabilizer |
| Pfizer | UK-292, 663 | UK-292, 663 | Fungal Infections, Systemic | Membrane integrity destabilizer |
| Pfizer | Voriconazole | Voriconazole | Fungal Infections, Systemic | Membrane integrity destabilizer |
| Mylan | 501 Cream | 501 Cream | Inflammatory Fungal Conditions | Immunosuppression |
| Mylan | Mentax | Butenafine | Nail Fungus | Membrane Integrity Destabiliser |
| Schering Plough | Anti Fungal | Anti Fungal | Opportunistic Infections | Membrane Integrity Destabiliser |
| Alza | Mycelex Troche | Clotrimazole | Oral Thrush | Membrane Integrity Stabliser |
| Novartis | Lamisil | Terbinafine | Systemic Fungal Infections, Onychomycosis | Membrane Integrity Destabiliser |

Thus, the anti-fungal agents useful in the invention include but are not limited to imidazoles, FK 463, amphotericin B, BAY 38-9502, MK 991, pradimicin, UK 292, butenafine, chitinase, 501 cream, Acrisorcin; Ambruticin; Amorolfine; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Parasiticides used in non-human subjects include piperazine, diethylcarbamazine, thiabendazole, fenbendazole, albendazole, oxfendazole, oxibendazole, febantel, levamisole, pyrantel tartrate, pyrantel pamoate, dichlorvos, ivermectin, doramectic, milbemycin oxime, iprinomectin, moxidectin, N-butyl chloride, toluene, hygromycin B thiacetarsemide sodium, melarsomine, praziquantel, epsiprantel, benzimidazoles such as fenbendazole, albendazole, oxfendazole, clorsulon, albendazole, amprolium; decoquinate, lasalocid, monensin sulfadimethoxine; sulfamethazine, sulfaquinoxaline, metronidazole.

Parasiticides used in horses include mebendazole, oxfendazole, febantel, pyrantel, dichlorvos, trichlorfon, ivermectin, piperazine; for *S. westeri*: ivermectin, benzimidazoles such as thiabendazole, cambendazole, oxibendazole and fenbendazole. Useful parasiticides in dogs include milbemycin oxime, ivermectin, pyrantel pamoate and the combination of ivermectin and pyrantel. The treatment of parasites in swine can include the use of levamisole, piperazine, pyrantel, thiabendazole, dichlorvos and fenbendazole. In sheep and goats anthelmintic agents include levamisole or ivermectin. Caparsolate has shown some efficacy in the treatment of D. immitis (heartworm) in cats.

The immunostimulatory nucleic acids may also be administered in conjunction with an anti-cancer therapy. Anti-cancer therapies include cancer medicaments, radiation and surgical procedures. As used herein, a "cancer medicament" refers to a agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers. Additionally, the methods of the invention are intended to embrace the use of more than one cancer medicament along with the immunostimulatory nucleic acids. As an example, where appropriate, the immunostimulatory nucleic acids may be administered with a both a chemotherapeutic agent and an immunotherapeutic agent.

Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

Cancer medicaments function in a variety of ways. Some cancer medicaments work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer medicaments can alternately target signal transduction pathways and molecular mechanisms which are altered in cancer cells. Targeting of cancer cells via the epitopes expressed on their cell surface is accomplished through the use of monoclonal antibodies. This latter type of cancer medicament is generally referred to herein as immunotherapy.

Other cancer medicaments target cells other than cancer cells. For example, some medicaments prime the immune system to attack tumor cells (i.e., cancer vaccines). Still other medicaments, called angiogenesis inhibitors, function by attacking the blood supply of solid tumors. Since the most malignant cancers are able to metastasize (i.e., exist the primary tumor site and seed a distal tissue, thereby forming a secondary tumor), medicaments that impede this metastasis are also useful in the treatment of cancer. Angiogenic mediators include basic FGF, VEGF, angiopoietins, angiostatin, endostatin, TNFα, TNP-470, thrombospondin-1, platelet factor 4, CAI, and certain members of the integrin family of proteins. One category of this type of medicament is a metalloproteinase inhibitor, which inhibits the enzymes used by the cancer cells to exist the primary tumor site and extravasate into another tissue.

Immunotherapeutic agents are medicaments which derive from antibodies or antibody fragments which specifically bind or recognize a cancer antigen. As used herein a cancer antigen is broadly defined as an antigen expressed by a cancer cell. Preferably, the antigen is expressed at the cell surface of the cancer cell. Even more preferably, the antigen is one which is not expressed by normal cells, or at least not expressed to the same level as in cancer cells. Antibody-based immunotherapies may function by binding to the cell surface of a cancer cell and thereby stimulate the endogenous immune system to attack the cancer cell. Another way in which antibody-based therapy functions is as a delivery system for the specific targeting of toxic substances to cancer cells. Antibodies are usually conjugated to toxins such as ricin (e.g., from castor beans), calicheamicin and maytansinoids, to radioactive isotopes such as Iodine-131 and Yttrium-90, to chemotherapeutic agents (as described herein), or to biological response modifiers. In this way, the toxic substances can be concentrated in the region of the cancer and non-specific toxicity to normal cells can be minimized. In addition to the use of antibodies which are specific for cancer antigens, antibodies which bind to vasculature, such as those which bind to endothelial cells, are also useful in the invention. This is because generally solid tumors are dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

The use of immunostimulatory nucleic acids in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The nucleic acids when used in combination with monoclonal antibodies serve to reduce the dose of the antibody required to achieve a biological result.

Examples of cancer immunotherapies which are currently being used or which are in development are listed in Table 2.

TABLE 2

Cancer Immunotherapies in Development or on the Market

| MARKETER | BRAND NAME (GENERIC NAME) | INDICATION |
|---|---|---|
| IDEC/Genentech, Inc./Hoffmann-LaRoche (first monoclonal antibody licensed for the treatment of cancer in the U.S.) | Rituxan ™ (rituximab, Mabthera) (IDEC-C2B8, chimeric murine/human anti-CD20 MAb) | non-Hodgkin's lymphoma |
| Genentech/Hoffmann-La Roche | Herceptin, anti-Her2 hMAb | Breast/ovarian |
| Cytogen Corp. | Quadramet (CYT-424) radiotherapeutic agent | Bone metastases |
| Centocor/Glaxo/Ajinomoto | Panorex ® (17-1A) (murine monoclonal antibody) | Adjuvant therapy for colorectal (Dukes-C) |
| Centocor/Ajinomoto | Panorex ® (17-1A) (chimeric murine monoclonal antibody) | Pancreatic, lung, breast, ovary |
| IDEC | IDEC-Y2B8 (murine, anti-CD20 MAb labeled with Yttrium-90) | non-Hodgkin's lymhoma |
| ImClone Systems | BEC2 (anti-idiotypic MAb, mimics the $GD_3$ epitope) (with BCG) | Small cell lung |
| ImClone Systems | C225 (chimeric monoclonal antibody to epidermal growth factor receptor (EGFr)) | Renal cell |
| Techniclone International/Alpha Therapeutics | Oncolym (Lym-1 monoclonal antibody linked to 131 iodine) | non-Hodgkin's lymphoma |
| Protein Design Labs | SMART M195 Ab, humanized | Acute myleoid leukemia |
| Techniclone Corporation/Cambridge Antibody Technology | $^{131}$I LYM-1 (Oncolym ™) | non-Hodgkin's lymphoma |
| Aronex Pharmaceuticals, Inc. | ATRAGEN ® | Acute promyelocytic leukemia |
| ImClone Systems | C225 (chimeric anti-EGFr monoclonal antibody) + cisplatin or radiation | Head & neck, non-small cell lung cancer |
| Altarex, Canada | Ovarex (B43.13, anti-idiotypic CA125, mouse MAb) | Ovarian |
| Coulter Pharma (Clinical results have been positive, but the drug has been associated with significant bone marrow toxicity) | Bexxar (anti-CD20 Mab labeled with $^{131}$I) | non-Hodgkin's lymphoma |
| Aronex Pharmaceuticals, Inc. | ATRAGEN ® | Kaposi's sarcoma |
| IDEC Pharmaceuticals Corp./Genentech | Rituxan ™ (MAb against CD20) pan-B Ab in combo. with chemotherapy | B cell lymphoma |
| LeukoSite/Ilex Oncology | LDP-03, huMAb to the leukocyte antigen CAMPATH | Chronic lymphocytic leukemia (CLL) |
| Center of Molecular Immunology | ior t6 (anti CD6, murine MAb) CTCL | Cancer |

TABLE 2-continued

Cancer Immunotherapies in Development or on the Market

| MARKETER | BRAND NAME (GENERIC NAME) | INDICATION |
|---|---|---|
| Medarex/Novartis | MDX-210 (humanized anti-HER-2 bispecific antibody) | Breast, ovarian |
| Medarex/Novartis | MDX-210 (humanized anti-HER-2 bispecific antibody) | Prostate, non-small cell lung, pancreatic, breast |
| Medarex | MDX-11 (complement activating receptor (CAR) monoclonal antibody) | Acute myelogenous leukemia (AML) |
| Medarex/Novartis | MDX-210 (humanized anti-HER-2 bispecific antibody) | Renal and colon |
| Medarex | MDX-11 (complement activating receptor (CAR) monoclonal antibody) | Ex vivo bone marrow purging in acute myelogenous leukemia (AML) |
| Medarex | MDX-22 (humanized bispecific antibody, MAb-conjugates) (complement cascade activators) | Acute myeloid leukemia |
| Cytogen | OV103 (Yttrium-90 labelled antibody) | Ovarian |
| Cytogen | OV103 (Yttrium-90 labelled antibody) | Prostate |
| Aronex Pharmaceuticals, Inc. | ATRAGEN ® | non-Hodgkin's lymphoma |
| Glaxo Wellcome plc | 3622W94 MAb that binds to EGP40 (17-1A) pancarcinoma antigen on adenocarcinomas | non-small cell lung, prostate (adjuvant) |
| Genentech | Anti-VEGF, RhuMAb (inhibits angiogenesis) | Lung, breast, prostate, colorectal |
| Protein Design Labs | Zenapax (SMART Anti-Tac (IL-2 receptor) Ab, humanized) | Leukemia, lymphoma |
| Protein Design Labs | SMART M195 Ab, humanized | Acute promyelocytic leukemia |
| ImClone Systems | C225 (chimeric anti-EGFr monoclonal antibody) + taxol | Breast |
| ImClone Systems (licensed from RPR) | C225 (chimeric anti-EGFr monoclonal antibody) + doxorubicin | prostate |
| ImClone Systems | C225 (chimeric anti-EGFr monoclonal antibody) + adriamycin | prostate |
| ImClone Systems | BEC2 (anti-idiotypic MAb, mimics the $GD_3$ epitope) | Melanoma |
| Medarex | MDX-210 (humanized anti-HER-2 bispecific antibody) | Cancer |
| Medarex | MDX-220 (bispecific for tumors that express TAG-72) | Lung, colon, prostate, ovarian, endometrial, pancreatic and gastric |
| Medarex/Novartis | MDX-210 (humanized anti-HER-2 bispecific antibody) | Prostate |
| Medarex/Merck KgaA | MDX-447 (humanized anti-EGF receptor bispecific antibody) | EGF receptor cancers (head & neck, prostate, lung, bladder, cervical, ovarian) |
| Medarex/Novartis | MDX-210 (humanized anti-HER-2 bispecific antibody) | Comb. Therapy with G-CSF for various cancers, esp. breast |
| IDEC | MELIMMUNE-2 (murine monoclonal antibody therapeutic vaccine) | Melanoma |
| IDEC | MELIMMUNE-1 (murine monoclonal antibody therapeutic vaccine) | Melanoma |
| Immunomedics, Inc. | CEACIDE ™ (I-131) | Colorectal and other |
| NeoRx | Pretarget ™ radioactive antibodies | non-Hodgkin's B cell lymphoma |
| Novopharm Biotech, Inc. | NovoMAb-G2 (pancarcinoma specific Ab) | Cancer |
| Techniclone Corporation/ Cambridge Antibody Technology | TNT (chimeric MAb to histone antigens) | Brain |
| Techniclone International/ Cambridge Antibody Technology | TNT (chimeric MAb to histone antigens) | Brain |
| Novopharm | Gliomab-H (Monoclonals - Humanized Abs) | Brain, melanomas, neuroblastomas |
| Genetics Institute/AHP | GNI-250 Mab | Colorectal |
| Merck KgaA | EMD-72000 (chimeric-EGF antagonist) | Cancer |
| Immunomedics | LymphoCide (humanized LL2 antibody) | non-Hodgkin's B-cell lymphoma |
| Immunex/AHP | CMA 676 (monoclonal antibody conjugate) | Acute myelogenous leukemia |

TABLE 2-continued

Cancer Immunotherapies in Development or on the Market

| MARKETER | BRAND NAME (GENERIC NAME) | INDICATION |
|---|---|---|
| Novopharm Biotech, Inc. | Monopharm-C | Colon, lung, pancreatic |
| Novopharm Biotech, Inc. | 4B5 anti-idiotype Ab | Melanoma, small-cell lung |
| Center of Molecular Immunology | ior egf/r3 (anti EGF-R humanized Ab) | Radioimmunotherapy |
| Center of Molecular Immunology | ior c5 (murine MAb colorectal) for radioimmunotherapy | Colorectal |
| Creative BioMolecules/Chiron | BABS (biosynthetic antibody binding site) Proteins | Breast cancer |
| ImClone Systems/Chugai | FLK-2 (monoclonal antibody to fetal liver kinase-2 (FLK-2)) | Tumor-associated angiogenesis |
| ImmunoGen, Inc. | Humanized MAb/small-drug conjugate | Small-cell lung |
| Medarex, Inc. | MDX-260 bispecific, targets GD-2 | Melanoma, glioma, neuroblastoma |
| Procyon Biopharma, Inc. | ANA Ab | Cancer |
| Protein Design Labs | SMART 1D10 Ab | B-cell lymphoma |
| Protein Design Labs/Novartis | SMART ABL 364 Ab | Breast, lung, colon |
| Immunomedics, Inc. | ImmuRAIT-CEA | Colorectal |

Yet other types of chemotherapeutic agents which can be used according to the invention include Aminoglutethimide, Asparaginase, Busulfan, Carboplatin, Chlorambucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

Cancer vaccines are medicaments which are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

Although cancer vaccines may take one of several forms, as discussed infra, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. Lysates of tumor cells can also be used as cancer vaccines to elicit an immune response. Another form cancer vaccine is a peptide vaccine which uses cancer-specific or cancer-associated small proteins to activate T cells. Cancer-associated proteins are proteins which are not exclusively expressed by cancer cells (i.e., other normal cells may still express these antigens). However, the expression of cancer-associated antigens is generally consistently upregulated with cancers of a particular type. Yet another form of cancer vaccine is a dendritic cell vaccine which includes whole dendritic cells which have been exposed to a cancer antigen or a cancer-associated antigen in vitro. Lysates or membrane fractions of dendritic cells may also be used as cancer vaccines. Dendritic cell vaccines are able to activate antigen-presenting cells directly. Other cancer vaccines include ganglioside vaccines, heat-shock protein vaccines, viral and bacterial vaccines, and nucleic acid vaccines.

The use of immunostimulatory nucleic acids in conjunction with cancer vaccines provides an improved antigen-specific humoral and cell mediated immune response, in addition to activating NK cells and endogenous dendritic cells, and increasing IFN$\alpha$ levels. This enhancement allows a vaccine with a reduced antigen dose to be used to achieve the same beneficial effect. In some instances, cancer vaccines may be used along with adjuvants, such as those described above.

Other vaccines take the form of dendritic cells which have been exposed to cancer antigens in vitro, have processed the antigens and are able to express the cancer antigens at their cell surface in the context of MHC molecules for effective antigen presentation to other immune system cells.

The immunostimulatory nucleic acids are used in one aspect of the invention in conjunction with cancer vaccines which are dendritic cell based. A dendritic cell is a professional antigen presenting cell. Dendritic cells form the link between the innate and the acquired immune system by presenting antigens and through their expression of pattern recognition receptors which detect microbial molecules like LPS in their local environment. Dendritic cells efficiently internalize, process, and present soluble specific antigen to which it is exposed. The process of internalizing and presenting antigen causes rapid upregulation of the expression of major histocompatibility complex (MHC) and costimulatory molecules, the production of cytokines, and migration toward lymphatic organs where they are believed to be involved in the activation of T cells.

Table 3 lists a variety of cancer vaccines which are either currently being used or are in development.

TABLE 3

Cancer Vaccines in Development or on the Market

| MARKETER | BRAND NAME (GENERIC NAME) | INDICATION |
| --- | --- | --- |
| Center of Molecular Immunology | EGF | Cancer |
| Center of Molecular Immunology | | Ganglioside cancer vaccine |
| Center of Molecular Immunology | Anti-idiotypic | Cancer vaccine |
| ImClone Systems/Memorial Sloan-Kettering Cancer Center | Gp75 antigen | Melanoma |
| ImClone Systems/Memorial Sloan-Kettering Cancer Center | Anti-idiotypic Abs | Cancer vaccines |
| Progenics Pharmaceuticals, Inc. | GMK melanoma vaccine | Melanoma |
| Progenics Pharmaceuticals, Inc, | MGV ganglioside conjugate vaccine | Lymphoma, colorectal, lung |
| Corixa | Her2/neu | Breast, ovarian |
| AltaRex | Ovarex | Ovarian |
| AVAX Technologies Inc. | M-Vax, autologous whole cell | Melanoma |
| AVAX Technologies Inc. | O-Vax, autologous whole cell | Ovarian |
| AVAX Technologies Inc. | L-Vax, autologous whole cell | Leukemia-AML |
| Biomira Inc./Chiron | Theratope, STn-KLH | Breast, Colorectal |
| Biomira Inc. | BLP25, MUC-1 peptide vaccine encapsulated in liposomal delivery system | Lung |
| Biomira Inc. | BLP25, MUC-1 peptide vaccine encapsulated in liposomal delivery system + Liposomal IL-2 | Lung |
| Biomira Inc. | Liposomal idiotypic vaccine | Lymphoma B-cell malignancies |
| Ribi Immunochem | Melacine, cell lysate | Melanoma |
| Corixa | Peptide antigens, microsphere delivery sysem and LeIF adjuvant | Breast |
| Corixa | Peptide antigens, microsphere delivery sysem and LeIF adjuvant | Prostate |
| Corixa | Peptide antigens, microsphere delivery sysem and LeIF adjuvant | Ovarian |
| Corixa | Peptide antigens, microsphere delivery sysem and LeIF adjuvant | Lymphoma |
| Corixa | Peptide antigens, microsphere delivery sysem and LeIF adjuvant | Lung |
| Virus Research Institute | Toxin/antigen recombinant delivery system | All cancers |
| Apollon Inc. | Genevax-TCR | T-cell lymphoma |
| Bavarian Nordic Research Institute A/S | MVA-based (vaccinia virus) vaccine | Melanoma |
| BioChem Pharma/BioChem Vaccine | PACIS, BCG vaccine | Bladder |
| Cantab Pharmaceuticals | TA-HPV | Cervical |
| Cantab Pharmaceuticals | TA-CIN | Cervical |
| Cantab Pharmaceuticals | DISC-Virus, immunotherapy | Cancer |
| Pasteur Merieux Connaught | ImmuCyst ® /TheraCys ® - B CG Immunotherapeutic (Bacillus Calmette-Guerin/Connaught), for intravesical treatment of superficial bladder cancer | Bladder |

As used herein, chemotherapeutic agents embrace all other forms of cancer medicaments which do not fall into the categories of immunotherapeutic agents or cancer vaccines. Chemotherapeutic agents as used herein encompass both chemical and biological agents. These agents function to inhibit a cellular activity which the cancer cell is dependent upon for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. Combination chemotherapy and immunostimulatory nucleic acid administration increases the maximum tolerable dose of chemotherapy.

Chemotherapeutic agents which are currently in development or in use in a clinical setting are shown in Table 4.

TABLE 4

Cancer Drugs in Development or on the Market

| Marketer | Brand Name | Generic Name | Indication |
|---|---|---|---|
| Abbott | TNP 470/AGM 1470 | Fragyline | Anti-Angiogenesis in Cancer |
| Takeda | TNP 470/AGM 1470 | Fragyline | Anti-Angiogenesis in Cancer |
| Scotia | Meglamine GLA | Meglamine GLA | Bladder Cancer |
| Medeva | Valstar | Valrubicin | Bladder Cancer - Refractory in situ carcinoma |
| Medeva | Valstar | Valrubicin | Bladder Cancer - Papillary Cancer |
| Rhone Poulenc | Gliadel Wafer | Carmustaine + Polifepr Osan | Brain Tumor |
| Warner Lambert | Undisclosed Cancer (b) | Undisclosed Cancer (b) | Cancer |
| Bristol Myers Squib | RAS Farnesyl Transferase Inhibitor | RAS FarnesylTransferase Inhibitor | Cancer |
| Novartis | MMI 270 | MMI 270 | Cancer |
| Bayer | BAY 12-9566 | BAY 12-9566 | Cancer |
| Merck | Farnesyl Transferase Inhibitor | Farnesyl Transferase Inhibitor | Cancer (Solid tumors - pancrease, colon, lung, breast) |
| Pfizer | PFE | MMP | Cancer, angiogenesis |
| Pfizer | PFE | Tyrosine Kinase | Cancer, angiogenesis |
| Lilly | MTA/LY 231514 | MTA/LY 231514 | Cancer Solid Tumors |
| Lilly | LY 264618/Lometexol | Lometexol | Cancer Solid Tumors |
| Scotia | Glamolec | LiGLA (lithium-gamma linolenate) | Cancer, pancreatic, breast, colon |
| Warner Lambert | CI-994 | CI-994 | Cancer, Solid Tumors/Leukemia |
| Schering AG | Angiogenesis inhibitor | Angiogenesis Inhibitor | Cancer/Cardio |
| Takeda | TNP-470 | n/k | Malignant Tumor |
| Smithkline Beecham | Hycamtin | Topotecan | Metastatic Ovarian Cancer |
| Novartis | PKC 412 | PKC 412 | Multi-Drug Resistant Cancer |
| Novartis | Valspodar | PSC 833 | Myeloid Leukemia/Ovarian Cancer |
| Immunex | Novantrone | Mitoxantrone | Pain related to hormone refractory prostate cancer. |
| Warner Lambert | Metaret | Suramin | Prostate |
| Genentech | Anti-VEGF | Anti-VEGF | Prostate/Breast/Colorectal/NSCL Cancer |
| British Biotech | Batimastat | Batimastat (BB94) | Pterygium |
| Eisai | E 7070 | E 7070 | Solid Tumors |
| Biochem Pharma | BCH-4556 | BCH-4556 | Solid Tumors |
| Sankyo | CS-682 | CS-682 | Solid Tumors |
| Agouron | AG2037 | AG2037 | Solid Tumors |
| IDEC Pharma | 9-AC | 9-AC | Solid Tumors |
| Agouron | VEGF/b-FGF Inhibitors | VEGF/b-FGF Inhibitors | Solid Tumors |
| Agouron | AG3340 | AG3340 | Solid Tumors/Macular Degen |
| Vertex | Incel | VX-710 | Solid Tumors - IV |
| Vertex | VX-853 | VX-853 | Solid Tumors - Oral |
| Zeneca | ZD 0101 (inj) | ZD 0101 | Solid Tumors |
| Novartis | ISI 641 | ISI 641 | Solid Tumors |
| Novartis | ODN 698 | ODN 698 | Solid Tumors |
| Tanube Seiyaku | TA 2516 | Marimistat | Solid Tumors |
| British Biotech | Marimastat | Marimastat (BB 2516) | Solid Tumors |
| Celltech | CDP 845 | Aggrecanase Inhibitor | Solid Tumors/Breast Cancer |
| Chiroscience | D2163 | D2163 | Solid Tumors/Metastases |
| Warner Lambert | PD 183805 | PD 183805 | |
| Daiichi | DX8951f | DX8951f | Anti-Cancer |
| Daiichi | Lemonal DP 2202 | Lemonal DP 2202 | Anti-Cancer |
| Fujisawa | FK 317 | FK 317 | Anticancer Antibiotic |
| Chugai | Picibanil | OK-432 | Antimalignant Tumor |
| Nycomed Amersham | AD 32/valrubicin | Valrubicin | Bladder Cancer-Refractory Insitu Carcinoma |
| Nycomed Amersham | Metastron | Strontium Derivative | Bone Cancer (adjunt therapy, Pain) |
| Schering Plough | Temodal | Temozolomide | Brain Tumours |
| Schering Plough | Temodal | Temozolonide | Brain Tumours |
| Liposome | Evacet | Doxorubicin, Liposomal | Breast Cancer |
| Nycomed Amersham | Yewtaxan | Paclitaxel | Breast Cancer Advanced, Ovarian Cancer Advanced |
| Bristol Myers Squib | Taxol | Paclitaxel | Breast Cancer Advanced, Ovarian Cancer Advanced, NSCLC |

TABLE 4-continued

Cancer Drugs in Development or on the Market

| Marketer | Brand Name | Generic Name | Indication |
| --- | --- | --- | --- |
| Roche | Xeloda | Capecitabine | Breast Cancer, Colorectal Cancer |
| Roche | Furtulon | Doxifluridine | Breast Cancer, Colorectal Cancer, Gastric Cancer |
| Pharmacia & Upjohn | Adriamycin | Doxorubicin | Breast Cancer, Leukemia |
| Ivax | Cyclopax | Paclitaxel, Oral | Breast/Ovarian Cancer |
| Rhone Poulenc | Oral Taxoid | Oral Taxoid | Broad Cancer |
| AHP | Novantrone | Mitoxantrone | Cancer |
| Sequus | SPI-077 | Cisplatin, Stealth | Cancer |
| Hoechst | HMR 1275 | Flavopiridol | Cancer |
| Pfizer | CP-358, 774 | EGFR | Cancer |
| Pfizer | CP-609, 754 | RAS Oncogene Inhibitor | Cancer |
| Bristol Myers Squib | BMS-182751 | Oral Platinum | Cancer (Lung, Ovarian) |
| Bristol Myers Squib | UFT (Tegafur/Uracil) | UFT (Tegafur/Uracil) | Cancer Oral |
| Johnson & Johnson | Ergamisol | Levamisole | Cancer Therapy |
| Glaxo Wellcome | Eniluracil/776C85 | 5FU Enhancer | Cancer, Refractory Solid & Colorectal Cancer |
| Johnson & Johnson | Ergamisol | Levamisole | Colon Cancer |
| Rhone Poulenc | Campto | Irinotecan | Colorectal Cancer, Cervical Cancer |
| Pharmacia & Upjohn | Camptosar | Irinotecan | Colorectal Cancer, Cervical Cancer |
| Zeneca | Tomudex | Ralitrexed | Colorectal Cancer, Lung Cancer, Breast Cancer |
| Johnson & Johnson | Leustain | Cladribine | Hairy Cell Leukaemia |
| Ivax | Paxene | Paclitaxel | Kaposi Sarcoma |
| Sequus | Doxil | Doxorubicin, Liposomal | KS/Cancer |
| Sequus | Caelyx | Doxorubicin, Liposomal | KS/Cancer |
| Schering AG | Fludara | Fludarabine | Leukaemia |
| Pharmacia & Upjohn | Pharmorubicin | Epirubicin | Lung/Breast Cancer |
| Chiron | DepoCyt | DepoCyt | Neoplastic Meningitis |
| Zeneca | ZD1839 | ZD 1839 | Non Small Cell Lung Cancer, Pancreatic Cancer |
| BASF | LU 79553 | Bis-Naphtalimide | Oncology |
| BASF | LU 103793 | Dolastain | Oncology |
| Shering Plough | Caetyx | Doxorubicin-Liposome | Ovarian/Breast Cancer |
| Lilly | Gemzar | Gemcitabine | Pancreatic Cancer, Non Small Cell Lung Cancer, Breast, Bladder and Ovarian |
| Zeneca | ZD 0473/Anormed | ZD 0473/Anormed | Platinum based NSCL, ovarian etc. |
| Yamanouchi | YM 116 | YM 116 | Prostate Cancer |
| Nycomed Amersham | Seeds/I-125 Rapid St | Lodine Seeds | Prostate Cancer |
| Agouron | Cdk4/cdk2 inhibitors | cdk4/cdk2 inhibitors | Solid Tumors |
| Agouron | PARP inhibitors | PARP Inhibitors | Solid Tumors |
| Chiroscience | D4809 | Dexifosamide | Solid Tumors |
| Bristol Myers Squib | UFT (Tegafur/Uracil) | UFT (Tegafur/Uracil) | Solid Tumors |
| Sankyo | Krestin | Krestin | Solid Tumors |
| Asta Medica | Ifex/Mesnex | Ifosamide | Solid Tumors |
| Bristol Meyers Squib | Ifex/Mesnex | Ifosamide | Solid Tumors |
| Bristol Myers Squib | Vumon | Teniposide | Solid Tumors |
| Bristol Myers Squib | Paraplatin | Carboplatin | Solid Tumors |
| Bristol Myers Squib | Plantinol | Cisplatin, Stealth | Solid Tumors |
| Bristol Myers Squib | Plantinol | Cisplatin | Solid Tumors |
| Bristol Myers Squib | Vepeside | Etoposide | Solid Tumors Melanoma |
| Zeneca | ZD 9331 | ZD 9331 | Solid Tumors, Advanced Colorectal |
| Chugai | Taxotere | Docetaxel | Solid Tumors, Breast Cancer |

TABLE 4-continued

Cancer Drugs in Development or on the Market

| Marketer | Brand Name | Generic Name | Indication |
| --- | --- | --- | --- |
| Rhone Poulenc | Taxotere | Docetaxel | Solid Tumors, Breast Cancer |
| Glaxo Wellcome | Prodrug of guanine arabinside | Prodrug of arabinside | T Cell Leukemia/Lymphoma & B Cell Neoplasm |
| Bristol Myers Squib | Taxane Analog | Taxane Analog | Taxol follow up |

In one embodiment, the methods of the invention use immunostimulatory nucleic acids as a replacement to the use of IFNα therapy in the treatment of cancer. Currently, some treatment protocols call for the use of IFNα. Since IFNα is produced following the administration of some immunostimulatory nucleic acids, these nucleic acids can be used to generate IFNα endogenously.

In another embodiment, the asthma/allergy medicament is a medicament selected from the group consisting of PDE-4 inhibitor, bronchodilator/beta-2 agonist, K+ channel opener, VLA-4 antagonist, neurokin antagonist, TXA2 synthesis inhibitor, xanthanine, arachidonic acid antagonist, 5 lipoxygenase inhibitor, thromboxin A2 receptor antagonist, thromboxane A2 antagonist, inhibitor of 5-lipox activation protein, and protease inhibitor, but is not so limited. In some important embodiments, the asthma/allergy medicament is a Bronchodilator/beta-2 agonist selected from the group consisting of salmeterol, salbutamol, terbutaline, D2522/formoterol, fenoterol, and orciprenaline.

In another embodiment, the asthma/allergy medicament is a medicament selected from the group consisting of anti-histamines and prostaglandin inducers. In one embodiment, the anti-histamine is selected from the group consisting of loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, and HSR 609. In another embodiment, the prostaglandin inducer is S-5751.

In yet another embodiment, the asthma/allergy medicament is selected from the group consisting of steroids and immunomodulators. The immunomodulators may be selected from the group consisting of anti-inflammatory agents, leukotriene antagonists, IL-4 muteins, soluble IL-4 receptors, immunosuppressants, anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and downregulators of IgE, but are not so limited. In one embodiment, the downregulator of IgE is an anti-IgE. In another embodiment, the steroid is selected from the group consisting of beclomethasone, fluticasone, tramcinolone, budesonide, and budesonide. In still a further embodiment, the immunosuppressant is a tolerizing peptide vaccine.

In one embodiment, the immunostimulatory nucleic acid is administered concurrently with the asthma/allergy medicament. In another embodiment, the subject is an immunocompromised subject.

Immunostimulatory nucleic acids can be combined with yet other therapeutic agents such as adjuvants to enhance immune responses. The immunostimulatory nucleic acid and other therapeutic agent may be administered simultaneously or sequentially. When the other therapeutic agents are administered simultaneously they can be administered in the same or separate formulations, but are administered at the same time. The other therapeutic agents are administered sequentially with one another and with immunostimulatory nucleic acid, when the administration of the other therapeutic agents and the immunostimulatory nucleic acid is temporally separated. The separation in time between the administration of these compounds may be a matter of minutes or it may be longer. Other therapeutic agents include but are not limited to adjuvants, cytokines, antibodies, antigens, etc.

The compositions of the invention may also comprise a non-nucleic acid adjuvants. A non-nucleic acid adjuvant is any molecule or compound except for the immunostimulatory nucleic acids described herein which can stimulate the humoral and/or cellular immune response. Non-nucleic acid adjuvants include, for instance, adjuvants that create a depot effect, immune stimulating adjuvants, and adjuvants that create a depot effect and stimulate the immune system.

An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An immune stimulating adjuvant is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the $21^{st}$ peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified *Leishmania* protein; Corixa Corporation, Seattle, Wash.).

Adjuvants that create a depot effect and stimulate the immune system are those compounds which have both of the above-identified functions. This class of adjuvants includes but is not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The immunostimulatory nucleic acids are themselves useful as adjuvants for inducing a humoral immune response. Thus they can be delivered to a subject exposed to an antigen to produce an enhanced immune response to the antigen.

The immunostimulatory nucleic acids are useful as mucosal adjuvants. It has previously been discovered that both systemic and mucosal immunity are induced by mucosal delivery of CpG nucleic acids. The systemic immunity induced in response to CpG nucleic acids included both humoral and cell-mediated responses to specific antigens that were not capable of inducing systemic immunity when administered alone to the mucosa. Furthermore, both CpG nucleic acids and cholera toxin (CT, a mucosal adjuvant that induces a Th2-like response) induced CTL. This was surprising since with systemic immunization, the presence of Th2-like antibodies is normally associated with a lack of CTL (Schirmbeck et al., 1995). Based on the results presented herein it is expected that the immunostimulatory nucleic acids will function in a similar manner.

Additionally, the immunostimulatory nucleic acids induce a mucosal response at both local (e.g., lung) and remote (e.g., lower digestive tract) mucosal sites. Significant levels of IgA antibodies are induced at distant mucosal sites by the immunostimulatory nucleic acids. CT is generally considered to be a highly effective mucosal adjuvant. As has been previously reported (Snider 1995), CT induces predominantly IgG1 isotype of antibodies, which are indicative of Th2-type response. In contrast, the immunostimulatory nucleic acids are more Th1 with predominantly IgG2a antibodies, especially after boost or when the two adjuvants are combined. Th1-type antibodies in general have better neutralizing capabilities, and furthermore, a Th2 response in the lung is highly undesirable because it is associated with asthma (Kay, 1996, Hogg, 1997). Thus the use of immunostimulatory nucleic acids as a mucosal adjuvant has benefits that other mucosal adjuvants cannot achieve. The immunostimulatory nucleic acids of the invention also are useful as mucosal adjuvants for induction of both a systemic and a mucosal immune response.

Mucosal adjuvants referred to as non-nucleic acid mucosal adjuvants may also be administered with the immunostimulatory nucleic acids. A non-nucleic acid mucosal adjuvant as used herein is an adjuvant other than a immunostimulatory nucleic acid that is capable of inducing a mucosal immune response in a subject when administered to a mucosal surface in conjunction with an antigen. Mucosal adjuvants include but are not limited to Bacterial toxins e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protine of *Neisseria meningitidis*) (Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Antigenics, Inc., Woburn, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micelle-forming agent; IDEC Pharmaceuticals Corporation, San Diego, Calif.); Syntex Adjuvant Formulation (SAF; Syntex Chemicals, Inc., Boulder, Colo.); poly[di(carboxylatophenoxy)phosphazene (PCPP polymer; Virus Research Institute, USA) and Leishmania elongation factor (Corixa Corporation, Seattle, Wash.).

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with the immunostimulatory nucleic acids. The cytokines can be administered directly with immunostimulatory nucleic acids or may be administered in the form of a nucleic acid vector that encodes the cytokine, such that the cytokine can be expressed in vivo. In one embodiment, the cytokine is administered in the form of a plasmid expression vector. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment.

Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Cytokines play a role in directing the T cell response. Helper (CD4+) T cells orchestrate the immune response of mammals through production of soluble factors that act on other immune system cells, including other T cells. Most mature CD4+T helper cells express one of two cytokine profiles: Th1 or Th2. The Th1 subset promotes delayed-type hypersensitivity, cell-mediated immunity, and immunoglobulin class switching to IgG$_{2a}$. The Th2 subset induces humoral immunity by activating B cells, promoting antibody production, and inducing class switching to IgG$_1$ and IgE. In some embodiments, it is preferred that the cytokine be a Th1 cytokine.

The immunostimulatory nucleic acids may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell (e.g., B cell surfaces and/or increased cellular uptake by target cells). Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

Delivery vehicles or delivery devices for delivering antigen and nucleic acids to surfaces have been described. The Immunostimulatory nucleic acid and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., *Salmonella, Escherichia coli, Bacillus calmatte-guerin, Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kukin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art and some additional examples are provided below in the discussion of vectors.

The stimulation index of a particular immunostimulatory nucleic acid can be tested in various immune cell assays. Preferably, the stimulation index of the immunostimulatory nucleic acid with regard to B cell proliferation is at least about 5, preferably at least about 10, more preferably at least about 15 and most preferably at least about 20 as determined by incorporation of $^3$H uridine in a murine B cell culture, which has been contacted with 20 μM of nucleic acid for 20 h at 37° C. and has been pulsed with 1 μCi of $^3$H uridine; and harvested and counted 4 h later as described in detail in PCT Published Patent Applications PCT/US95/01570 (WO 96/02555) and PCT/US97/19791 (WO 98/18810) claiming priority to U.S. Ser. Nos. 08/386,063 and 08/960,774, filed on Feb. 7, 1995 and Oct. 30, 1997 respectively. For use in vivo, for example, it is important that the immunostimulatory nucleic acids be capable of effectively inducing an immune response, such as, for example, antibody production. Other assays designed to test efficacy and effective amounts are described in the Examples.

Immunostimulatory nucleic acids are effective in non-rodent vertebrate. Different immunostimulatory nucleic acid can cause optimal immune stimulation depending on the type of subject and the sequence of the immunostimulatory nucleic acid. Many vertebrates have been found according to the invention to be responsive to the same class of immunostimulatory nucleic acids, sometimes referred to as human specific immunostimulatory nucleic acids. Rodents, however, respond to different nucleic acids.

As shown herein an immunostimulatory nucleic acid causing optimal stimulation in humans may not generally cause optimal stimulation in a mouse and vice versa. An immunostimulatory nucleic acid causing optimal stimulation in humans often does, however, cause optimal stimulation in other animals such as cow, horses, sheep, etc. One of skill in the art can identify the optimal nucleic acid sequences useful for a particular species of interest using routine assays described herein and/or known in the art, using the guidance supplied herein.

The term effective amount of a immunostimulatory nucleic acid refers to the amount necessary or sufficient to realize a desired biologic effect. For example, an effective amount of a immunostimulatory nucleic acid for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular immunostimulatory nucleic acid being administered, the antigen, the size of the subject, or the severity of the disease or condition. One of ordinary skill in the art can empirically determine the effective amount of a particular immunostimulatory nucleic acid and/or antigen and/or other therapeutic agent without necessitating undue experimentation.

Subject doses of the compounds described herein for mucosal or local delivery typically range from about 0.1 μg to 10 mg per administration, which depending on the application could be given daily, weekly, or monthly and any other amount of time therebetween. More typically mucosal or local doses range from about 10 μg to 5 mg per administration, and most typically from about 100 μg to 1 mg, with 2-4 administrations being spaced days or weeks apart. More typically, immune stimulant doses range from 1 μg to 10 mg per administration, and most typically 10 μg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the immunostimulatory nucleic acids are administered in combination with other therapeutic agents or in specialized delivery vehicles typically range from about 0.1 µg to 10 mg per administration, which depending on the application could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other mucosal adjuvants, e.g., LT and other antigens for vaccination purposes, for the mucosal or local administration. Higher doses are required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the immunostimulatory nucleic acid can be administered to a subject by any mode that delivers the nucleic acid to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, intratracheal, inhalation, ocular, vaginal, and rectal.

For oral administration, the compounds (i.e., immunostimulatory nucleic acids, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The immunostimulatory nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

As described in greater detail herein, the pharmaceutical compositions of the invention contain an effective amount of a immunostimulatory nucleic acid and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The immunostimulatory nucleic acids useful in the invention may be delivered in mixtures with additional adjuvant(s), other therapeutics, or antigen(s). A mixture may consist of several adjuvants in addition to the immunostimulatory nucleic acid or several antigens or other therapeutics.

A variety of administration routes are available. The particular mode selected will depend, of course, upon the particular adjuvants or antigen selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administration of doses at specific intervals of weeks or months apart is usual for boosting the antigen-specific responses.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Summary:

This report summarizes in vitro data with human cells demonstrating that ODN 10105 behaves as well or better than ODN 7909 in human cell assays. In addition, ODN 10105 behaves as well or better than ODN 7909 in in vitro and in vivo data in mice demonstrating that CpG ODN 10105 is useful in the activation of the innate immune system, and in augmenting humoral and cellular HBsAg-specific responses in mice when coadministered with the antigen.

The assays performed were receptor engagement (TLR9), B cell activation (expression of cell surface activation marker and B cell proliferation) and cytokine secretion (IL-10, IP-10 and IFN-α). All assays demonstrated that ODN 10105 has properties that were similar or superior to ODN 7909. In vitro studies (i.e. B cell proliferation assays, NK lytic activity, cytokine secretion profiles) were carried out using naïve BALB/c mouse splenocytes. In vivo comparison studies were carried out by comparing the potential of these two ODNs to enhance antigen specific immune responses to hepatitis B antigen (HBsAg).

Materials and Methods:

Human Studies
  Oligodeoxynucleotides:
  All ODNs (10105, 7909 and control ODN) were provided by Coley Pharmaceutical GmbH (Langenfeld, Germany). The control ODN contained no stimulatory CpG motif. ODNs were diluted in phosphate-buffered saline, and stored at −20° C. All dilutions were carried out using pyrogen-free reagents.
  TLR9 assay:
  Cells used for this assay were expressing the human TLR9 receptor and containing a reporter gene construct. Cells were incubated with ODNs for 16 h. Each data point was done in triplicate. Cells were lysed and assayed for reporter gene activity. Stimulation indices were calculated in reference to reporter gene activity of medium without addition of ODN.
  Cell purification:
  Peripheral blood buffy coat preparations from healthy human donors were obtained from the German Red Cross (Rathingen, Germany) and from these, PBMC were purified by centrifugation over Ficoll-Hypaque (Sigma, Germany). The purified PBMC were either used fresh or were suspended in freezing medium and stored at −70° C. When required, aliquots of these cells were thawed, washed and resuspended in RPMI 1640 culture medium supplemented with 10% (v/v) heat inactivated FCS, 1.5 mM L-glutamine, 100 U/ml penicillin and 100 µg/ml streptomycin.
  Cytokine detection:
  Thawed or fresh PBMC were resuspended at a concentration of $5\times10^6$/ml and added to 48 well flat-bottomed plates (1 ml/well), which had previously received nothing or ODN in a variety of concentrations. The cells were cultured in a humidified incubator at 37° C.
  Culture supernatants were collected after the indicated time points. If not used immediately, supernatants were frozen at −20° C. until required.
  Amounts of cytokines in the supernatants were assessed using commercially available ELISA Kits (IL-10; Diaclone, USA) or in-house ELISAs (IP-10 and IFN-α) developed using commercially available antibodies (from Pharmingen or PBL; Germany or USA, respectively).
  Cultures for flow cytometric analysis of B cell activation:
  Monoclonal antibodies to CD19 and CD86 were purchased from Becton Dickinson (Germany). PBMC were incubated for 48 hours with or without the addition of different concentrations of ODNs. B cells were identified by expression of CD19 by flow cytometry. Flow cytometric data were acquired on a FACSCalibur (Becton Dickinson). Data were analyzed using the computer program CellQuest (Becton Dickinson). Proliferating CD19 positive B cells were identified after culturing CFSE-labelled PBMC (CFSE is a fluorescing dye binding to all cell surfaces) by decreased CFSE content using flow cytometry methodology (see above).

Murine In Vitro/In Vivo Studies:
  Oligodeoxynucleotides:
  CpG ODN 7909 (GMP quality) and 10105 were supplied by Coley Pharmaceutical Inc. (Wellesley, Mass.). All ODN were re suspended in sterile, endotoxin free TE at pH 8.0 (OmniPer®; EM Science, Gibbstown, N.J.) and stored and handle under aseptic conditions to prevent both microbial and endotoxin contamination.
  Dilution of ODNs for assays was carried out in sterile, endotoxin free PBS, pH 7.2 (Sigma Chemical Company, St. Lois, Mo.).
  Animals:
  Female BALB/c mice (6-8 weeks of age) were used for all experiments. Animals were purchased from Charles River Canada (Quebec, Canada) and housed in micro isolators at the animal care facility of the Ottawa Hospital Research Institute, Civic Site.
  In vitro assays:
  Naïve BALB/c mouse splenocytes were used for all in vitro assays. Animals were anesthetized with isofluorane and euthanized by cervical dislocation. Spleens were removed under aseptic conditions and placed in PBS+0.2% bovine serum albumin (Sigma Chemical Company). Spleens were then homogenized and splenocytes were re-suspended in RPMI 1640 (Life Technologies, Grand Island, N.Y.) tissue culture medium supplemented with 2% normal mouse serum (Cedarlane Laboratories, Ontario, Canada), penicillin-streptomycin solution (final concentration of 1000 U/ml and 1 mg/ml respectively; Sigma Chemical Company), and $5\times10^{-5}$ M β-mercaptoethanol (Sigma Chemical Company).
  B cell proliferation assays:
  Spleen cell suspensions were prepared and adjusted to a final concentration of $5\times10^6$ cells per ml in complete RPMI 1640. Splenocyte suspension was plated onto 96-well U-bottom tissue culture plates (100 µl/well) along with 100 µl of each stimulant diluted to appropriate concentrations in complete RPMI 1640. The stimulants used were CpG ODN (at 1, 3, 10 µg/ml) 7909 and 10105. Concanavalin A (10 µg/ml, Sigma Chemical Company) LPS (10 µg/ml, Sigma Chemical Company) were used as positive controls and cells cultured with media alone were used as negative controls. Each splenocyte sample was plated in triplicate and cells were incubated in a humidified 5% $CO_2$ incubator at 37° C. for 96 hr. At the end of the incubation period, cells were pulsed with $^3$H-thymidine (20 µCi/ml) at 96 hr post incubation for 16 hours, harvested and measured for radioactivity.
  Cytokine secretion profiles:
  Spleen cell suspensions were prepared and plated in 96-well U-bottom tissue culture plates as described for B cell proliferation assays. Each splenocyte sample was plated in triplicate and the cells were incubated in a humidified 5%

$CO_2$ incubator at 37° C. for 6, 12 or 48 hr. At the end of the incubation period, 96-well plates were centrifuged for 5 min at 1200 rpm and culture supernatants harvested and stored at −80° C. until assayed. Commercially available assay kits (mouse OptEIA kits; PharMingen, Mississauga, ON) were used according to manufacturers instructions to assay cytokine levels in culture supernatants taken at 6 hr (TNF-α), 24 hr (IL-12) and 48 hr (IL-6 and IL-10).

NK assays:

Splenocyte suspensions were prepared as described previously and adjusted to a final concentration of $3 \times 10^6$ cells per ml in complete RPMI 1640. Splenocyte suspension (10 ml; $30 \times 10^6$ cells) was plated in T-25 tissue culture flasks (Fisher Scientific, Ottawa, ON) along with either CpG ODN (at 1, 3, 10 μg/ml) 7909 and 10105. Splenocytes cultured with media alone was used as negative controls. Each splenocyte culture was incubated in a humidified 5% $CO_2$ incubator at 37° C. for 24 hr. At the end of the incubation period, cells were plated at different effector:target ratios onto 96-well U-bottom tissue culture plates (100 μl/well) along with 100 μl of $^{51}$Cr labeled target cells at $5 \times 10^4$ cells/ml. NK sensitive mouse lymphoma cell line YAC-1 (ATCC #TIB-160, ATCC, Manassas, Va.) was used as the target cell line. Each sample was plated in triplicate and the cells were incubated in a humidified 5% $CO_2$ incubator at 37° C. for 4 hr. Target cells were incubated with media alone or with 2N HCl to determine spontaneous release and maximum release respectively. At the end of the incubation period, supernatants were harvested and radioactivity levels were determined using a γ counter. The % lysis was determined using the following formula;

$$\% \text{ specific release} = \frac{\text{experimental release} - \text{spontaneous release}}{\text{maximum release} - \text{spontaneous release}} \times 100$$

Immunization of mice:

BALB/c mice (n=10/group) were immunized with 1 μg HBsAg sub type ad (International Enzymes, CA) alone or in combination with either 10 μg CpG ODN 7909 or CpG ODN 10105. Animals were bled and boosted at 4 weeks post-primary immunization. At 1 week post boost 5 animals from each group was euthanized and spleens removed for CTL assays Determination of antibody responses:

Antibodies (total IgG, IgG1 and IgG2a) specific to HBsAg (anti-HBs) were detected and quantified by endpoint dilution ELISA assay, which was performed in triplicate on samples from individual animals. End-point titers were defined as the highest plasma dilution that resulted in an absorbance value (OD 450) two times greater than that of non-immune plasma with a cut-off value of 0.05. These were reported as group mean titers±SEM.

Statistical analysis:

Statistical analysis was performed using InStat program (Graph PAD Software, San Diego). The statistical difference between groups were determined by Student's t test (for two groups) or by 1-factor ANOVA followed by Tukey's test (for three or more groups) on raw data or transformed data ($\log_{10}$, for heteroscedastic populations).

Results:

TLR9 engagement:

Recently the receptor for the recognition of CpG sequences was identified and shown to be a member of the Toll-Like Receptor (TLR) family (Hemmi et al., 2000). This receptor, TLR9, is readily activated by ODNs containing optimal immunostimulatory CpG sequences. We incubated a cell line stably expressing the human TLR9 with different concentrations of ODNs 7909 and 10105 as well as a control ODN (FIG. 1).

The results demonstrate that there was no statistically significant difference between the two B class ODNs in activating TLR9. Both ODNs showed the same dose-response curve and reached maximum activation at the same concentrations. The control ODN used did not induce TLR9 activation even at the highest concentration of 24 μg/ml.

Figure 2:
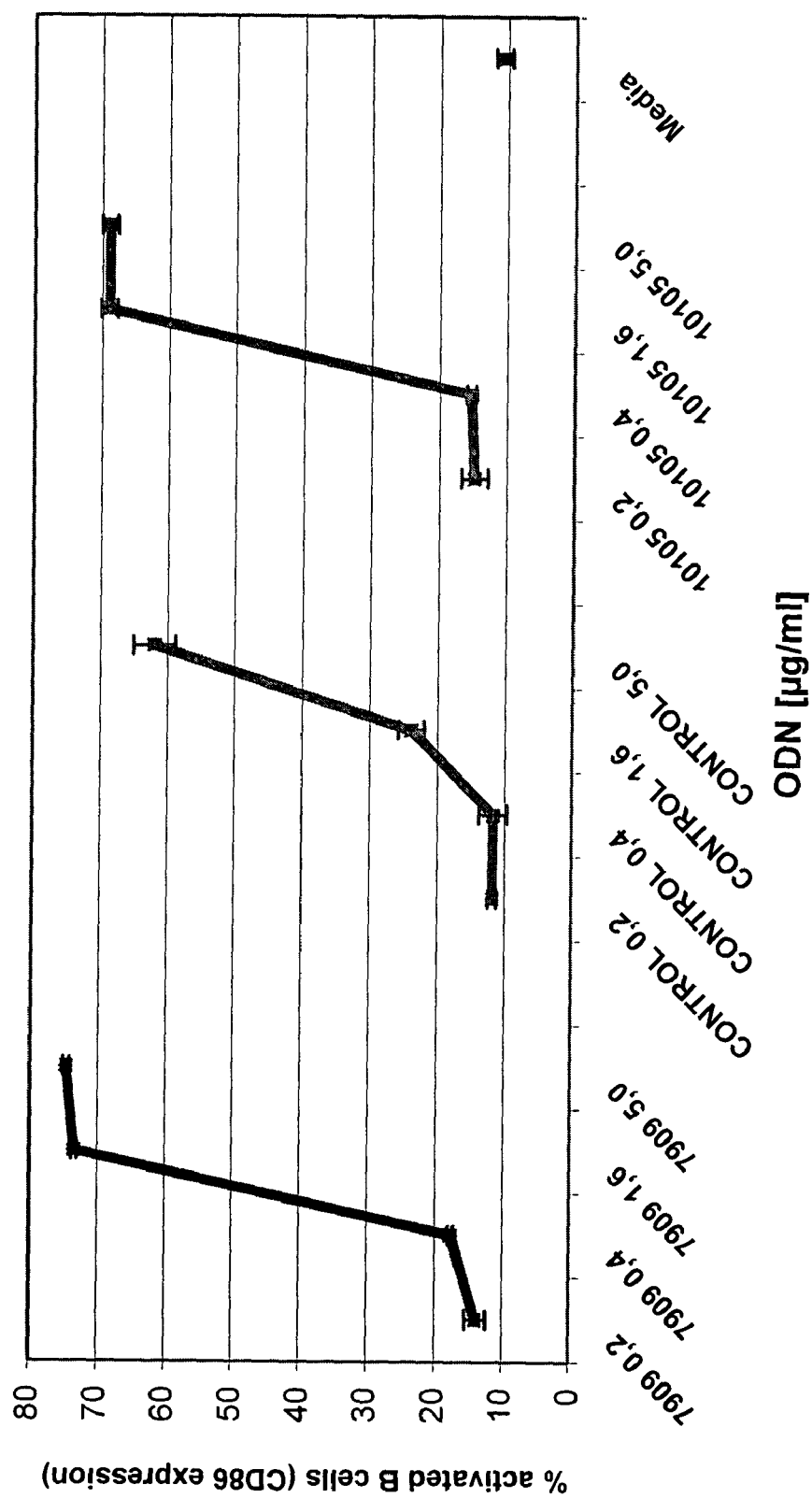
FIG. 2: B cells up regulate the activation marker CD86 upon incubation of PBMC with CpG ODNs. Human PBMC were incubated with ODNs 7909 and 10105 as well as a control ODN at the indicated concentrations for 48 h. Shown is the mean percentage of CD86 expressing CD19-positive B cells (measured by flow cytometry) of three different donors.
Figure 3:
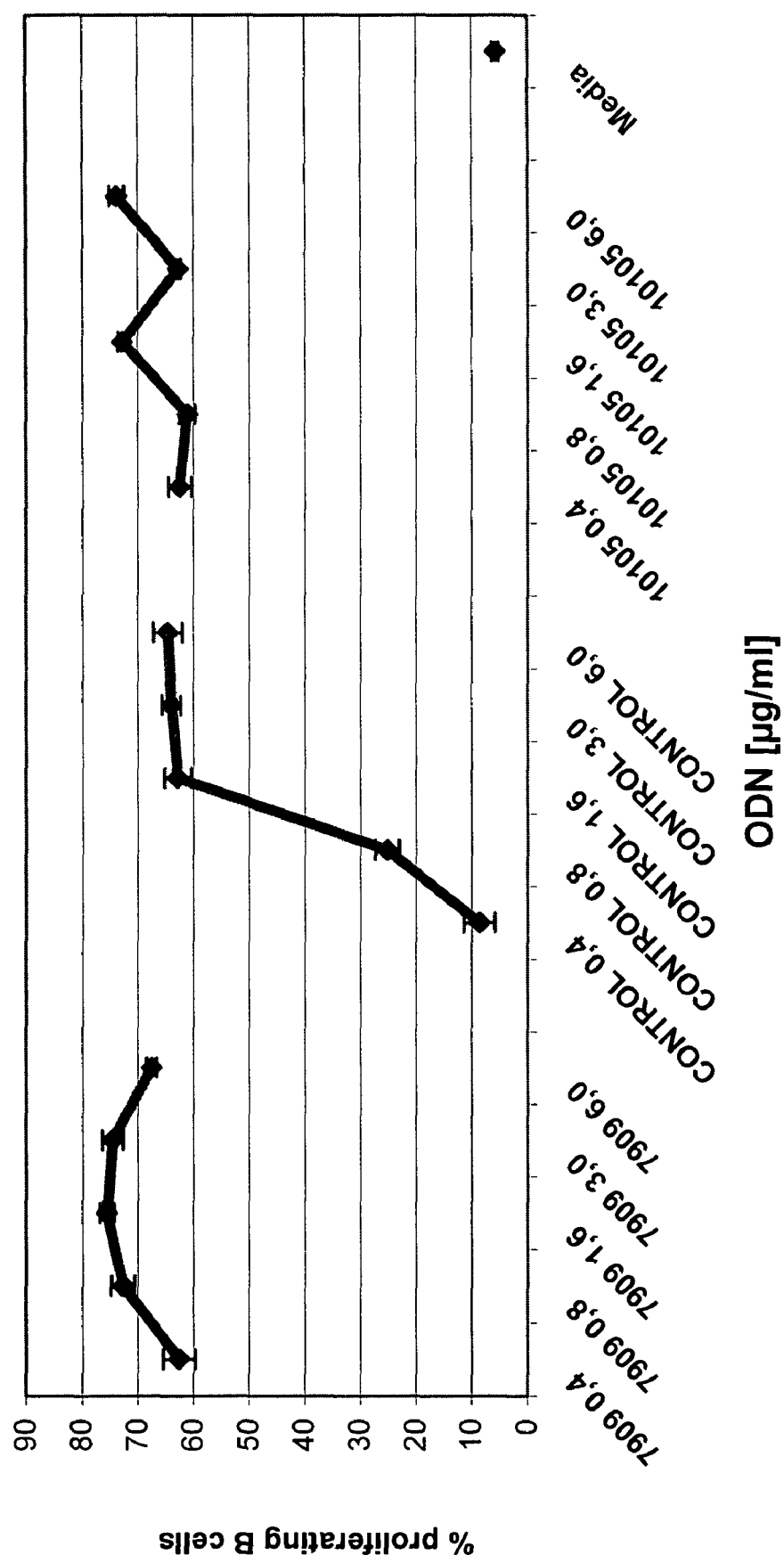
FIG. 3: Proliferation of B cells induced by CpG ODNs 7909 and 10105. PBMC pre-incubated with the dye CFSE were cultured for 5 days without or with the indicated ODN concentrations. Cells were harvested and the decrease of the CFSE stain on proliferating CD19-positive B cells was measured by flow cytometry (see also Materials and Methods).

Human B cells:

One characteristic of type B ODNs is their ability to very efficiently activate B cells (Krieg et al., 1995). B cells and plasmacytoid DC are at the moment the only immune cell types known to express TLR9 (Krug et al., 2001; Bauer et al., 2001). The direct activation of B cells induced by ODNs 7909 and 10105 was measured by up regulation of the cell surface marker CD86 (FIG. 2), and proliferation of B cells (FIG. 3). For CD86 expression on human B cells PBMC of healthy blood donors were incubated with different ODNs and B cell activation measured as described in Materials and Methods.

The results demonstrate that 10105 as well as 7909 are very potent stimulators of human B cells. FIG. 2 shows that these CpG ODNs were capable to stimulate B cells at an in vitro concentration of only 0.4 μg/ml. The plateau was reached at about 1.6 μg/ml and more than 70% of B cells were found to have up regulated CD86 in contrast to the control that was much less potent. A similar result was obtained for the induction of B cell proliferation, with exception that 10105 was able to induce B cell proliferation even at the highest dose test of 6 μg/ml, while 7909 plateaued at the dose of 1.6 to 3.0 μg/ml (FIG. 3).

Figure 4:
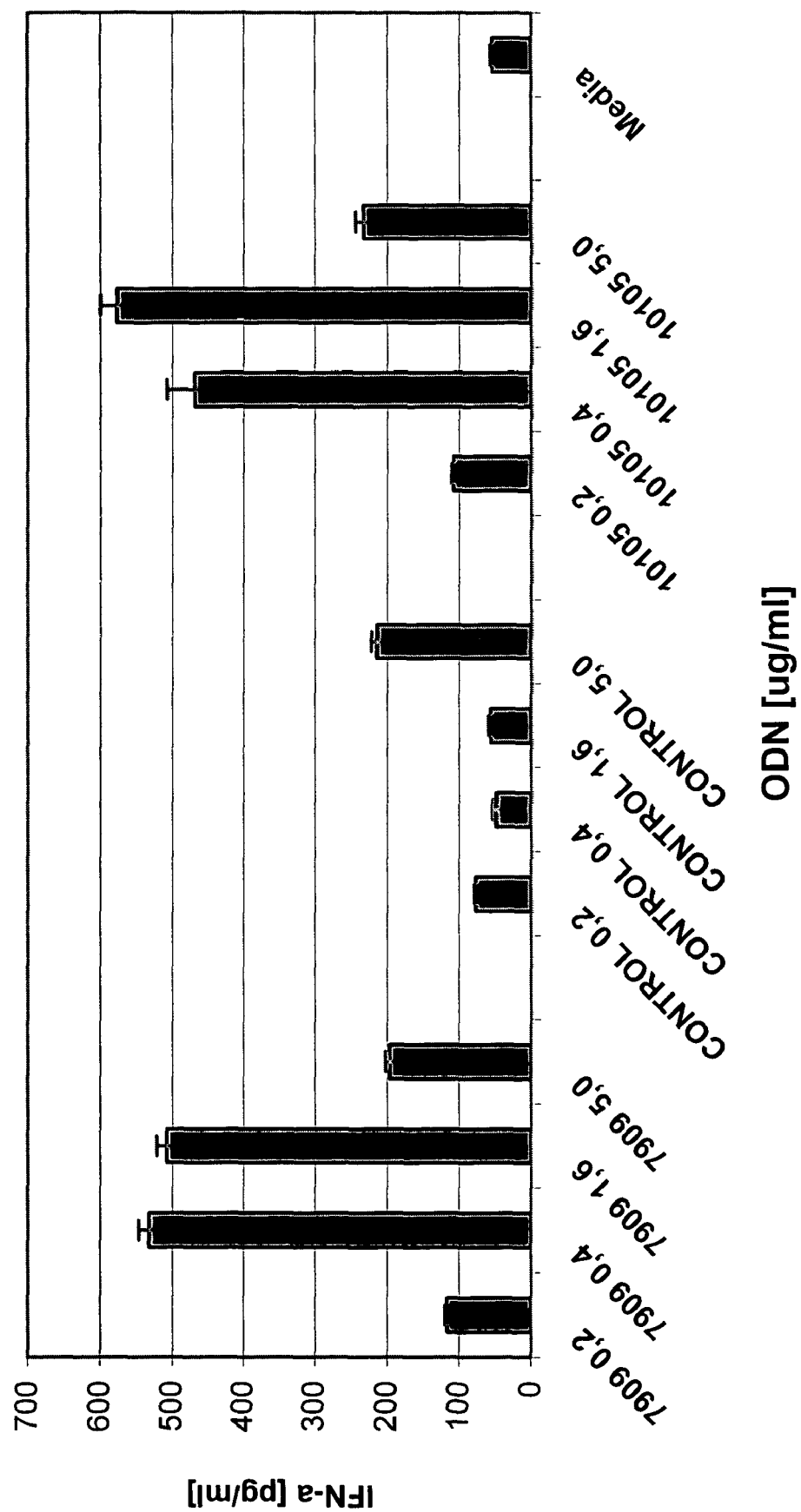
FIG. 4: IFN-α secretion induced by ODNs 7909 and 10105. Human PBMC of three different donors were incubated with the indicated concentrations of ODNs for 48 h. The supernatant was harvested and IFN-α was measured by ELISA (see Materials and Methods). Shown are the mean amounts of IFN-α obtained for the three different donors at each concentration.

Cytokine secretion:

ODNs of the B class induce a Th1 dominated immune response in vivo as well as in vitro. It was found that they are able to induce typical Th1 cytokines such as IFN-γ and IFN-α as well as chemokines such as MCP-1 and IP-10. In addition, low secretion of the pro-inflammatory cytokines IL-6 as well as TNF-α and secretion of the negative regulator IL-10 can be observed. The secretion of the Th1 cytokine IFN-α, the chemokine IP-10 as well as the regulatory cytokine IL-10 and the pro-inflammatory cytokine TNF-α were measured following administration of 10105 and 7909. FIG. 4 shows the result for an experiment performed with 6 different donors at 0.2, 0.4 and 1.6 μg/ml to measure in vitro IFN-α secretion.

Figure 5:
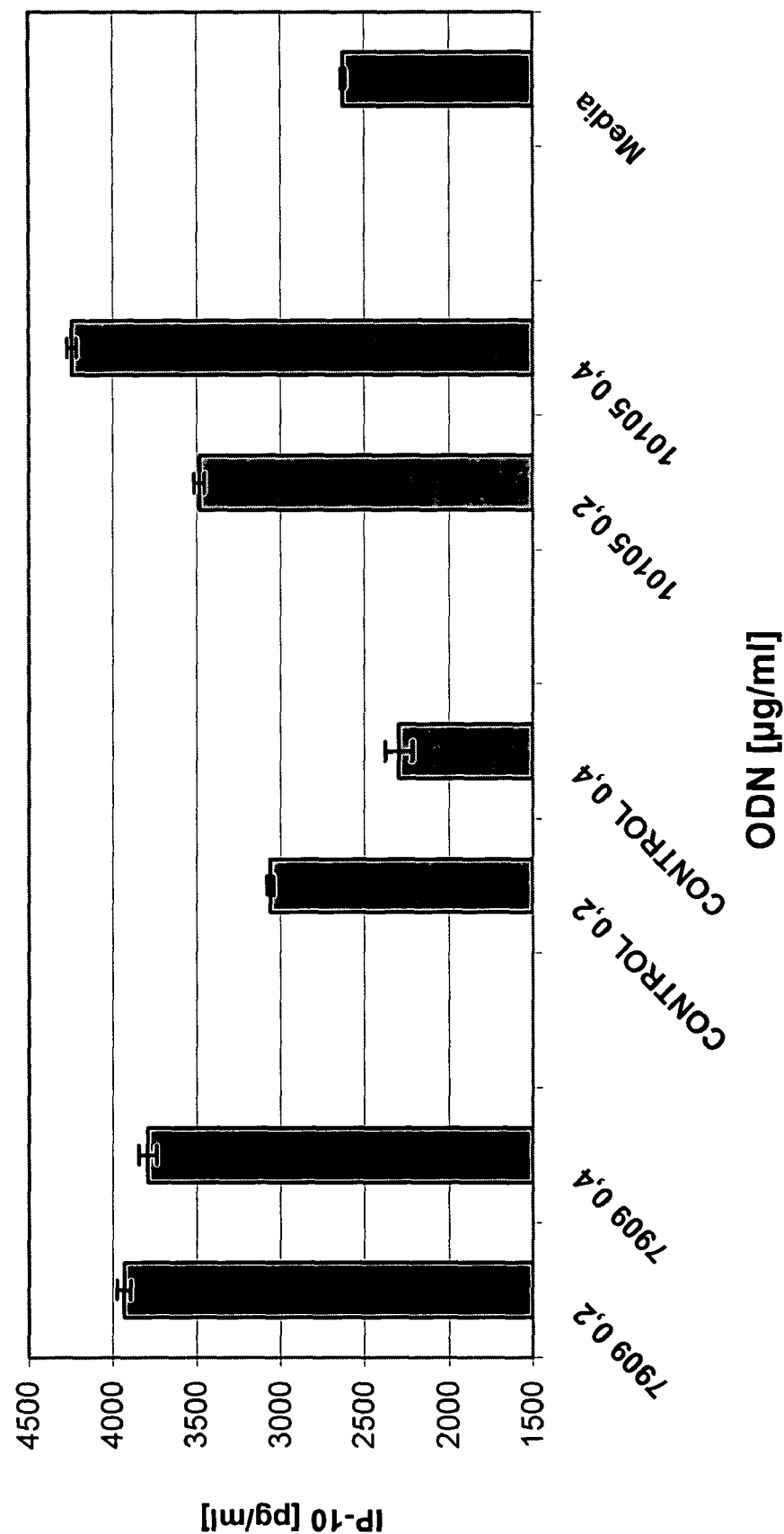
FIG. 5: IP-10 secretion induced by ODNs 7909 and 10105. Human PBMC of three different donors were incubated with the indicated concentrations of ODNs for 48 h. The supernatant was harvested and IP-10 was measured by ELISA (see Materials and Methods). Shown are the mean amounts of IP-10 obtained for the three different donors at each concentration.

Both CpG ODNs induced high levels of IFN-α with a maximum reached at 0.4 to 1.6 μg/ml. In contrast, the control ODN induced low amounts of IFN-α starting only at 5.0 μg/ml. ODN 10105 induced higher levels of IFN-α at both the 1.6 and 5.0 μg/ml doses, as compared to ODN 7909. The ODNs 7909 and 10105, in contrast to the control ODN, induced the chemokine IP-10 as shown in FIG. 5, again with ODN 10105 inducing higher levels at the 0.4 μg/ml dose.

Figure 6:
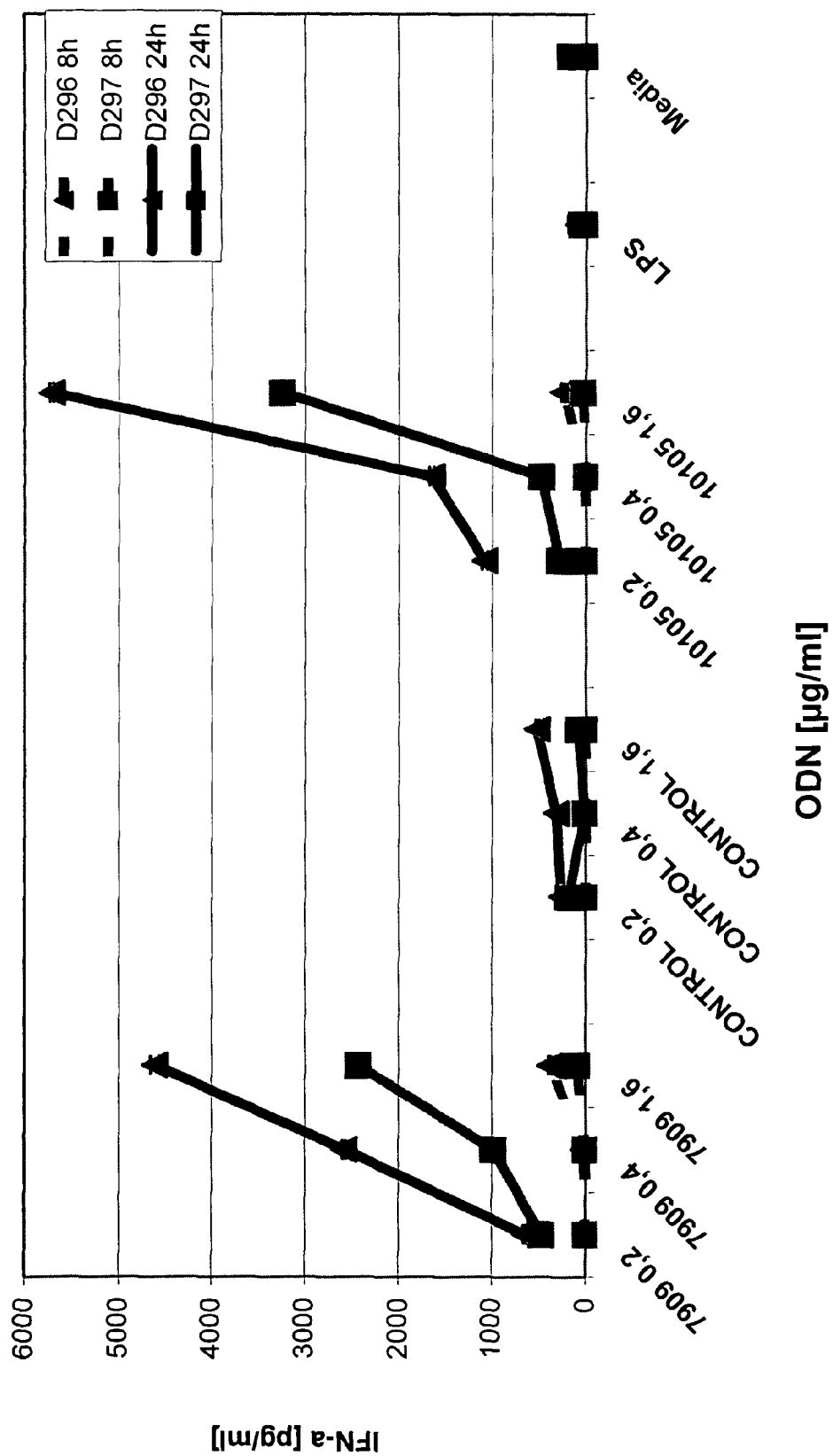
FIG. 6: Time kinetic for IFN-α secretion. PBMC of two different blood donors were incubated with the indicated concentrations of ODNs 7909, 10105 or a control for 8 h or 24 h. Supernatants were harvested and IFN-α measured by ELISA. Shown are the individual IFN-α amounts obtained at the different time points for the two donors.
Figure 7:
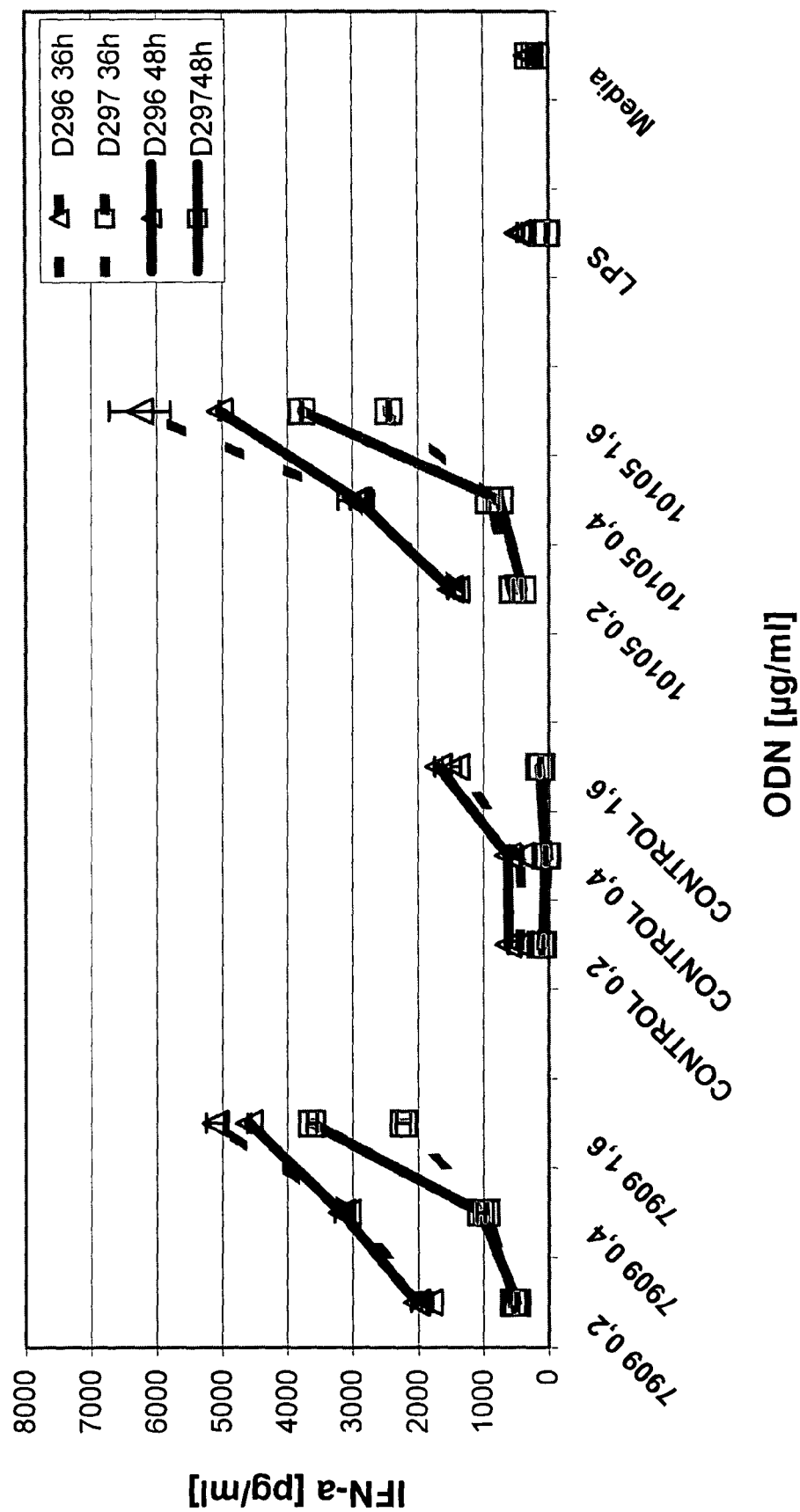
FIG. 7: Time kinetic for IFN-α secretion. PBMC of two different blood donors were incubated with the indicated concentrations of ODNs 7909, 10105 or a control for 36 h or 48 h. Supernatants were harvested and IFN-α measured by ELISA. Shown are the individual IFN-α amounts obtained at the different time points for the two donors.

The time-dependent effects on different cytokines were also analyzed. Therefore, PBMC from different donors were incubated for 8 h, 24 h, 36 h and/or 48 h and the secretion of IL-10 or IFN-α was measured. FIGS. 6 and 7 demonstrate the results obtained for IFN-α with two different donors upon incubation for 8 h and 24 h (FIG. 6) or 36 h and 48 h (FIG. 7). IFN-α was initially secreted as early as 8 h upon incubation with CpG ODN, maximum amounts were reached at 24 h and the amounts stayed at that level or even increased between 24 h and 48 h. LPS did not induce any IFN-α. For both donors, the ODN 10105 stimulated higher levels of IFN-α at the 8 hour time point at a concentration of 1.6 μg/ml.

Figure 8:
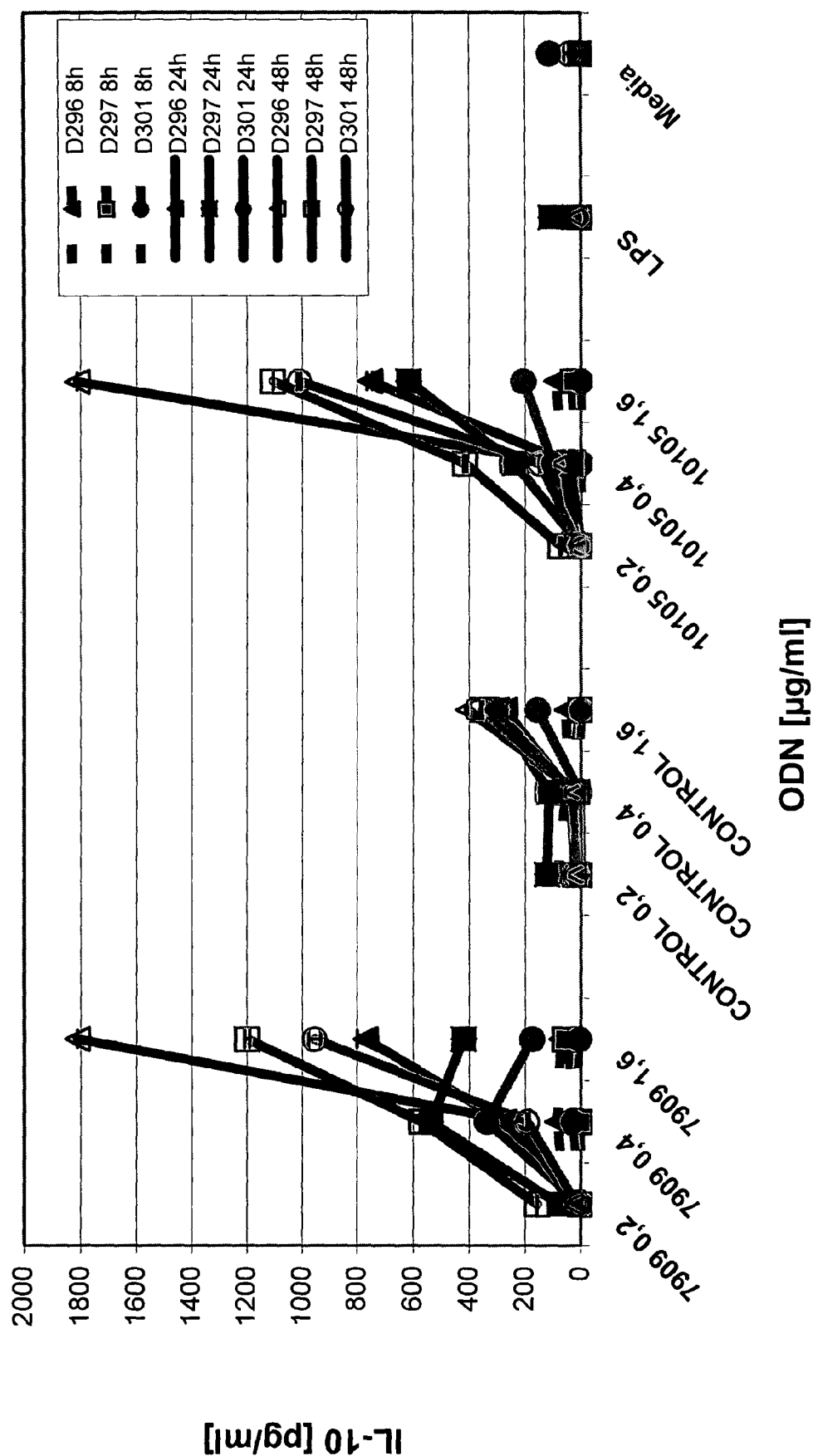
FIG. 8: Time kinetic for IL-10 secretion. PBMC of three different blood donors were incubated with the indicated concentrations of ODNs 7909, 10105 or a control for 8 h, 24 h or 48 h. Supernatants were harvested and IL-10 measured by ELISA. Shown are the individual IL-10 amounts obtained at the different time points for the three donors.
Figure 9:
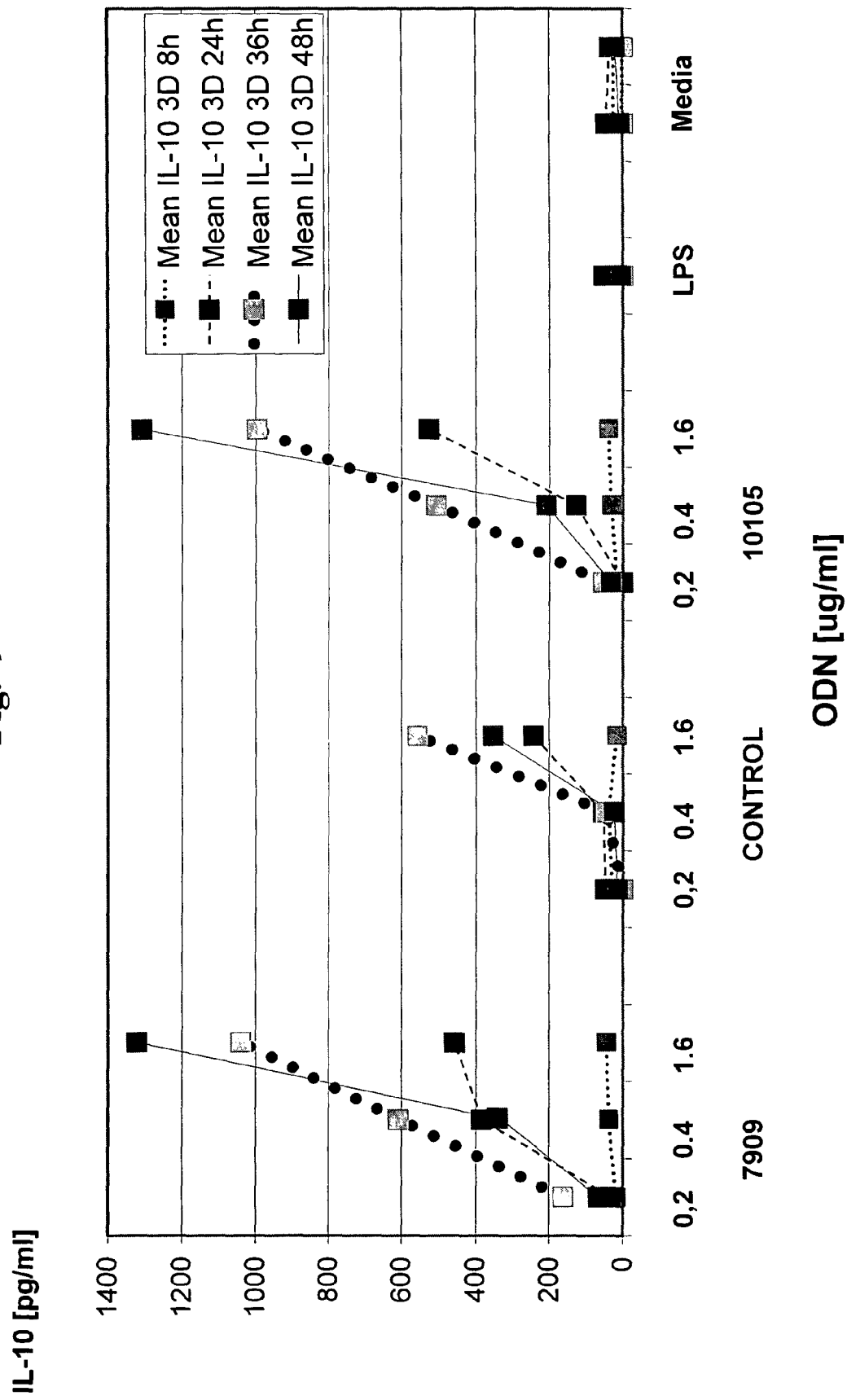
FIG. 9: Time kinetic for IL-10 secretion. Shown is the same experiment as in FIG. 8. The mean amounts of IL-10 at each concentration and time point between the three donors were calculated.

A very similar experiment was performed for IL-10 secretion (FIGS. 8 and 9). This cytokine showed similar characteristics to IFN-α although maximum amounts were obtained at a 48 h. Again, as demonstrated above for IFN-α, both CpG ODNs 7909 and 10105 demonstrated almost identical properties in these as in all other assays performed.

Figure 10:
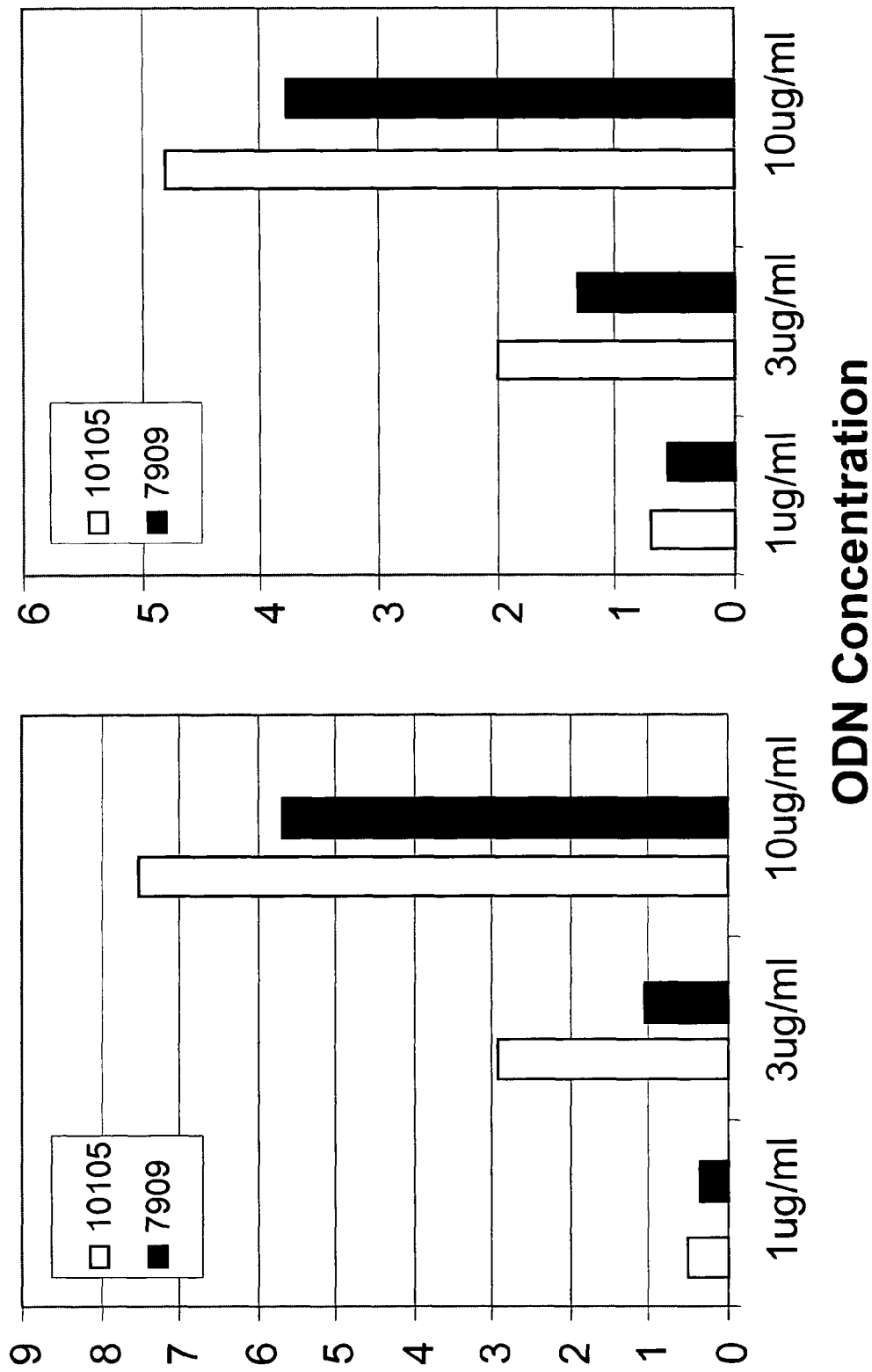
FIG. 10: Naïve BALB/c mouse splenocytes ($5 \times 10^6$/ml or $2.5 \times 10^6$/ml) were incubated with media (negative control) or different amounts of CpG ODN 7909 and 10105. Cells were pulsed with $^3$H-thymidine (20 μCi/ml) at 96 hr post incubation for 16 hours, harvested and measured for radioactivity. Each bar represents the stimulation index (counts/min (CPM) of cells incubated/CPM of cells incubated with media).

In vitro mouse studies:

As shown in FIG. 10, ODN 10105 is able to stimulate higher levels of B cell proliferation than ODN 7909 at all concentrations tested. According to the data shown in FIG. 11, both CpG ODN 7909 and 10105 are able to stimulate IL-10, IL-12, IL-6 and TNF-secretion. For IL-12 and TNF-secretion, ODN 10105 elicits more factor secretion at all concentrations tested than does 7909.

Figure 12:
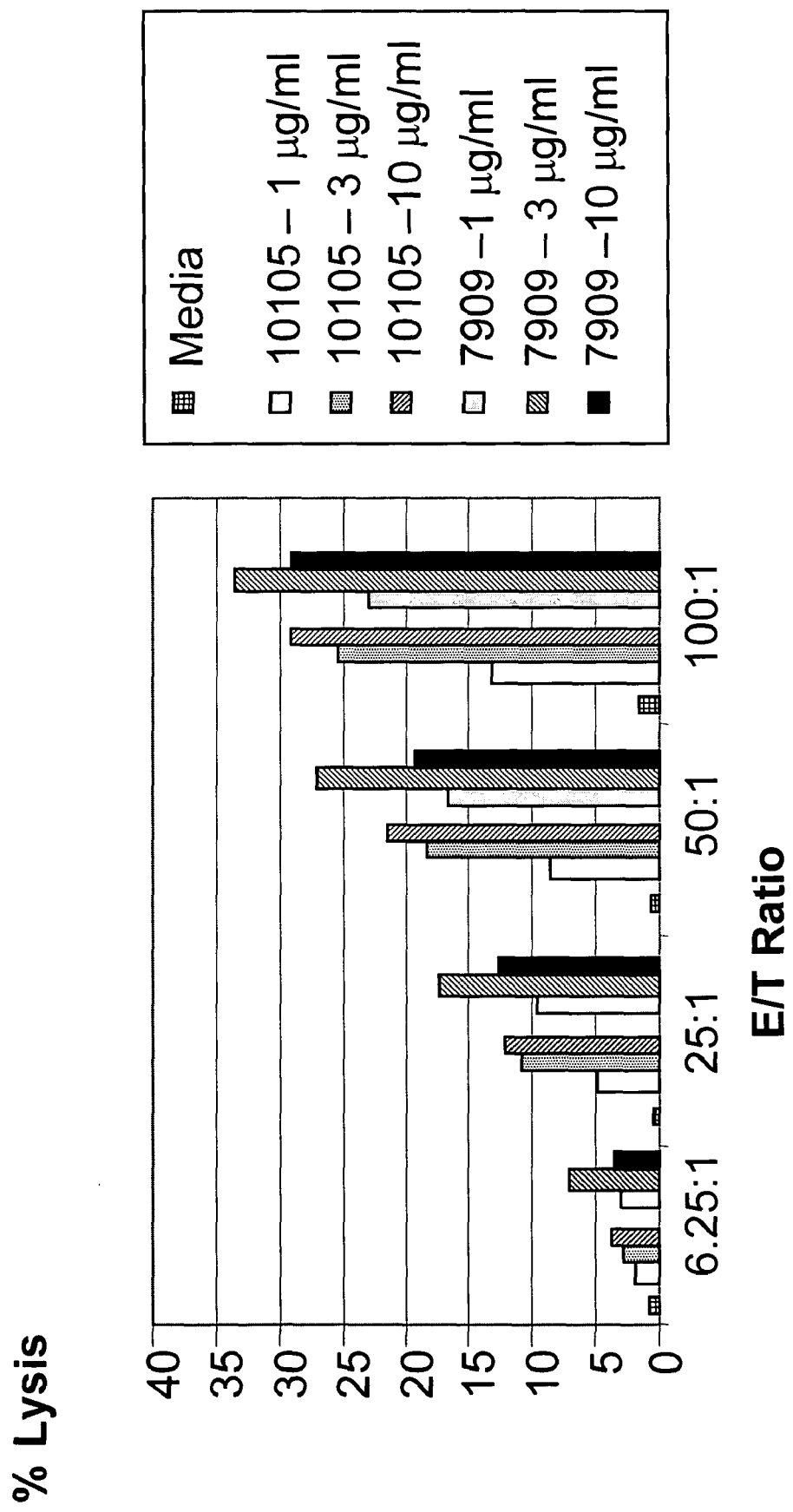
FIG. 12: Naïve BALB/c mouse splenocytes ($30 \times 10^6$/ml) were incubated with media (negative control) or different amounts of CpG ODN 7909 and 10105. NK activity was measured by using $^{51}$Cr release assay.

The CpG ODN have essentially equal potency in enhancing lytic activity of NK cells in mouse splenocyte cultures (FIG. 12).

Figure 13:
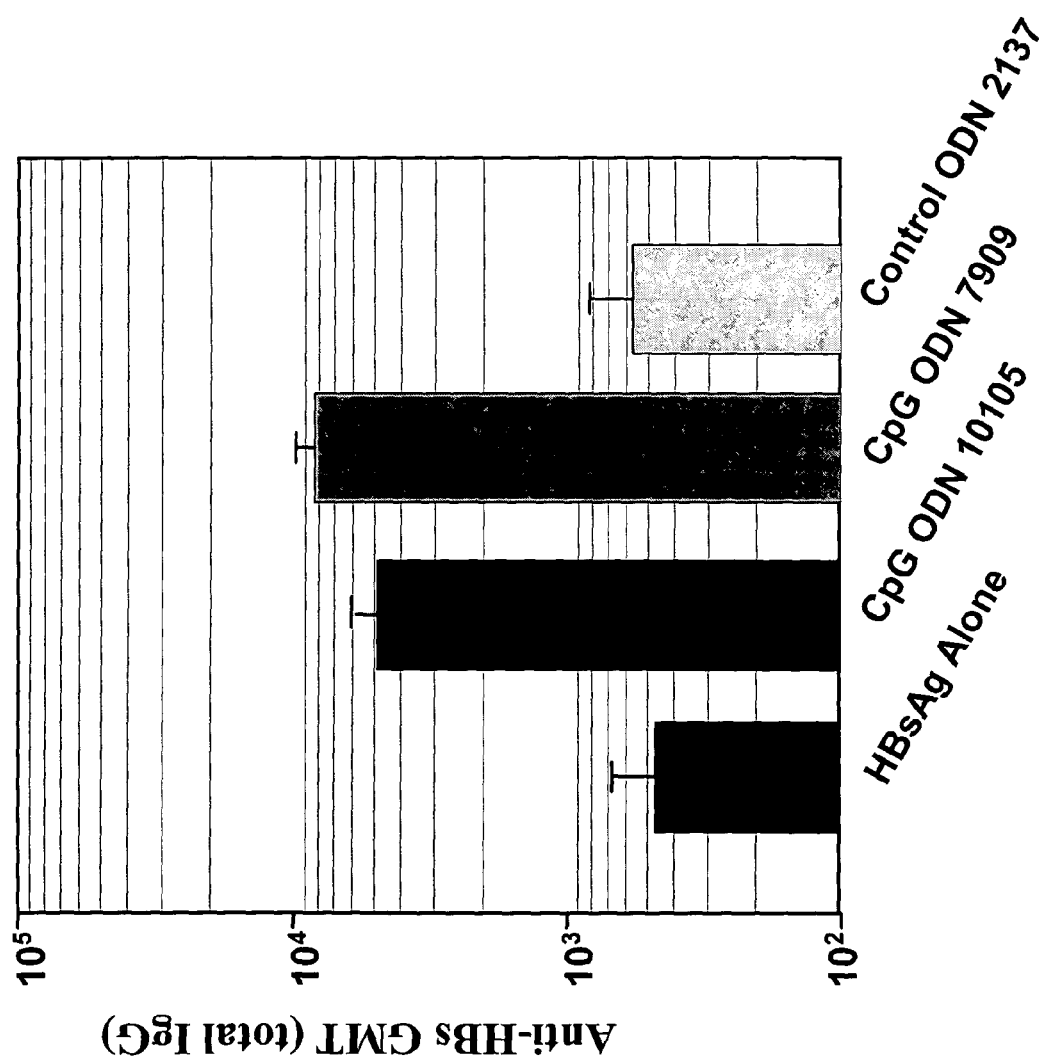
FIG. 13: Adult (6-8 wk) BALB/c mice were immunized with 1 μg of HBsAg alone or in combination with CpG ODN (10 μg) 10105, 7909 or control ODN (10 μg) 2137. Animals were bled at 4 weeks post immunization and plasma was assayed for total IgG levels against HBsAg (Anti-HBs). Each bar represents the geometric mean (±SEM) of the ELISA end point dilution titer for the entire group (n=10). Titers were defined as the highest dilution resulting in an absorbance value two times that of non-immune plasma with a cut-off value of 0.05.

As shown in FIG. 13, either CpG ODN 7909 or 10105 significantly enhanced antibody titers against HBsAg compared to antigen alone (p<0.0001) whereas there was no significant increase in anti-HBs responses when control ODN was used in combination with HBsAg (p=0.85).

Figure 14:
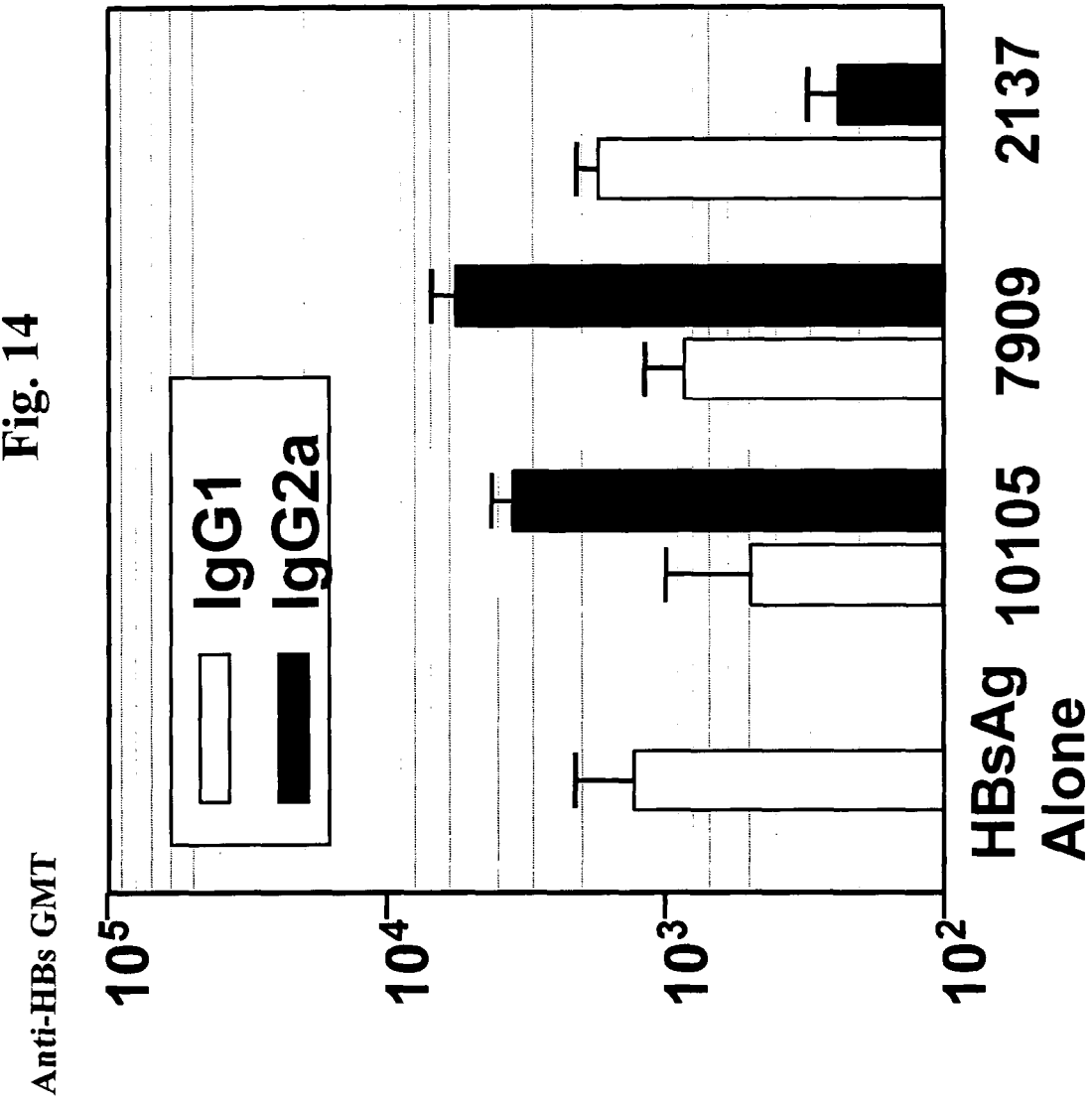
FIG. 14: Adult BALB/c mice (6-8 wks old) were immunized with 1 μg of HBsAg alone or in combination with 10 μg CpG ODN 7909, 10105 or 10 μg control ODN 2137. Animals were bled at 4 weeks post immunization and plasma was assayed for IgG1 and IgG2a levels against HBsAg (Anti-HBs). Each bar represents the geometric mean (±SEM) of the ELISA end point dilution titer for the entire group (n=10). Titers were defined as the highest dilution resulting in an absorbance value two times that of non-immune plasma with a cut-off value of 0.05.

As shown in FIG. 14, the increase in total IgG levels is similar both the CpG ODN.

In mice IgG isotype distribution is widely used as an indication of the nature of the immune response where high IgG2a/IgG1 ratios are indicative of a Th1 biased immune response (Constant and Bottomly, 1997). In the present study, the use of CpG ODN significantly enhanced IgG2a titers compared to when antigen was used alone or in combination with control ODN 2137 (p<0.001 for Ag vs. 7909 or 10105 and p<0.01 for Ag+7909 vs. Ag+2137 and p<0.05 for Ag+10105 vs. Ag+2137). However, the level of IgG2a response was similar when either CpG ODN 7909 or 10105 was used in combination with HBsAg (p>0.05). Therefore, both CpG ODN 7909 and 10105 are equally potent in their ability to induce Th1 biased immune responses as measured by the increased levels of IgG2a over IgG1.

Conclusions:

In vitro data with human cells demonstrating that ODN 10105 behaves similarly and in some instances, in a manner superior to that of ODN 7909 is demonstrated. According to the results of the murine studies, CpG ODN 7909 and 10105 have similar immune potentiating properties, both for their in vitro effects on innate immune responses as well as their ability to augment antigen specific responses in vivo when administered together with an antigen.

References

1. Bauer, S. et al.; Human TLR9 confers responsiveness to bacterial DNA via species-specific CpG motif recognition; PNAS 98, 2001.

2. Constant, S. L., and K. Bottomly 1997. Induction of Th1 and Th2 CD4+T cell responses: the alternative approaches Annu Rev Immunol. 15:297-322.

3. Hemmi, H. et al.; A Toll-like receptor recognizes bacterial DNA; Nature 408, 2000.

4. Krieg, A. M. et al.; CpG motifs in bacterial DNA trigger direct B-cell activation; Nature 374, 1995.

5. Krug, A. et al.; Toll-like receptor expression reveals CpG DNA as a unique microbial stimulus for pDC which synergizes with CD40 ligand to induce high amounts of IL-12; Eur. J. Immunol. 31; 2001.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

I claim:

1. A composition comprising an immunostimulatory nucleic acid comprising the nucleotide sequence of SEQ ID NO:1.

2. The composition of claim 1, wherein the immunostimulatory nucleic acid consists of the nucleotide sequence of SEQ ID NO:1.

3. The composition of claim 1, further comprising an antigen.

4. The composition of claim 3, wherein the antigen is selected from the group consisting of a microbial antigen, a cancer antigen, and an allergen.

5. The composition of claim 4, wherein the microbial antigen is selected from the group consisting of a bacterial antigen, a viral antigen, a fungal antigen and a parasitic antigen.

6. The composition of claim 3, wherein the antigen is encoded by a nucleic acid vector.

7. The composition of claim 3, wherein the nucleic acid vector is separate from the immunostimulatory nucleic acid.

8. The composition of claim 3, wherein the antigen is a peptide antigen.

9. The composition of claim 1, further comprising an adjuvant.

10. The composition of claim 9, wherein the adjuvant is a mucosal adjuvant.

11. The composition of claim 1, further comprising a cytokine.

12. The composition of claim 1, further comprising a therapeutic agent selected from the group consisting of an antimicrobial agent, an anti-cancer agent, and an allergy/asthma medicament.

13. The composition of claim 12, wherein the anti-microbial agent is selected from the group consisting of an antibacterial agent, an anti-viral agent, an anti-fungal agent, and an anti-parasite agent.

14. The composition of claim 12, wherein the allergy/asthma medicament is selected from the group consisting of PDE-4 inhibitor, bronchodilator/beta-2 agonist, K+ channel opener, VLA-4 antagonist, neurokin antagonist, TXA2 synthesis inhibitor, xanthanine, arachidonic acid antagonist, 5 lipoxygenase inhibitor, thromboxin A2 receptor antagonist, thromboxane A2 antagonist, inhibitor of 5-lipox activation protein, and protease inhibitor.

15. The composition of claim 1, wherein the immunostimulatory nucleic acid has a nucleotide backbone which includes at least one phosphorothioate backbone modification.

16. The composition of claim 15, wherein the nucleotide backbone is entirely modified.

17. The composition of claim 1, further comprising a pharmaceutically acceptable carrier.

18. The composition of claim 1, wherein the immunostimulatory nucleic acid includes more than four CpG motifs.

19. The composition of claim 1, wherein the immunostimulatory nucleic acid is formulated as a nutritional supplement.

20. The composition of claim 19, wherein the nutritional supplement is formulated as a capsule, a pill, or a sublingual tablet.

21. The composition of claim 1, wherein the immunostimulatory nucleic acid is formulated for local administration.

22. The composition of claim 1, wherein the immunostimulatory nucleic acid is formulated for parenteral administration.

23. The composition of claim 1, wherein the immunostimulatory nucleic acid is formulated in a sustained release device.

24. The composition of claim 1, wherein the immunostimulatory nucleic acid is formulated for delivery to a mucosal surface.

25. The composition of claim 23, wherein the sustained release device is a microparticle.

26. A method for stimulating an immune response in a subject in need thereof comprising
administering to a subject an immunostimulatory nucleic acid comprising the nucleotide sequence of SEQ ID NO:1, in an amount effective to stimulate an immune response.

27. A method for inducing an innate immune response, comprising administering to the subject an immunostimulatory nucleic acid in an amount effective for activating an innate immune response, wherein the immunostimulatory nucleic acid has a nucleotide sequence comprising SEQ ID NO:1.

28. The composition of claim 1, wherein the immunostimulatory nucleic acid is up to 100 nucleotides in length.

29. The method of claim 26 or 27, wherein the immunostimulatory nucleic acid is up to 100 nucleotides in length.

* * * * *

SEQUENCE LISTING

<160> NUMBER OF SEQ ID NOS: 26

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tcgtcgtttt gtcgtttttt tcga                                          24

<210> SEQ ID NO 2
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 2
tcgtcgtttt gtcgttttgt cgtt                                          24

```
<210> SEQ ID NO 3
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: n is a, c, g, or t

<400> SEQUENCE: 3
nnnnnnnnnn nnnnnttttt tcga                                          24

<210> SEQ ID NO 4
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 4 tttttttcga                                                           9

<210> SEQ ID NO 5
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(24)
<223> OTHER INFORMATION: n is a, c, g, or t

<400> SEQUENCE: 5
tcgtcgtttt gtcgttttn nnnn                                           24

<210> SEQ ID NO 6
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 6
tcgtcgtttt gtcgttttt                                                19

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 7
tcgtcgtttt gtcgtttttt tcg                                           23

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
tcgtcgtttt gtcgtttttt tc                                            22
```

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
tcgtcgtttt gtcgtttttt t                                     21

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
tcgtcgtttt gtcgttttt                                        20

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
cgtcgttttg tcgttttttt cga                                   23

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
gtcgttttgt cgttttttc ga                                     22

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
tcgttttgtc gttttttcg a                                      21

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cgttttgtcg ttttttcga                                        20

<210> SEQ ID NO 15
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 15
gttttgtcgt tttttcga					19

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
ttttgtcgtt ttttcga					18

<210> SEQ ID NO 17
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 17
tttgtcgttt tttcga					17

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
ttgtcgtttt tttcga					16

<210> SEQ ID NO 19
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 19
tgtcgttttt ttcga					15

<210> SEQ ID NO 20
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 20
gtcgtttttt tcga						14

<210> SEQ ID NO 21
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 21
tcgttttttt cga						13

-continued

```
<210> SEQ ID NO 22
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 22 cgttttttc ga                                                          12

<210> SEQ ID NO 23
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 23 gttttttcg a                                                           11

<210> SEQ ID NO 24
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 24
tttttttcga                                                            10

<210> SEQ ID NO 25
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(23)
<223> OTHER INFORMATION: n is a, c, g, or t; and any 0-20 may be absent.

<400> SEQUENCE: 25
gggnnnnnnn nnnnnnnnnn nnnggg                                          26

<210> SEQ ID NO 26
<211> LENGTH: 49
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(23)
<223> OTHER INFORMATION: n is a, c, g, or t; and any 0-20 may be absent.
<220> FEATURE:
<221> NAME/KEY: misc_feature
<222> LOCATION: (27)..(46)
<223> OTHER INFORMATION: n is a, c, g, or t; and any 0-20 may be absent.

<400> SEQUENCE: 26
gggnnnnnnn nnnnnnnnnn nnnggnnnn nnnnnnnnnn nnnnnnggg                  49
```